US012692250B2

(12) United States Patent
Buhrlage et al.

(10) Patent No.: US 12,692,250 B2
(45) Date of Patent: Jul. 28, 2026

(54) USP7 INHIBITORS FOR TREATING MULTIPLE MYELOMA

(71) Applicant: Dana-Farber Cancer Institute, Inc., Boston, MA (US)

(72) Inventors: Sara Buhrlage, Somerville, MA (US); Kenneth C. Anderson, Wellesley, MA (US); Dharminder Chauhan, Natick, MA (US); Sirano Dhe-Paganon, Holliston, MA (US); Xiaoxi Liu, Burlington, MA (US); Hyuk-Soo Seo, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 85 days.

(21) Appl. No.: 17/902,512

(22) Filed: Sep. 2, 2022

(65) Prior Publication Data

US 2023/0265070 A1 Aug. 24, 2023

Related U.S. Application Data

(63) Continuation of application No. 16/650,727, filed as application No. PCT/US2018/052797 on Sep. 26, 2018, now Pat. No. 11,465,983.

(60) Provisional application No. 62/563,375, filed on Sep. 26, 2017.

(51) Int. Cl.

| | |
|---|---|
| ***C07D 401/14*** | (2006.01) |
| ***C07D 401/06*** | (2006.01) |
| ***C07D 403/06*** | (2006.01) |
| ***C07D 413/14*** | (2006.01) |

(52) U.S. Cl.

CPC ......... *C07D 401/14* (2013.01); *C07D 401/06* (2013.01); *C07D 403/06* (2013.01); *C07D 413/14* (2013.01)

(58) Field of Classification Search

None

See application file for complete search history.

(56) References Cited

U.S. PATENT DOCUMENTS

| | | | |
|---|---|---|---|
| 11,465,983 | B2 | 10/2022 | Buhrlage et al. |
| 12,503,453 | B2 | 12/2025 | Buhrlage et al. |
| 2009/0170881 | A1 | 7/2009 | Angibaud et al. |
| 2014/0371247 | A1 | 12/2014 | Colland et al. |
| 2016/0229833 | A1 | 8/2016 | Ioannidis et al. |
| 2016/0229872 | A1 | 8/2016 | Ioannidis et al. |
| 2018/0162835 | A1 | 6/2018 | Ioannidis et al. |
| 2020/0347031 | A1 | 11/2020 | Buhrlage et al. |
| 2021/0347761 | A1 | 11/2021 | Buhrlage et al. |
| 2024/0376076 | A1 | 11/2024 | Buhrlage et al. |

FOREIGN PATENT DOCUMENTS

| | | | |
|---|---|---|---|
| EP | 2565186 | A1 | 3/2013 |
| JP | H11171774 | A | 6/1999 |
| WO | WO-98/033792 | A1 | 8/1998 |
| WO | WO-99/53924 | A1 | 10/1999 |
| WO | WO-2007/147217 | A1 | 12/2007 |
| WO | WO-2013/030218 | A1 | 3/2013 |
| WO | WO-2016/109480 | A1 | 7/2016 |
| WO | WO-2016/109515 | A1 | 7/2016 |
| WO | WO-2016/126926 | A1 | 8/2016 |
| WO | WO-2018/020242 | A1 | 2/2018 |
| WO | WO-2018/073602 | A1 | 4/2018 |
| WO | WO-2019/067503 | A1 | 4/2019 |
| WO | WO-2020/086595 | A1 | 4/2020 |
| WO | WO-2020/086595 | A8 | 7/2020 |
| WO | WO-2023/003973 | | 1/2023 |

OTHER PUBLICATIONS

Database Registry Chemical Abstracts Service, Columbus, Ohio, Accession No. RN 1381443-96-4, Entered STN: Jul. 4, 2012.*
Database Registry Chemical Abstracts Service, Columbus, Ohio, Accession No. RN 1426340-65-9, Entered STN: Mar. 26, 2013.*
Database Registry Chemical Abstracts Service, Columbus, Ohio, Accession No. RN 1381349-35-4, Entered STN: Jul. 4, 2012.*
Database Registry Chemical Abstracts Service, Columbus, Ohio, Accession No. RN 1381291-29-7, Entered STN: Jul. 4, 2012.*
Database Registry Chemical Abstracts Service, Columbus, Ohio, Accession No. RN 1381291-44-6, Entered STN: Jul. 4, 2012.*
Database Registry Chemical Abstracts Service, Columbus, Ohio, Accession No. RN 1381589-44-1, Entered STN: Jul. 4, 2012.*
U.S. Appl. No. 16/650,727, Issued.
U.S. Appl. No. 17/286,219, Pending.
Database Registry Chemical Abstracts Service, Accession No. RN 1381443-96-4, Entered STN: Jul. 4, 2012.
Database Registry Chemical Abstracts Service, Accession No. RN 1797702-91-0, Entered STN: Jul. 9, 2015.
Extended European Search Report for EP Application No. 18862773.1 dated May 19, 2021.
International Search Report and Written Opinion for International Application No. PCT/US19/57456 dated Feb. 6, 2020.

(Continued)

*Primary Examiner* — Samantha L Shterengarts
(74) *Attorney, Agent, or Firm* — Foley Hoag LLP; DeAnn F. Smith; Laura A. Wzorek

(57) ABSTRACT

The present disclosure relates to inhibitors of USP7 useful in the treatment of cancers, and other USP7 mediated diseases, having the Formula:

(I)

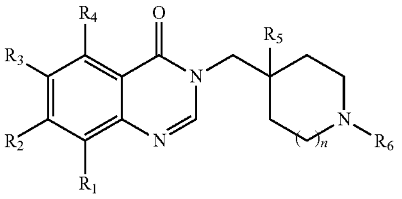

wherein $R_1$, $R_2$, $R_3$, $R_4$, $R_5$, $R_6$, and n are described herein.

19 Claims, 16 Drawing Sheets

Specification includes a Sequence Listing.

(56) References Cited

OTHER PUBLICATIONS

International Search Report and Written Opinion for International Application No. PCT/US2018/052797 dated Dec. 11, 2018.
Invitation to Pay Additional Fees for International Application No. PCT/US19/57456 dated Dec. 17, 2019.
Lamberto et al., "Structure-Guided Development of a Potent and Selective Non-Covalent Active-Site Inhibitor of USP7," Cell Chemical Biology, 24(1): 1490-1500 and e1-11 (2017).
Schauer et al., "Selective USP7 inhibition elicits cancer cell killing through a p53-dependent mechanism," Scientific Reports, 10:5324 (2020).
Desroses et al., "The Next Step Forward in Ubiquitin-Specific Protease 7 Selective Inhibition" Cell Chemical Biology, 2017, 24(12), pp. 1429-1431.
Dowd et al., "Identification and Structure-Guided Development of Pyrimidinone Based USP7 Inhibitors", Acs Medicinal Chemistry Letters, vol. 9, No. 3, pp. 238-243 (2018).
Extended European Search Report for EP Application No. 19874929.3 dated Oct. 25, 2022.
Invitation to Pay Additional Fees for Application No. PCT/US2022/037756 dated Oct. 31, 2022.
Database Registry CAS, Accession No. RN 1381178-30-8, Entered STN: Jul. 4, 2012.
Database Registry CAS, Accession No. RN 1381291-50-4, Entered STN: Jul. 4, 2012.
Database Registry CAS, Accession No. RN 1381349-24-1, Entered STN: Jul. 4, 2012.
Database Registry CAS, Accession No. RN 1381444-09-2, Entered STN: Jul. 4, 2012.
Database Registry CAS, Accession No. RN 1381507-17-0, Entered STN: Jul. 5, 2012.
Database Registry CAS, Accession No. RN 1381589-44-1, Entered STN: Jul. 5, 2012.
Database Registry CAS, Accession No. RN 1381728-91-1, Entered STN: Jul. 5, 2012.
Notice of Allowance for U.S. Appl. No. 17/286,219 dated Jul. 29, 2025.
Database Registry CAS, Accession No. 1381443-88-4, Entered STN: Jul. 4, 2012.
Database Registry CAS, Accession No. 1381641-90-2, Entered STN: Jul. 5, 2012.
Database Registry CAS, Accession No. 1381642-23-4, Entered STN: Jul. 5, 2012.
Database Registry CAS, Accession No. 1381647-02-4, Entered STN: Jul. 5, 2012.
Database Registry CAS, Accession No. 1381647-21-7, Entered STN: Jul. 5, 2012.
Database Registry CAS, Accession No. 1381736-63-5, Entered STN: Jul. 5, 2012.
Database Registry CAS, Accession No. 1381736-70-4, Entered STN: Jul. 5, 2012.

* cited by examiner

P22077

P5091

HBX19818

HBX-41108

NSC632839

Spongiacidin C

Xestoquinone ent-13-norisocopalen-15-al-18-oic acid

Cmpd A

Cmpd 10

Cmpd 11

| Protein | Compound | $IC_{50}$ (μM) ± SEM (n) |
|---|---|---|
| USP7 catalytic domain (aa 208-560) | A | 12.3 ± 0.9 (18) |
| | 10 | 0.193 ± 0.006 (4) |
| | 11 | 10.7 ± 1.3 (2) |
| USP7 full length (aa 1-1102) | A | 10.2 ± 3.1 (3) |
| | 10 | 0.090 ± 0.016 (3) |
| | 11 | 7.18 ± 2.18 (3) |

| Mutation | Cmpd A $IC_{50}$ (uM) | Activity relative to WT in Ub-AMC assay |
|---|---|---|
| WT | 12 | = |
| Q351S | > 100 | = |
| M407K | 13 | -- |
| M410S | 48 | ++ |
| M407K/M410S | 9 | = |
| K420A | N/A | inactive |
| H456A | N/A | inactive |
| H461A | 16 | = |
| Y514A | > 100 | -- |

| ID | Structure | USP7 $IC_{50}$ (μM) | ID | Structure | USP7 $IC_{50}$ (μM) |
|---|---|---|---|---|---|
| A |  | 12 | 6 |  | > 100 |
| 2 |  | > 100 | 7 |  | > 100 |
| 3 |  | > 100 | 8 |  | 1.3 |
| 4 |  | > 100 | 1 |  | 0.42 |
| 5 |  | > 100 | 9 |  | 40 |

| ID | R | $R^1$ | USP7 $IC_{50}$ (μM) | MLM $t_{1/2}$ (min) |
|---|---|---|---|---|
| 12 |  | (rac)-Me | 0.56 | 33.7 |
| 10 |  | (R)-Me | 0.19 | 31.1 |
| 11 |  | (S)-Me | 11 | 19 |
| 13 |  | (rac)-*i*Pr | 0.27 | 13.6 |
| 14 |  | (R)-Me | 0.48 | 7.3 |
| 15 |  | (R)-Me | 0.13 | 21.1 |
| 16 |  | (rac)-Me | 0.24 | 3.9 |
| 17 |  | (rac)-Me | 0.35 | 7.3 |

SEQUENCE LISTING

```
Sequence total quantity: 16
SEQ ID NO: 1           moltype = DNA  length = 35
FEATURE                Location/Qualifiers
source                 1..35
                       mol_type = other DNA
                       note = primer
                       organism = synthetic construct
SEQUENCE: 1
gaagattatt atgatatctc gctaagtatc aaagg                      35

SEQ ID NO: 2           moltype = DNA  length = 35
FEATURE                Location/Qualifiers
source                 1..35
                       mol_type = other DNA
                       note = primer
                       organism = synthetic construct
SEQUENCE: 2
cctttgatac ttagcgagat atcataataa tcttc                      35

SEQ ID NO: 3           moltype = DNA  length = 41
```

-continued

```
FEATURE                 Location/Qualifiers
source                  1..41
                        mol_type = other DNA
                        note = primer
                        organism = synthetic construct
SEQUENCE: 3
ccagtgttac atctacaact gaagagattt atgtatgacc c                      41

SEQ ID NO: 4            moltype = DNA  length = 41
FEATURE                 Location/Qualifiers
source                  1..41
                        mol_type = other DNA
                        note = primer
                        organism = synthetic construct
SEQUENCE: 4
gggtcataca taaatctctt cagttgtaga tgtaacactg g                      41

SEQ ID NO: 5            moltype = DNA  length = 40
FEATURE                 Location/Qualifiers
source                  1..40
                        mol_type = other DNA
                        note = primer
                        organism = synthetic construct
SEQUENCE: 5
ctacaactga tgagatttag ttatgaccct cagacggacc                        40

SEQ ID NO: 6            moltype = DNA  length = 40
FEATURE                 Location/Qualifiers
source                  1..40
                        mol_type = other DNA
                        note = primer
                        organism = synthetic construct
SEQUENCE: 6
ggtccgtctg agggtcataa ctaaatctca tcagttgtag                        40

SEQ ID NO: 7            moltype = DNA  length = 52
FEATURE                 Location/Qualifiers
source                  1..52
                        mol_type = other DNA
                        note = primer
                        organism = synthetic construct
SEQUENCE: 7
ccagtgttac atctacaact gaagagattt agttatgacc ctcagacgga cc          52

SEQ ID NO: 8            moltype = DNA  length = 52
FEATURE                 Location/Qualifiers
source                  1..52
                        mol_type = other DNA
                        note = primer
                        organism = synthetic construct
SEQUENCE: 8
ggtccgtctg agggtcataa ctaaatctct tcagttgtag atgtaacact gg          52

SEQ ID NO: 9            moltype = DNA  length = 47
FEATURE                 Location/Qualifiers
source                  1..47
                        mol_type = other DNA
                        note = primer
                        organism = synthetic construct
SEQUENCE: 9
ccctcagacg gaccaaaata tcgcgatcaa tgataggttt gaattcc                47

SEQ ID NO: 10           moltype = DNA  length = 47
FEATURE                 Location/Qualifiers
source                  1..47
                        mol_type = other DNA
                        note = primer
                        organism = synthetic construct
SEQUENCE: 10
ggaattcaaa cctatcattg atcgcgatat tttggtccgt ctgaggg                47

SEQ ID NO: 11           moltype = DNA  length = 41
FEATURE                 Location/Qualifiers
source                  1..41
                        mol_type = other DNA
                        note = primer
                        organism = synthetic construct
SEQUENCE: 11
cttcatgcag tcctggttgc tagtggagat aatcatggtg g                      41
```

-continued

```
SEQ ID NO: 12          moltype = DNA  length = 41
FEATURE                Location/Qualifiers
source                 1..41
                       mol_type = other DNA
                       note = primer
                       organism = synthetic construct
SEQUENCE: 12
ccaccatgat tatctccact agcaaccagg actgcatgaa g                        41

SEQ ID NO: 13          moltype = DNA  length = 40
FEATURE                Location/Qualifiers
source                 1..40
                       mol_type = other DNA
                       note = primer
                       organism = synthetic construct
SEQUENCE: 13
ctggttcata gtggagataa tgctggtgga cattatgtgg                          40

SEQ ID NO: 14          moltype = DNA  length = 40
FEATURE                Location/Qualifiers
source                 1..40
                       mol_type = other DNA
                       note = primer
                       organism = synthetic construct
SEQUENCE: 14
ccacataatg tccaccagca ttatctccac tatgaaccag                          40

SEQ ID NO: 15          moltype = DNA  length = 40
FEATURE                Location/Qualifiers
source                 1..40
                       mol_type = other DNA
                       note = primer
                       organism = synthetic construct
SEQUENCE: 15
cgacactgca ctaatgctgc catgttagtc tacatcaggg                          40

SEQ ID NO: 16          moltype = DNA  length = 40
FEATURE                Location/Qualifiers
source                 1..40
                       mol_type = other DNA
                       note = primer
                       organism = synthetic construct
SEQUENCE: 16
ccctgatgta gactaacatg gcagcattag tgcagtgtcg                          40
```

USP7 INHIBITORS FOR TREATING MULTIPLE MYELOMA

RELATED APPLICATIONS

This application is a continuation of U.S. application Ser. No. 16/650,727, filed Mar. 25, 2020, which is the § 371 National Stage of PCT/US2018/052797, filed Sep. 26, 2018, which claims the benefit of U.S. Provisional Patent Application No. 62/563,375, filed on Sep. 26, 2017. The contents of each of these applications are hereby incorporated by reference in their entirety.

STATEMENT OF RIGHTS

This invention was made with government support under Grant RO1 CA211681 awarded by the National Institutes of Health. The U.S. government has certain rights in the invention.

REFERENCE TO A SEQUENCE LISTING XML

This application contains a Sequence Listing which has been submitted electronically in XML format. The Sequence Listing XML is incorporated herein by reference. Said XML file, created on Feb. 28, 2023, is named DFS-18402_SL.xml and is 18,173 bytes in size

BACKGROUND

Deubiquitinating enzymes (DUBs) have garnered significant attention as drug targets in the last 5-10 years. DUB inhibitors effectively promote degradation of oncogenic proteins, especially proteins that are challenging to directly target because they are stabilized by DUB family members. Highly-optimized and well-characterized DUB inhibitors have thus become highly sought after tools. Most reported DUB inhibitors, however, are polypharmacological agents possessing weak (micromolar) potency toward their primary target, thereby limiting their utility in target validation and mechanism studies. Due to a lack of high resolution DUB·small molecule ligand complex structures, no structure-guided optimization efforts have been reported for a mammalian DUB.

The DUB enzyme USP7 has been shown to be involved in regulation of a myriad of cellular processes, including epigenetics, cell cycle, DNA repair, immunity, viral infection and tumorigenesis. USP7, also known as herpes virus-associated ubiquitin specific protease (HAUSP), was first discovered as a protein that plays a role in viral lytic growth. (Everett et al., Novel ubiquitin-specific protease is dynamically associated with the PML nuclear domain and binds to a herpesvirus regulatory protein. *EMBO J,* 16, 1997, 566-77.) Interest in the enzyme intensified when USP7 was implicated in regulating degradation of the tumor suppressor p53, by stabilizing the major E3 ligase for p53, MDM2. (Li et al., Deubiquitination of p53 by HAUSP is an important pathway for p53 stabilization. *Nature,* 416, 2002, 648-53; Cummins et al., Tumour suppression: disruption of HAUSP gene stabilizes p53. *Nature,* 428, 2004, 1 p following 486; Li et al., A dynamic role of HAUSP in the p53-Mdm2 pathway. *Mol Cell,* 13, 2004, 879-86).

Consistent with its regulation of diverse substrates and biological processes USP7 has emerged as a drug target in a wide range of malignancies including multiple myeloma, breast cancer, neuroblastoma, glioma, and ovarian cancer. (Chauhan et al., A small molecule inhibitor of ubiquitin-specific protease-7 induces apoptosis in multiple myeloma cells and overcomes bortezomib resistance. *Cancer Cell,* 22, 2012, 345-58; Wang et al., *J Clin Invest,* 126, 2016, 2205-20; Tavana et al., *Nat* Med, 22, 2016, 1180-1186; Cheng et al., Expression of HAUSP in gliomas correlates with disease progression and survival of patients. *Oncol Rep,* 29, 2013, 1730-6; Zhang et al., Expression of USP7 and MARCH7 Is Correlated with Poor Prognosis in Epithelial Ovarian Cancer. *Tohoku J Exp Med,* 239, 2016, 165-75) However, known USP7 inhibitors have been shown to exhibit modest potency against USP7 and poor selectivity over other DUBs. In addition to modest potency and selectivity, reported drawbacks of known USP7 inhibitor compounds include poor solubility and general toxicity. (Chen et al., Synthesis and biological evaluation of thiazole derivatives as novel USP7 inhibitors. *Bioorg Med Chem Lett,* 27, 2017, 845-849). Therefore, there is a need for the development of more potent, selective, soluble USP7 inhibitors with reduced toxicity.

SUMMARY

Disclosed herein are compounds of Formula (I):

(I)

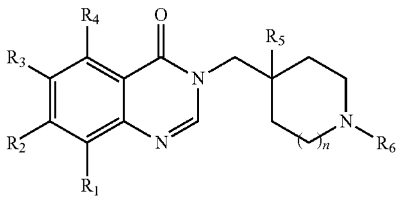

or a pharmaceutically acceptable salt thereof, wherein:

$R_1$ is H, halogen, alkyl, haloalkyl, alkoxy, haloalkoxy, —OH, —$NO_2$, —$NH_2$, CN, —$NR_7C$(═O)alkyl, —C(═O)$NR_7$alkyl, or —$NR_7R_8$, wherein each alkyl is independently optionally substituted with one or more $R_9$;

$R_2$ is H, halogen, alkyl, haloalkyl, alkoxy, haloalkoxy, —OH, —$NH_2$, —$NO_2$, CN, —$NR_7C$(═O)alkyl, —C(═O)$NR_7$alkyl, or —$NR_7R_8$, wherein each alkyl is independently optionally substituted with one or more $R_9$;

$R_3$ is H, halogen, alkyl, haloalkyl, alkoxy, haloalkoxy, —OH, —$NH_2$, —$NO_2$, CN, —$NR_7C$(═O)alkyl, —C(═O)$NR_7$alkyl, or —$NR_7R_8$; wherein each alkyl is independently optionally substituted with one or more $R_9$;

$R_4$ is H, halogen, alkyl, haloalkyl, alkoxy, haloalkoxy, —OH, —$NO_2$, —$NH_2$, CN, —$NR_7C$(═O)alkyl, —C(═O)$NR_7$alkyl, or —$NR_7R_8$; wherein each alkyl is independently optionally substituted with one or more $R_9$; wherein $R_1$, $R_2$, $R_3$ and $R_4$ are not simultaneously H;

$R_5$ is H, halogen, —CN, —$OR_7$, or —$NR_7R_8$;

$R_6$ is alkyl, —C(═O)$R_{10}$, —C(═S)$R_{10}$, —C(O)$NR_7R_8$, cycloalkyl, heterocycloalkyl, aryl, or heteroaryl; wherein the cycloalkyl, heterocycloalkyl, aryl, heteroaryl are each independently optionally substituted with one or more $R_{11}$; and wherein the alkyl is substituted with one or more $R_{12}$;

each $R_7$ and $R_8$ is independently H, alkenyl, or alkyl;

each $R_9$ is independently at each occurrence —$NR_7R_8$, alkoxy, —$(OCH_2CH_2)_m$alkyl, cycloalkyl, heterocycloalkyl, aryl, or heteroaryl, wherein the alkyl and alkoxy are each independently optionally substituted with one or more substituents selected from alkoxy, haloalkoxy, halogen, and —OH; and wherein the cycloalkyl, heterocycloalkyl, aryl and heteroaryl are each independently optionally substituted with one or more substituents selected from alkyl, haloalkyl, alkoxy, haloalkoxy, halogen, $—N_3$, and —OH;

$R_{10}$ is alkyl, alkenyl, alkynyl, $—NR_7R_8$, cycloalkyl, heterocycloalkyl, aryl, amino, heteroalkyl, alkylamino, aminoalkyl or heteroaryl, wherein the alkyl, alkenyl, and alkynyl are each independently optionally substituted with one or more $R_{13}$; and wherein the cycloalkyl, heterocycloalkyl, aryl and heteroaryl are each independently optionally substituted with one or more $R_{12}$;

each $R_{11}$ is independently at each occurrence alkyl, haloalkyl, alkoxy, haloalkoxy, halogen, $—NO_2$, or —OH;

each $R_{12}$ is independently at each occurrence aryl or heteroaryl, wherein the aryl and heteroaryl are each independently optionally substituted with one or more substituents selected from alkyl, haloalkyl, alkoxy, haloalkoxy, halogen, and —OH;

each $R_{13}$ is independently at each occurrence —OH, alkoxy, heteroalkyl, aryloxy, $—NH_2$, arylalkyl, cycloalkyl, heterocycloalkyl, aryl, heteroaryl, —O-aryl, —O-heteroaryl, $—NR_7$aryl, $—NR_7$heteroaryl, or $—NR_7C(═O)R_{14}$, wherein the cycloalkyl, heterocycloalkyl, aryl, heteroalkyl, and heteroaryl are each independently optionally substituted with one or more substituents selected from alkyl, haloalkyl, alkoxy, haloalkoxy, halogen, $—NO_2$, and —OH;

$R_{14}$ is alkyl, haloalkyl, arylalkyl, alkenyl, alkynyl, cycloalkyl, aryl, heterocyclyl, or heteroaryl, wherein the aryl and heteroaryl are each independently optionally substituted with one or more $R_{15}$; and wherein the alkyl, alkenyl, and alkynyl are each independently optionally substituted with one or more substituents selected from halogen and —OH;

each $R_{15}$ is independently at each occurrence halogen, alkyl, CN, —C(═O)alkyl, or —C(═O)alkenyl, wherein the alkyl and alkenyl is each independently substituted with one or more substituents selected from halogen and —OH;

m is 1, 2, or 3; and n is 0 or 1;

provided that:

(i) if $R_2$ is $—NO_2$, —NHC(O)Me or $—NH_2$, and $R_1$, $R_2$, and $R_4$ are each H; or $R_1$ is Me and $R_2$, $R_3$, and $R_4$ are each H; then $R_6$ is not $—C(O)R_{10}$ where $R_{10}$ is $—(CH_2)—(CHMe)$-phenyl;

(ii) when $R_2$ is Cl, $R_1$, $R_3$ and $R_4$ are each H, $R_6$ is $—C(═O)R_{10}$, and $R_{10}$ is $(C_2-C_3)$alkyl substituted with one $R_{13}$; then $R_{13}$ is not unsubstituted cyclopentyl, unsubstituted phenyl or unsubstituted 2-thiophenyl; and (iii) when $R_2$ is Cl, and $R_1$, $R_3$ and $R_4$ are each H; then $R_6$ is $—C(═O)R_{10}$, $R_{10}$ is not 1-ethylpropyl.

In certain embodiments, the present invention provides a pharmaceutical composition suitable for use in a subject in the treatment or prevention of a disorder associated with modulation of USP7 comprising an effective amount of any of the compounds described herein (e.g., a compound of the invention, such as a compound of formula (I)), and one or more pharmaceutically acceptable excipients. In certain embodiments, the pharmaceutical preparations may be for use in treating or preventing a condition or disease as described herein.

Disclosed herein are methods of inhibiting USP7, comprising administering to a subject a therapeutically effective amount of a compound of Formula (I), or a pharmaceutically acceptable salt thereof.

Disclosed herein are methods of treating diseases and conditions that benefit from the modulation of USP7, comprising administering to a subject a therapeutically effective amount of a compound of Formula (I), or a pharmaceutically acceptable salt thereof. In some embodiments, the diseases and conditions benefit from the inhibition of USP7. These diseases and conditions include, but are not limited to, cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

Disclosed herein are methods of treating cancer, comprising administering to a subject a therapeutically effective amount of a compound of Formula (I), or a pharmaceutically acceptable salt thereof. In some embodiments, the cancer is multiple myeloma.

Disclosed herein is a compound of Formula (I), or a pharmaceutically acceptable salt thereof, for use in the manufacture of a medicament for treating a disease or condition associated with inhibiting USP7.

Disclosed herein is the use of a compound of Formula (I), or a pharmaceutically acceptable salt thereof, in the treatment of a disease or condition associated with inhibiting USP7.

DETAILED DESCRIPTION

Figure 1A:
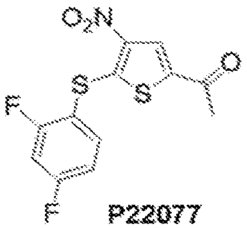
FIG. 1A: Known compound P22077 and its close analog P5091.
Figure 1A:
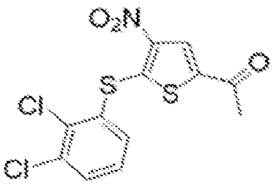

Disclosed herein are compounds of Formula (I):

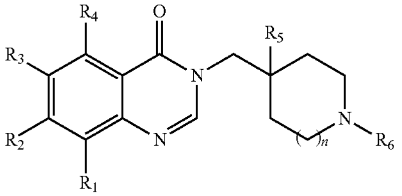

(I)

or a pharmaceutically acceptable salt thereof, wherein:

$R_1$ is H, halogen, alkyl, haloalkyl, alkoxy, haloalkoxy, —OH, —$NO_2$, —$NH_2$, CN, —$NR_7C$(═O)alkyl, —C(═O)$NR_7$alkyl, or —$NR_7R_8$, wherein each alkyl is independently optionally substituted with one or more $R_9$;

$R_2$ is H, halogen, alkyl, haloalkyl, alkoxy, haloalkoxy, —OH, —$NH_2$, —$NO_2$, CN, —$NR_7C$(═O)alkyl, —C(═O)$NR_7$alkyl, or —$NR_7R_8$, wherein each alkyl is independently optionally substituted with one or more $R_9$;

$R_3$ is H, halogen, alkyl, haloalkyl, alkoxy, haloalkoxy, —OH, —$NH_2$, —$NO_2$, CN, —$NR_7C$(═O)alkyl, —C(═O)$NR_7$alkyl, or —$NR_7R_8$; wherein each alkyl is independently optionally substituted with one or more $R_9$;

$R_4$ is H, halogen, alkyl, haloalkyl, alkoxy, haloalkoxy, —OH, —$NO_2$, —$NH_2$, CN, —$NR_7C$(═O)alkyl, —C(═O)$NR_7$alkyl, or —$NR_7R_8$; wherein each alkyl is independently optionally substituted with one or more $R_9$; wherein $R_1$, $R_2$, $R_3$ and $R_4$ are not simultaneously H;

$R_5$ is H, halogen, —CN, —$OR_7$, or —$NR_7R_8$;

$R_6$ is alkyl, —C(═O)$R_{10}$, —C(═S)$R_{10}$, —C(O)$NR_7R_8$, cycloalkyl, heterocycloalkyl, aryl, or heteroaryl; wherein the cycloalkyl, heterocycloalkyl, aryl, heteroaryl are each independently optionally substituted with one or more $R_{11}$; and wherein the alkyl is substituted with one or more $R_{12}$;

each $R_7$ and $R_8$ is independently H, alkenyl, or alkyl;

each $R_9$ is independently at each occurrence —$NR_7R_8$, alkoxy, —$(OCH_2CH_2)_m$alkyl, cycloalkyl, heterocycloalkyl, aryl, or heteroaryl, wherein the alkyl and alkoxy are each independently optionally substituted with one or more substituents selected from alkoxy, haloalkoxy, halogen, and —OH; and wherein the cycloalkyl, heterocycloalkyl, aryl and heteroaryl are each independently optionally substituted with one or more substituents selected from alkyl, haloalkyl, alkoxy, haloalkoxy, halogen, —$N_3$, and —OH;

$R_{10}$ is alkyl, alkenyl, alkynyl, —$NR_7R_8$, cycloalkyl, heterocycloalkyl, aryl, amino, heteroalkyl, alkylamino, aminoalkyl or heteroaryl, wherein the alkyl, alkenyl, and alkynyl are each independently optionally substituted with one or more $R_{13}$; and wherein the cycloalkyl, heterocycloalkyl, aryl and heteroaryl are each independently optionally substituted with one or more $R_{12}$;

each $R_{11}$ is independently at each occurrence alkyl, haloalkyl, alkoxy, haloalkoxy, halogen, —$NO_2$, or —OH;

each $R_{12}$ is independently at each occurrence aryl or heteroaryl, wherein the aryl and heteroaryl are each independently optionally substituted with one or more substituents selected from alkyl, haloalkyl, alkoxy, haloalkoxy, halogen, and —OH;

each $R_{13}$ is independently at each occurrence —OH, alkoxy, heteroalkyl, aryloxy, —$NH_2$, arylalkyl, cycloalkyl, heterocycloalkyl, aryl, heteroaryl, —O-aryl, —O-heteroaryl, —$NR_7$aryl, —$NR_7$heteroaryl, or —$NR_7C$(═O)$R_{14}$, wherein the cycloalkyl, heterocycloalkyl, aryl, heteroalkyl, and heteroaryl are each independently optionally substituted with one or more substituents selected from alkyl, haloalkyl, alkoxy, haloalkoxy, halogen, —$NO_2$, and —OH;

$R_{14}$ is alkyl, haloalkyl, arylalkyl, alkenyl, alkynyl, cycloalkyl, aryl, heterocyclyl, or heteroaryl, wherein the aryl and heteroaryl are each independently optionally substituted with one or more $R_{15}$; and wherein the alkyl, alkenyl, and alkynyl are each independently optionally substituted with one or more substituents selected from halogen and —OH;

each $R_{15}$ is independently at each occurrence halogen, alkyl, CN, —C(═O)alkyl, or —C(═O)alkenyl, wherein the alkyl and alkenyl is each independently substituted with one or more substituents selected from halogen and —OH;

m is 1, 2, or 3; and n is 0 or 1;

provided that:

(i) if $R_2$ is —$NO_2$, —NHC(O)Me or —$NH_2$, and $R_1$, $R_2$, and $R_4$ are each H; or $R_1$ is Me and $R_2$, $R_3$, and $R_4$ are each H; then $R_6$ is not —C(O)$R_{10}$ where $R_{10}$ is —$(CH_2)$—(CHMe)-phenyl;

(ii) when $R_2$ is Cl, $R_1$, $R_3$ and $R_4$ are each H, $R_6$ is —C(═O)$R_{10}$, and $R_{10}$ is $(C_2$-$C_3)$alkyl substituted with one $R_{13}$; then $R_{13}$ is not unsubstituted cyclopentyl, unsubstituted phenyl or unsubstituted 2-thiophenyl; and (iii) when $R_2$ is Cl, and $R_1$, $R_3$ and $R_4$ are each H; then $R_6$ is —C(=O)$R_{10}$, $R_{10}$ is not 1-ethylpropyl.

In some embodiments, the compound is a compound of Formula (Id):

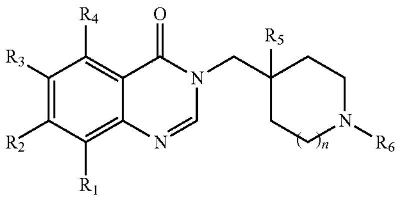

(Id)

or a pharmaceutically acceptable salt thereof, wherein:

$R_1$ is H, halogen, alkyl, haloalkyl, alkoxy, haloalkoxy, —OH, —$NO_2$, —$NH_2$, CN, —$NR_7$C(=O)alkyl, —C(=O)$NR_7$alkyl, or —$NR_7R_8$, wherein each alkyl is independently optionally substituted with one or more $R_9$;

$R_2$ is H, halogen, alkyl, haloalkyl, alkoxy, haloalkoxy, —OH, —$NH_2$, —$NO_2$, CN, —$NR_7$C(=O)alkyl, —C(=O)$NR_7$alkyl, or —$NR_7R_8$, wherein each alkyl is independently optionally substituted with one or more $R_9$;

$R_3$ is H, halogen, alkyl, haloalkyl, alkoxy, haloalkoxy, —OH, —$NH_2$, —$NO_2$, CN, —$NR_7$C(=O)alkyl, —C(=O)$NR_7$alkyl, or —$NR_7R_8$; wherein each alkyl is independently optionally substituted with one or more $R_9$;

$R_4$ is H, halogen, alkyl, haloalkyl, alkoxy, haloalkoxy, —OH, —$NO_2$, —$NH_2$, CN, —$NR_7$C(=O)alkyl, —C(=O)$NR_7$alkyl, or —$NR_7R_8$; wherein each alkyl is independently optionally substituted with one or more $R_9$; wherein $R_1$, $R_2$, $R_3$ and $R_4$ are not simultaneously H;

$R_5$ is H, halogen, —CN, —$OR_7$, or —$NR_7R_8$;

$R_6$ is alkyl, —C(=O)$R_{10}$, —C(=S)$R_{10}$, —C(O)$NR_7R_8$, cycloalkyl, heterocycloalkyl, aryl, or heteroaryl, wherein the cycloalkyl, heterocycloalkyl, aryl, heteroaryl are each independently optionally substituted with one or more $R_{11}$; and wherein the alkyl is substituted with one or more $R_{12}$;

each $R_7$ and $R_8$ is independently H or alkyl;

each $R_9$ is independently at each occurrence —$NR_7R_8$, alkoxy, —$(OCH_2CH_2)_m$alkyl, cycloalkyl, heterocycloalkyl, aryl, or heteroaryl, wherein the alkyl and alkoxy are each independently optionally substituted with one or more substituents selected from alkoxy, haloalkoxy, halogen, and —OH; and wherein the cycloalkyl, heterocycloalkyl, aryl and heteroaryl are each independently optionally substituted with one or more substituents selected from alkyl, haloalkyl, alkoxy, haloalkoxy, halogen, —$N_3$, and —OH;

$R_{10}$ is alkyl, alkenyl, alkynyl, —$NR_7R_8$, cycloalkyl, heterocycloalkyl, aryl, or heteroaryl, wherein the alkyl, alkenyl, and alkynyl are each independently optionally substituted with one or more $R_{13}$; and wherein the cycloalkyl, heterocycloalkyl, aryl and heteroaryl are each independently optionally substituted with one or more $R_{12}$;

each $R_{11}$ is independently at each occurrence alkyl, haloalkyl, alkoxy, haloalkoxy, halogen, —$NO_2$, or —OH;

each $R_{12}$ is independently at each occurrence aryl or heteroaryl, wherein the aryl and heteroaryl are each independently optionally substituted with one or more substituents selected from alkyl, haloalkyl, alkoxy, haloalkoxy, halogen, and —OH;

each $R_{13}$ is independently at each occurrence —OH, alkoxy, aryloxy, —$NH_2$, arylalkyl, cycloalkyl, heterocycloalkyl, aryl, heteroaryl, —O-aryl, —O-heteroaryl, —$NR_7$aryl, —$NR_7$heteroaryl, or —$NR_7$C(=O)$R_{14}$, wherein the cycloalkyl, heterocycloalkyl, aryl, and heteroaryl are each independently optionally substituted with one or more substituents selected from alkyl, haloalkyl, alkoxy, haloalkoxy, halogen, —$NO_2$, and —OH;

$R_{14}$ is alkyl, haloalkyl, arylalkyl, alkenyl, alkynyl, cycloalkyl, aryl, heterocyclyl, or heteroaryl, wherein the aryl and heteroaryl are each independently optionally substituted with one or more $R_{15}$; and wherein the alkyl, alkenyl, and alkynyl are each independently optionally substituted with one or more substituents selected from halogen and —OH;

each $R_{15}$ is independently at each occurrence halogen, alkyl, CN, —C(=O)alkyl, or —C(=O)alkenyl, wherein the alkyl and alkenyl is each independently substituted with one or more substituents selected from halogen and —OH;

m is 1, 2, or 3; and n is 0 or 1;

provided that:

(i) if $R_2$ is —$NO_2$, —NHC(O)Me or —$NH_2$, and $R_1$, $R_2$, and $R_4$ are each H; or $R_1$ is Me and $R_2$, $R_3$, and $R_4$ are each H; then $R_6$ is not —C(O)$R_{10}$ where $R_{10}$ is —$(CH_2)$—(CHMe)-phenyl;

(ii) when $R_2$ is Cl, $R_1$, $R_3$ and $R_4$ are each H, $R_6$ is —C(=O)$R_{10}$, and $R_{10}$ is ($C_2$-$C_3$)alkyl substituted with one $R_{13}$; then $R_{13}$ is not unsubstituted cyclopentyl, unsubstituted phenyl or unsubstituted 2-thiophenyl; and (iii) when $R_2$ is Cl, and $R_1$, $R_3$ and $R_4$ are each H; then $R_6$ is —C(=O)$R_{10}$, $R_{10}$ is not 1-ethylpropyl.

In some embodiments, $R_1$ is H, —$NR_7$C(=O)alkyl, or —$NR_7R_8$. In certain embodiments, $R_1$ is H. In some embodiments, $R_3$ is H, —$NO_2$, or —$NR_7R_8$. In certain embodiments, $R_3$ is H. In some embodiments, $R_4$ is H. In some embodiments, each $R_9$ is independently at each occurrence —$NR_7R_8$, alkoxy, —$(OCH_2CH_2)_m$alkyl, heterocycloalkyl, or heteroaryl, wherein the heterocycloalkyl or heteroaryl are each independently optionally substituted with one or more substituents selected from alkyl, alkoxy, and —$N_3$. In some embodiments, n is 0, while in other embodiments, n is 1. In some embodiments, $R_9$ is heterocycloalkyl or heteroaryl. In some embodiments, $R_9$ is N-methylpiperazinyl, piperidinyl, or morpholinyl. In some embodiments, $R_9$ is imidazolyl. In some embodiments, $R_9$ is azido. In some embodiments, $R_9$ is —$NR_7$H. In some embodiments, $R_7$ is acyl, alkylacy, or alkenylacyl. In some embodiments, $R_7$ is

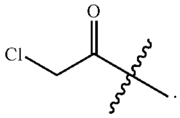 [SMILES: *C(=O)CCl]

In some embodiments, $R_2$ is selected from halogen, —$NH_2$, —$NO_2$, CN, —$NR_7$C(=O)alkyl and —C(=O)$NR_7$alkyl, wherein each alkyl is independently optionally substituted with one or more $R_9$. In certain embodiments, $R_2$ is halo, such as chloro, fluoro or bromo. In some embodiments, $R_2$ is chloro. In some embodiments, $R_2$ is —$NR_7C$(═O)alkyl or —C(═O)$NR_7$alkyl, and the alkyl is substituted with one $R_9$. In some embodiments, $R_2$ is nitro or —NHalkyl.

In some embodiments, $R_5$ is H, CN, —OH, or —$NR_7R_8$. In other embodiments, $R_5$ is —OH, or —$NR_7R_8$. In certain embodiments, $R_5$ is —OH, —$NH_2$, —N(H)$CH_3$ or —$N(CH_3)_2$. In some embodiments, $R_5$ is —OH.

In some embodiments, $R_6$ is alkyl, —C(═O)$R_{10}$, —C(═S)$R_{10}$, aryl, or heteroaryl. In some embodiments, $R_6$ is —C(═O)$R_{10}$. In certain embodiments, $R_{10}$ is alkyl, alkenyl, alkynyl, —$NR_7R_8$, cycloalkyl, or heterocycloalkyl, each optionally substituted with one or more $R_{13}$. In other embodiments, $R_{13}$ is independently at each occurrence —OH, alkoxy, aryloxy, —$NH_2$, arylalkyl, cycloalkyl, aryl, heteroaryl, or —$NR_7C$(═O)$R_{14}$. In some embodiments, $R_{14}$ is independently at each occurrence alkyl, haloalkyl, arylalkyl, alkenyl, heterocyclyl, or heteroaryl.

In some embodiments, $R_{10}$ is alkyl, alkenyl, amino, alkylamino, alkynyl, cycloalkyl, cycloalkyl, alkylamino, heteroaryl, or aminoalkyl. In some embodiments, the alkyl, amino, alkylamino, or cycloalkyl is substituted with aryl, aralkyl, heteroaryl, heterocyclyl, acylamino, aryloxy, or hydroxyl. In some embodiments, the aryl or heteroaryl is further substituted with alkyl, halo, alkyloxy, or nitro. In some embodiments, the aryl or heteroaryl is further substituted with halo, alkyloxy, or nitro. In some embodiments, the acylamino is substituted with halo, alkenyl, heteroaryl, or heterocycloalkyl. In some embodiments, the heteroaryl or heterocycloalkyl is substituted with alkylacyl, alkenylacyl, or hydroxyl.

In some embodiments, $R_2$ is Cl, —$NO_2$, —$NH_2$ or —$NR_7C$(═O)alkyl, wherein the alkyl is optionally substituted with one or more $R_9$; $R_6$ is —C(═O)$R_{10}$; and $R_{10}$ is alkyl, alkenyl, alkynyl, cycloalkyl, and heterocycloalkyl, wherein the alkyl, alkenyl, and alkynyl are each optionally substituted with one or more $R_{13}$; and wherein the cycloalkyl and heterocycloalkyl are each optionally substituted with one or more $R_{12}$ Also disclosed herein are compounds of Formula (Ib):

(Ib)

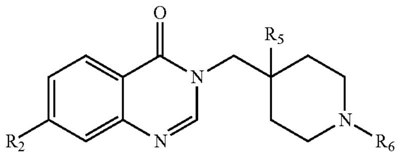

or a pharmaceutically acceptable salt thereof, wherein $R_2$, $R_5$ and $R_6$ are as defined above and herein.

Also disclosed herein are compounds of Formula (Ic):

(Ic)

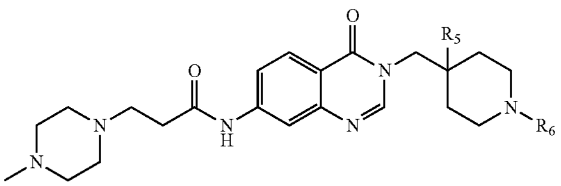

or a pharmaceutically acceptable salt thereof, wherein variables $R_5$ and $R_6$ are as described above and herein.

In some embodiments, the compound of the invention is a compound depicted in Table 3 or 4.

In certain embodiments, the present invention provides a pharmaceutical preparation suitable for use in a human patient, comprising any of the compounds shown above (e.g., a compound of the invention, such as a compound of formula (I), and one or more pharmaceutically acceptable excipients. In certain embodiments, the pharmaceutical preparations may be for use in treating or preventing a condition or disease as described herein. Any of the disclosed compounds may be used in the manufacture of medicaments for the treatment of any diseases or conditions disclosed herein.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive. Unless specifically stated or obvious from context, as used herein, the terms "a", "an", and "the" are understood to be singular or plural.

The term "and/or" is used in this disclosure to mean either "and" or "or" unless indicated otherwise.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive.

For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like. Exemplary substituted alkyls are described below. Cycloalkyls can be further substituted with alkyls, alkenyls, alkoxys, alkylthios, aminoalkyls, carbonyl-substituted alkyls, —CF3, —CN, and the like.

The term "Cx-y" when used in conjunction with a chemical moiety, such as, acyl, acyloxy, alkyl, alkenyl, alkynyl, or alkoxy is meant to include groups that contain from x to y carbons in the chain. For example, the term "Cx-yalkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. C0 alkyl indicates a hydrogen where the group is in a terminal position, a bond if internal. The terms "C2-yalkenyl" and "C2-yalkynyl" refer to substituted or unsubstituted unsaturated aliphatic groups analogous in length and possible substitution to the alkyls described above, but that contain at least one double or triple bond respectively.

The term "heteroalkyl", as used herein, refers to a saturated or unsaturated chain of carbon atoms and at least one heteroatom, wherein no two heteroatoms are adjacent.

Moreover, the term "heteroalkyl" (or "lower heteroalkyl") as used throughout the specification, examples, and claims is intended to include both "unsubstituted heteroalkyl" and "substituted heteroalkyls", the latter of which refers to heteroalkyl moieties having substituents replacing a hydrogen on one or more carbons or heteroatoms of the backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the heteroalkyl chain can themselves be substituted, if appropriate. For instance, the substituents of a substituted heteroalkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

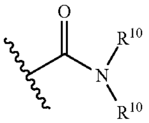

wherein each $R^{10}$ independently represents a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

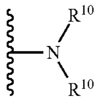
or
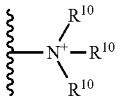

wherein each $R^{10}$ independently represents a hydrogen or a hydrocarbyl group, or two $R^{10}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

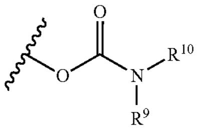
or
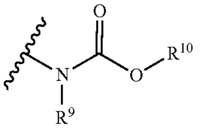

wherein R9 and R10 independently represent hydrogen or a hydrocarbyl group, such as an alkyl group, or R9 and R10 taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic.

Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO2-R10, wherein R10 represents a hydrocarbyl group.

The term "carboxy", as used herein, refers to a group represented by the formula —CO2H.

The term "ester", as used herein, refers to a group —C(O)OR10 wherein R10 represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO3H, or a pharmaceutically acceptable salt thereof.

The term "sulfonamide" is art-recognized and refers to the group represented by the general formulae

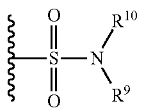

or

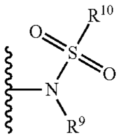

wherein R9 and R10 independently represents hydrogen or hydrocarbyl, such as alkyl, or R9 and R10 taken together with the intervening atom(s) complete a heterocycle having from 4 to 8 atoms in the ring structure.

The term "sulfoxide" is art-recognized and refers to the group —S(O)—R10, wherein R10 represents a hydrocarbyl.

The term "sulfonate" is art-recognized and refers to the group SO3H, or a pharmaceutically acceptable salt thereof.

The term "sulfone" is art-recognized and refers to the group —S(O)2-R10, wherein R10 represents a hydrocarbyl.

The term "thioalkyl", as used herein, refers to an alkyl group substituted with a thiol group.

The term "thioester", as used herein, refers to a group —C(O)SR10 or —SC(O)R10 wherein R10 represents a hydrocarbyl.

The term "thioether", as used herein, is equivalent to an ether, wherein the oxygen is replaced with a sulfur.

The term "urea" is art-recognized and may be represented by the general formula

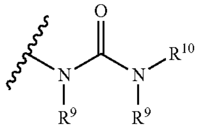

wherein R9 and R10 independently represent hydrogen or a hydrocarbyl, such as alkyl, or either occurrence of R9 taken together with R10 and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

The present invention includes all pharmaceutically acceptable isotopically-labelled compounds as described herein wherein one or more atoms are replaced by atoms having the same atomic number, but an atomic mass or mass number different from the atomic mass or mass number usually found in nature. In certain embodiments, compounds of the invention are enriched in such isotopically labeled substances (e.g., compounds wherein the distribution of isotopes in the compounds in the composition differ from a natural or typical distribution of isotopes).

Examples of isotopes suitable for inclusion in the compounds of the invention include isotopes of hydrogen, such as $^{2}H$ and $^{3}H$ carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds as disclosed herein, for example, those incorporating a radioactive isotope, are useful in drug and/or substrate tissue distribution studies. The radioactive isotopes tritium, i.e. $^{3}H$, and carbon-14, i.e. $^{14}C$, are useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron-emitting isotopes, such as $^{11}C$, $^{18}F$, $^{15}O$ and $^{13}N$, can be useful in Positron Emission Tomography (PET) studies for examining substrate receptor occupancy.

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric race mates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms.

Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. "Diastereomers" are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

Diastereomeric purity by weight is the ratio of the weight of one diastereomer or over the weight of all the diastereomers. When the stereochemistry of a disclosed compound is named or depicted by structure, the named or depicted stereoisomer is at least about 60%, about 70%, about 80%, about 90%, about 99% or about 99.9% by weight relative to the other stereoisomers. When a single enantiomer is named or depicted by structure, the depicted or named enantiomer is at least about 60%, about 70%, about 80%, about 90%, about 99% or about 99.9% by weight optically pure. When a single diastereomer is named or depicted by structure, the depicted or named diastereomer is at least about 60%, about 70%, about 80%, about 90%, about 99% or about 99.9% by weight pure. Percent optical purity is the ratio of the weight of the enantiomer or over the weight of the enantiomer plus the weight of its optical isomer.

Percent purity by mole fraction is the ratio of the moles of the enantiomer (or diastereomer) or over the moles of the enantiomer (or diastereomer) plus the moles of its optical isomer. When the stereochemistry of a disclosed compound is named or depicted by structure, the named or depicted stereoisomer is at least about 60%, about 70%, about 80%, about 90%, about 99% or about 99.9% by mole fraction pure relative to the other stereoisomers. When a single enantiomer is named or depicted by structure, the depicted or named enantiomer is at least about 60%, about 70%, about 80%, about 90%, about 99% or about 99.9% by mole fraction pure. When a single diastereomer is named or depicted by structure, the depicted or named diastereomer is at least about 60%, about 70%, about 80%, about 90%, about 99% or about 99.9% by mole fraction pure.

When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

As used herein, the term "pharmaceutically acceptable salt" means any pharmaceutically acceptable salt of the compound of formula (I). For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

In treatment, the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

Methods of Use

Ubiquitin is a 76-amino acid protein attached to substrate proteins post-translationally via iso-peptide bond formation between ubiquitin's C-terminal glycine and a substrate lysine sidechain; linear and branched polyubiquitin chains are assembled via attachment of another molecule of ubiquitin to one of seven lysines or the N-terminal methionine of ubiquitin. (Pickart and Fushman, Curr Opin Chem Biol, 8, 610-6, 2004) Ubiquitin is attached to substrate proteins by the coordinated action of ubiquitin activating (E1), conjugating (E2), and ligating (E3) enzymes and removed by a family of proteases known as deubiquitinating enzymes (DUBs). The first recognized role of the ubiquitin system was controlling protein turnover. (Lecker et al., J Am Soc Nephrol, 17, 1807-19, 2006) Ubiquitin tags are also responsible for signaling a wide range of non-degradative functions. (O'Neill, J Biol Chem, 284, 8209, 2009) Ubiquitination can affect protein activity by modulating conformational changes, complexation with other proteins, susceptibility to addition of other post-translation modifications (PTM) including phosphorylation and acetylation, and cellular localization. Through combined degradative and non-degradative functions, ubiquitination coordinates a wide range of cellular processes including proteolysis, DNA repair, chromatin remodeling, receptor signaling, and immunity, among others. (Pinto-Fernandez and Kessler, Front Genet, 7, 133, 2016) Not surprisingly, aberrant ubiquitin system activity is linked to disease, most heavily cancer, infection, and neurodegeneration. (D'Arcy et al., *Pharmacol Ther,* 147, 32-54, 2015; Atkin and Paulson, *Front Mol Neurosci,* 7, 63, 2014; Nanduri et al., *Curr Pharm Des,* 19, 3234-47, 2013) Deregulation of the ubiquitin-proteasome system has been implicated in the pathogenesis of many humandiseases, including cancer (Hoeller et al. *Nat Rev Cancer* 2006, 6(10), 776-788), neurodegenerative disorders (Rubinsztein, Nature 2006, 443(7113), 780-786) and viral diseases (Gao & Luo Can *J Physiol Pharmacol* 2006, 84(1), 5-14). The relationship between ubiquitin and cancer biology has been clinically validated by the FDA approval of the proteasome inhibitor bortezomib for multiple myeloma. (Kane et al., *Oncologist,* 8, 508-13, 2003)

There are approximately 100 human DUBs belonging to six distinct families. Five of the families [ubiquitin specific protease (USP), ubiquitin C-terminal hydrolase (UCH), Ovarian tumor protease (OTU), Josephin, and Mindy] are cysteine proteases and the sixth [JAB/MPN/MOV34 (JAMM/MPN)] is comprised of zinc metalloproteases. (Komander et al., *Nat Rev Mol Cell Biol,* 10, 550-63, 2009; Clague et al., *Physiol Rev,* 93, 1289-315, 2013; Abdul Rehman et al., *Mol Cell,* 63, 146-55, 2016) Many DUBs have been linked to physiological and/or pathophysiological functions. Ubiquitin specific proteases and ubiquitin C-terminal hydrolases (UCH) enzymes are the best characterized members of the DUB family (Komander et al. 2009; Nijman et al. *Cell* 2005, 123(5), 773-786). For example, USP1 and USP4 are involved in DNA damage repair. (Kee and Huang, *Mol Cell Biol,* 36, 524-44, 2015) USP22 and BAP1 have a role in chromatin function (Atanassov et al., *FEBS Lett,* 585, 2016-23, 2011), and USP2 and USP8 are reported to stabilize oncogenic proteins cyclin D1, (Shan et al., 2009) and mutant EGFR, (Byun et al., *Clin Cancer Res,* 19, 3894-904, 2013) respectively. X-ray crystal structures of the catalytic core of each family reveal that all except the Mindy family adopt a common fold comprised of three domains: the fingers domain coordinates the ubiquitin core, and the thumb and palm coordinates the ubiquitin tail at the catalytic triad-containing active site. (Komander et al., 2009) While dozens of apo- and ubiquitin-bound structures have been solved, very few have been achieved with non-ubiquitin-based compounds. Notably, there are no reported small molecule DUB complex structures for the largest 56-member mammalian USP family. (Komander et al., 2009), (Davies et al., *Bioorg Med Chem Lett,* 22, 3900-4, 2012; Ratia et al., *Proc Natl Acad Sci USA,* 105, 16119-24, 2008; Schlierf et al., *Nat Commun,* 7, 13166, 2016)

Although DUBs are generally regarded as a targetable class for drug development, inhibitor development is still in early stages. The first DUB inhibitor, the dual USP14/UCHL5 inhibitor VLX1570, entered clinical trials in 2015. (Wang et al., *Sci Rep,* 6, 26979, 2016b) The only example of structure-guided development of a DUB inhibitor, which targeted the SARs DUB PLPro (Baez-Santos et al., *Antiviral Res,* 115, 21-38, 2015), generated compounds with $IC_{50}$s below 500 nM and exhibiting a high degree of selectivity relative to mammalian DUBs. In this case, selectivity may result from significant structural differences between viral and mammalian DUBs. There are, however, no reported examples of structure-guided optimization of a mammalian DUB. However, breakthroughs in X-ray crystallography of small molecule DUB inhibitor complexes has the potential to enable rapid development of potent and selective inhibitors.

USP7 (Ubiquitin Specific Protease 7)/HAUSP (Herpes Associated Ubiquitin Specific Protease) is a 135 kDa protein of the USP family. USP7 has been shown to interact with viral proteins, such as ICPO (Vmw 110), a herpes simplex virus immediate-early gene stimulating initiation of the viral lytic cycle (Everett et al., *J Virol* 73, 1999, 417-426), and EBNA1 (Epstein-Barr Nuclear Antigen-1) (Holowaty et al., *J Biol Chem* 2003, 278, 29987-29994 and 47753-47761). The DUB USP7 has been shown to be involved in regulation of a myriad of cellular processes, including epigenetics, cell cycle, DNA repair, immunity, viral infection and tumorigenesis. Interest in the enzyme intensified when USP7 was implicated in regulating degradation of the tumor suppressor p53 (Li et al., *Nature,* 416, 648-53, 2002), by stabilizing the major E3 ligase for p53, MDM2. (Cummins et al., *Nature,* 428, 1 p following 486, 2004, Li et al., *Mol Cell,* 13, 879-86, 2004). Consistent with recent reports, USP7 silencing has also been shown to increase steady-state p53 levels by promoting Mdm2 degradation. Binding of USP7 to p53 was recently shown to be regulated by TSPYL5, a protein potentially involved in breast oncogenesis through a competition with p53 for binding to the same region of USP7. (Epping et al., *Nat Cell Biol.* 2011, 13(1):102-8) More recently, both upregulation and downregulation of USP7 have been shown to inhibit colon cancer cell proliferation in vitro and tumor growth in vivo, by resulting in constitutively high p53 levels (Becker et al. *Cell Cycle* 2008, 7(9), 1205-13).

USP7 also alters the level of the $p16_{INK4a}$ tumor suppressor through Bmi1/Mel18 stabilization (Maertens et al., *Embo J.* 2010 29, 2553-2565). Additional proteins involved in genomic integrity/regulation such as the DNMT1 DNA methylase and the Claspin adaptor are also stabilized by USP7 (Du et al., *Science Signaling* 2010, 3(146):ra80; Faustrup et al., *J. Cell Biol.* 2009,184(1):13-9). Importantly, the abundance of USP7 and DNMT1, a protein involved in maintaining epigenetic methylation required to silence genes involved in development and cancer, correlates in human colon cancer (Du et al., 2010). USP7 has also been shown in human cells to deubiquitinate the well-known tumor suppressor gene PTEN, which provokes its nuclear export and hence its inactivation (Song et al., *Nature* 2008, 455(7214), 813-7). More importantly, USP7 overexpression was reported for the first time in prostate cancer and this overexpression was directly associated with tumour aggressiveness (Song et al., Nature 2008, 455(7214), 813-7).

Recently, several epigenetic modifiers, including the methytransferase PHF8, (Wang et al., 2016a) demethylase DNMT1, (Du et al., 2010, Felle et al., *Nucleic Acids Res,* 39, 8355-65, 2011, Qin et al., *J Cell Biochem,* 112, 439-44, 2011) and acetyltransferase Tip60, (Dar et al., *Mol Cell Biol,* 33, 3309-20, 2013) as well as H2B itself, (van der Knaap et al., *Mol Cell,* 17, 695-707, 2005) have been identified as direct targets of USP7. Other notable targets of USP7 include the transcription factors FOXP3, which in Treg cells links this DUB enzyme to immune response, (van Loosdregt et al., *Immunity,* 39, 259-71, 2013) and N-Myc, which is stabilized in neuroblastoma cells. (Tavana et al., *Nat Med,* 22, 1180-1186, 2016) Consistent with its regulation of diverse substrates and biological processes USP7 has emerged as a drug target in a wide range of malignancies including multiple myeloma, (Chauhan et al., *Cancer Cell,* 22, 345-58, 2012) breast cancer, (Wang et al., 2016a) neuroblastoma, (Tavana et al., 2016) glioma, (Cheng et al., *Oncol Rep,* 29, 1730-6, 2013) and ovarian cancer. (Zhang et al., *Tohoku J Exp Med,* 239, 165-75, 2016) USP7 has also been shown in human cells to deubiquitinate FOXO4, which provokes its nuclear export and hence its inactivation; consequently the oncogenic PI3K/PKB signaling pathway was activated (van der Horst et al., *Nat Cell Biol.* 2006, 8, 1064-1073) Finally, USP7 plays an important role in p53-mediated cellular responses to various types of stress, such as DNA damage and oxidative stress (Marchenko et al., *Embo J.* 2007 26, 923-934, Meulmeester et al., *Mol Cell* 2005, 18, 565-576., van der Horst et al., *Nat Cell Biol.* 2006, 8, 1064-1073).

Multiple myeloma (MMz) is an incurable hematological malignancy characterized by the accumulation of abnormal plasma cells in the bone marrow. which impede production of normal blood cells. the average survival of MM patients has improved in recent years as a result of the introduction of proteasome inhibitors and immunomodulatory agents into treatment regimens but is still quite poor at only 5 years. The proteasome inhibitor bortezomiib validates the ubiquitin proteasome system as a therapeutic target for MM drug development. USP7 is a therapeutic target in MM due to its role in the degradation of p53. USP7 is highly expressed in MM patient tumor cells and MM cell lines versus normal bone marrow cells. Mutations or deletions in p53 are late events in MM suggesting that increasing p53via pharmacological inhibition of USP7 could be an effective therapeutic strategy for this malignancy.

Figure 1B:
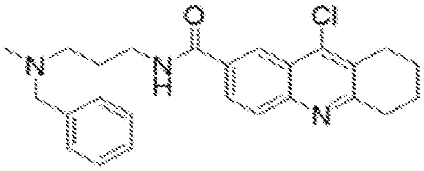
FIG. 1B: Known USP7 inhibitors.
Figure 1B:
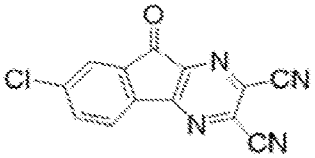
Figure 1B:
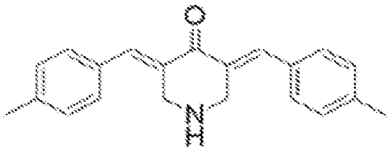
Figure 1B:
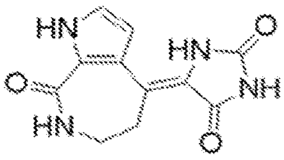
Figure 1B:
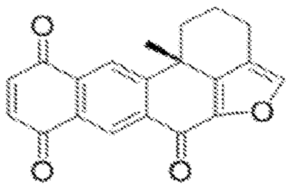
Figure 1B:
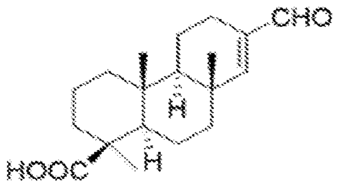

P22077 and its close analog P5091 (structures in FIG. 1A) are the inhibitors most frequently utilized to probe USP7 functions. P22077 exhibits modest potency against USP7 (IC50=8.0 μM) and equipotent inhibition of two additional DUBs, USP10 and USP47. (Altun et al., 2011, Ritorto et al., 2014) In addition to modest potency and selectivity, reported drawbacks of these nitro-thiophene-based compounds include poor solubility and general toxicity. (Chen et al., 2017) Additional USP7 inhibitors (shown in FIG. 1B) have been identified although none possess features superior to P5091/P22077 and significant optimization efforts have not been undertaken. (Reverdy et al., *Chem Biol,* 19, 467-77, 2012; Colland et al., *Mol Cancer Ther,* 8, 2286-95, 2009; Aleo et al., *Cancer Res,* 66, 9235-44, 2006; Nicholson et al., *Protein Sci,* 17, 1035-43, 2008, Yamaguchi et al., *Bioorg Med Chem Lett,* 23, 3884-6, 2013, Tanokashira et al., *Tetrahedron,* 72, 5530-5540, 2016.

Disclosed herein are methods for treating and preventing diseases and conditions that benefit from the modulation of USP7, comprising administering to a subject in need thereof a compound of Formula (I) or a pharmaceutically acceptable salt thereof.

Disclosed herein are methods for treating and preventing diseases and conditions that benefit from the inhibition of USP7, comprising administering to a subject in need thereof a compound of Formula (I) or a pharmaceutically acceptable salt thereof.

Disclosed herein are methods of inhibiting USP7, comprising administering to a subject in need thereof a compound of Formula (I) or a pharmaceutically acceptable salt thereof.

In certain embodiments, disclosed herein are methods of treating a disease or a disorder modulated by USP7 comprising administering to a subject in need thereof a compound of Formula (I) or a pharmaceutically acceptable salt thereof. In certain embodiments, disclosed herein are methods of preventing a disease or a disorder modulated by USP7 comprising administering to a subject in need thereof a compound of Formula (I) or a pharmaceutically acceptable salt thereof. In some embodiments, the modulation of USP7 involves inhibiting USP7.

In one embodiment, the disease or disorder is selected from cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

Disclosed herein is the use of an inhibitor of USP7 for the preparation of a medicament for treating or preventing a disease or condition modulated by USP7, wherein the medicament comprises a compound of Formula (I). In some embodiments, the modulation of USP7 involves inhibiting USP7.

Disclosed herein a compound of Formula (I) for use in treating a disease or condition modulated by USP7. In some embodiments, the modulation of USP7 involves inhibiting USP7.

Disclosed herein are methods of treating cancer comprising administering to a subject in need thereof a compound of Formula (I) or a pharmaceutically acceptable salt thereof.

In some embodiments, exemplary cancers include, but are not limited to, liposarcoma, neuroblastoma, glioblastoma, breast cancer, bladder cancer, glioma, neuroblastoma, adrenocortical cancer, multiple myeloma, colorectal cancer, non-small cell lung cancer, Human Papilloma Virus-associated cervical, oropharyngeal, penis, ovarian cancer, anal, thyroid or vaginal cancer or Epstein-Barr Virus-associated nasopharyngeal carcinoma, gastric cancer, rectal cancer, thyroid cancer, Hodgkin lymphoma or diffuse large B-cell lymphoma.

In some embodiments, the cancers are selected from multiple myeloma, breast cancer, neuroblastoma, glioma, colon cancer, prostate cancer, neuroblastoma, and ovarian cancer. In some embodiments, the cancer is breast cancer, glioma, neuroblastoma, multiple myeloma, or ovarian cancer. In some embodiments, the cancer is multiple myeloma.

Disclosed herein are methods of treating neurodegenerative diseases comprising administering to a subject in need thereof a compound of Formula (I) or a pharmaceutically acceptable salt thereof.

In some embodiments, neurodegenerative diseases include, but are not limited to, Alzheimer's disease, multiple sclerosis, Huntington's disease, infectious meningitis, encephalomyelitis, Parkinson's disease, amyotrophic lateral sclerosis, or encephalitis.

Pharmaceutical Compositions

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel. Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, about 5, about 20, about 50, about 75, about 100, about 150, about 250, about 500, about 750, about 1000, about 1250, about 2500, about 3500, or about 5000 mg of the disclosed compound, or, in a range of from one amount to another amount in the list of doses In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the invention with one or more additional therapeutic agent(s) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EXAMPLES

The compounds of Formula (I) may be prepared by methods known in the art of organic synthesis as set forth in part by the following synthetic schemes. The compounds described herein may be made from commercially available starting materials or synthesized using known organic, inorganic, and/or enzymatic processes.

In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994). A mixture of enantiomers, diastereomers, cis/trans isomers resulting from the process described above can be separated into their single components by chiral salt technique, chromatography using normal phase, reverse phase or chiral column, depending on the nature of the separation.

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. All commercially available starting materials were purchased from Sigma Aldrich, Fisher Scientific, Oakwood Chemical and Combi Block. All reagents were used as received without further purification. Known compounds were synthesized according to published literature procedures and any modifications are noted. Anhydrous solvents, such as tetrahydrofuran (THF), diethyl ether, dichloromethane (DCM), dimethyl formamide (DMF), dimethylsulfoxide (DMSO), 1,4-dioxane, and toluene (PhMe) were purchased from Fisher Scientific, and used as received. If necessary, air or moisture sensitive reactions were carried out under an inert atmosphere of nitrogen.

Removal of solvents was accomplished on a Buchi R-300 rotary evaporator and further concentration was done under a Welch 1400B-01 vacuum line, and Labconco FreeZone 6 plus system. Purification of compounds was performed by normal phase column chromatography using Teledyne CombiFlash chromatography system, and/or reversed phase chromatography on Waters Micromass ZQ preparative system with SunFire® Prep C18 OBDTM 5 μM column. The purity was analyzed on Waters Acquity UPLC system. Analytical thin layer chromatography (TLC) plates were purchased from Fisher Scientific (EMD Millipore TLC Silica Gel60 F254). Visualization was accomplished by irradiation under UV light (254 nm).

All 1H-NMR spectra were recorded at 298K on a Bruker ARX 500 (500 MHz) spectrometer. 13C-NMR spectra were recorded on a Bruker ARX 500 (126 MHz) spectrometer. Samples were dissolved in CDCl3, DMSO-d6, or CD3OD. The spectra were referenced to the residual solvent peak (chlorofrom-d: 7.26 ppm for 1H-NMR and 77.16 ppm for 13C-NMR; DMSO-d6: 2.50 ppm for 1H-NMR and 39.25 ppm for 13C-NMR, CD3OD: 3.31 ppm for 1H NMR and 49.00 ppm for 13C NMR or tetramethylsilane (TMS) as the internal standard. Chemical shift, multiplicity (s=singlet, d=doublet, t=triplet, q=quartet, m=multiplet, br-broad peak), coupling constants (Hz), and number of protons. Mass spectrometry (LCMS) data were obtained on Waters Acquity UPLC system in positive ESI mode.

Example 1: Exemplary Synthesis of Compounds of the Disclosure

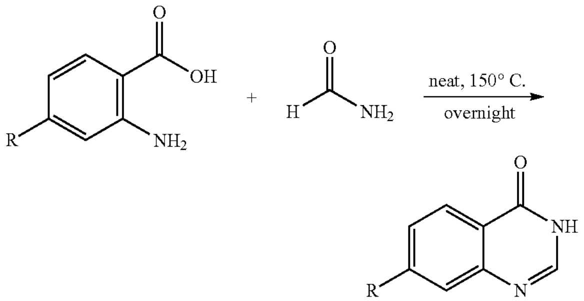

S1. R = Cl; S2. R = $NO_2$

2-Aminobenzoic acids (10.0 mmol) and formamide (1.8 g, 40.0 mmol) were mixed in pressure tube, which was heated at 150° C. overnight. Then the reaction was cooled to room temperature. The solid was suspended in cold water, then collected by vacuum filtration, and dried on high vacuum line. The products 1.6 g (—Cl) and 1.8 g (—$NO_2$) were isolated as light brown solid in 88% (—Cl) and 95% (—$NO_2$) yields with no further purification.

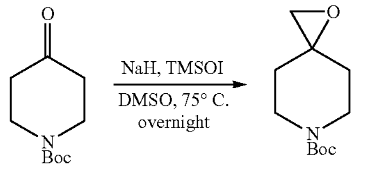

S3

Sodium hydride (60% dispersion in mineral oil) (0.88 g, 22.0 mmol) was dissolved in 40 mL anhydrous DMSO at 0° C. under $N_2$. Trimethylsulfoxonium iodide (4.84 g, 22.0 mmol) was added into the solution portionwise. When addition completed, the mixture was warmed up to room temperature, and stirred for 40 min. Then 1-Boc-4-piperidone (3.98 g, 20.0 mmol) was added portion wisely. The reaction mixture was then stirred at room temperature for 1 hour, then at 65° C. for another hour. Then the mixture was poured on 100 mL ice. Aqueous phase was extracted using EtOAc (50 mL×2). Combined organic phase was washed with brine, dried over $MgSO_4$, filtered, and evaporated under reduced pressure. The crude material was purified by flash column chromatography (50% EtOAc in hexanes) to afford 2.98 g product in 70% yield.

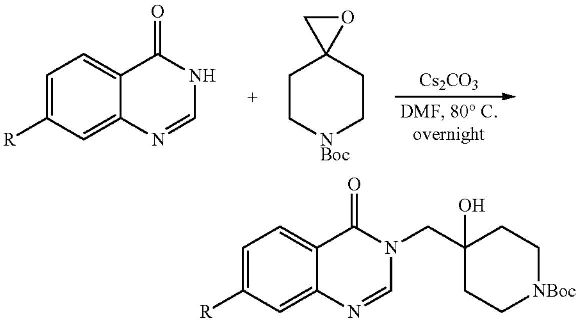

S4. R = Cl; S5. R = $NO_2$

Into the solution of S1 (2.13 g, 11.8 mmol) in 50 mL DMF was added S3 (2.78 g, 13.0 mmol) and $Cs_2CO_3$ (11.54 g, 35.4 mmol). The mixture was heated at 80° C. overnight. Then the reaction was cooled to room temperature, and diluted with EtOAc. The solution was washed with saturated $NH_4Cl$ (50 mL×2) Aqueous phase was extracted with more EtOAc. Combined organic phase was washed with brine, dried over MgSO4, followed by filtration and evaporation under reduced pressure. The crude material was purified by flash column chromatography (40% to 100% EtOAc in hexanes) to afford 3.94 g product in 85% yield.

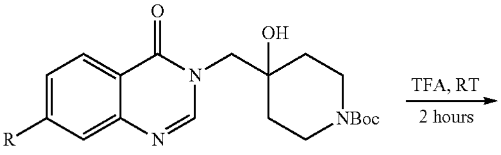

-continued

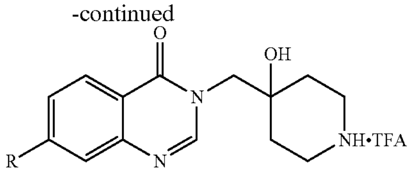

S4. R = Cl; S5. R = NO2; S6. R = Cl; S7. R = $NO_2$

S4 was taken up in trifluoroacetic acid (TFA) as 1M solution, which was stirred at room temperature for 2 hours. The solution was concentrated under reduced pressure, further on high-vac overnight. S6 was directly used as starting material for the following synthesis without further purification.

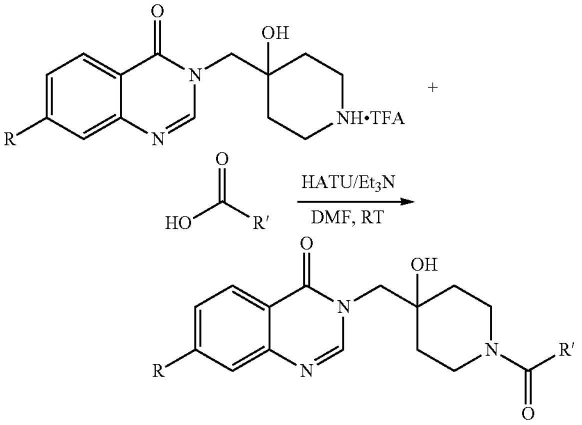

S6. R = Cl; S7. R = $NO_2$

Amide Formation by HATU-Catalyzed Coupling Reaction

S6 was taken up in DMF as 1M solution, and 3 equivalence of $Et_3N$ was added. The carboxylic acid (1.2 eq) was pre-mixed with HATU (2 eq) and $Et_3N$ (5 eq) in DMF at the same concentration, which was stirred at room temperature for 10 min. Two solutions were then mixed together and further stirred at room temperature for 5 hours. The reaction was directly subjected to prep. HPLC purification. The isolated product was then further purified by normal phase flash chromatography to afford product with desired purity for following biological tests.

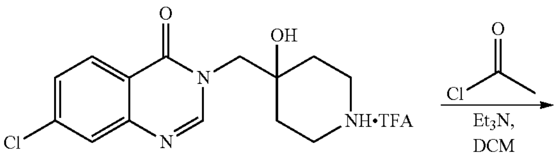

S6

-continued

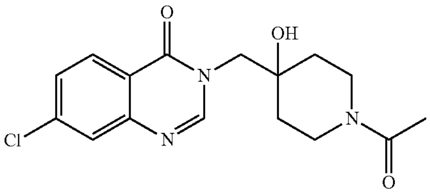

6

Amide Formation by Acylation Using Acid Chloride

S6 (0.04 g, 0.1 mmol) was taken up in 2 mL dichloromethane. $Et_3N$ (0.07 mL, 0.5 mmol) was added, followed by addition of acetyl chloride (0.015 mL, 0.2 mL). The reaction was kept at 0° C. stirring for 2 hours. Then the reaction was quenched by adding drops of water, followed by immediate purification by flash column chromatography. The isolated product 6 was further purified by HPLC to afford 19 mg product in 57% yield.

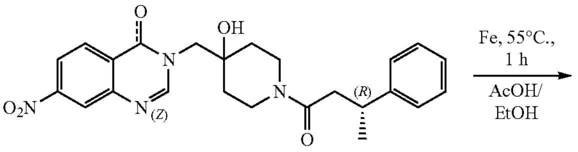

S7

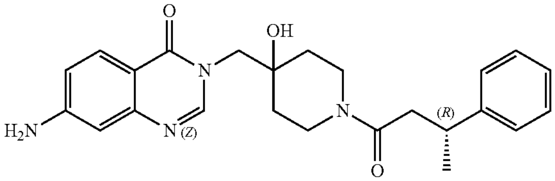

S8

Reduction of Aromatic Nitro Group

S7 (0.49 g, 1.08 mmol) was dissolved in 10 mL AcOH/EtOH (1:1). Iron powder (0.25 g, 4.39 mmol) was added in one portion. The reaction was then stirred at 50° C. for 1 hour. The iron powder was removed by filtration. Filtrate was concentrated under reduced pressure. The crude material was then purified by normal phase flash column chromatography (10% to 40% MeOH in EtOAc), followed by reverse phase HPLC to afford 0.22 g product S8 in 53% yield

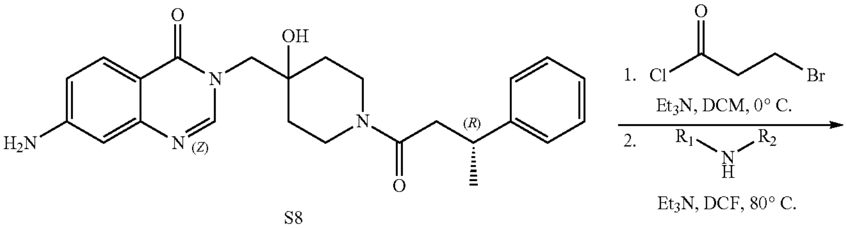

S8

Installation of solubilizing groups

-continued

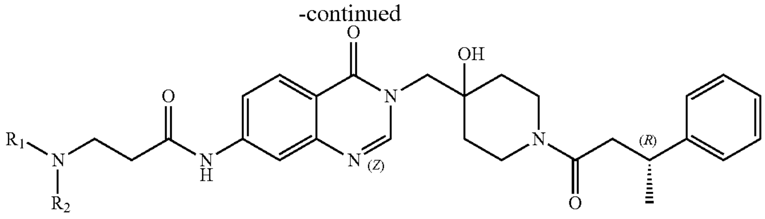

10: $R_1 + R_2$ = N-Me-piperazinyl

S8 (0.11 g, 0.25 mmol) was dissolved in 5 mL dichloromethane. $Et_3N$ (0.035 mL, 0.25 mmol) was added at −20° C.3-bromopropionyl chloride (0.03 mL, 0.25 mmol) in 1 mL DCM was added dropwisely. The reaction was stirred at 0° C. for 3 h. Then it was quenched by addition of drops of water, then concentrated under reduced pressure. The crude product was used for the next step without further purification.

Crude material from last step (0.06 g, 0.1 mmol) was dissolved in 1 mL DMF. Into the solution was added N-methylpiperazine (0.016 mL, 0.12 mmol) and $Et_3N$ (0.028 mL, 0.2 mmol). The reaction was stirred at 80° C. for 3 hours. The solution was directly subjected to reverse phase HPLC purification, followed by normal phase flash column chromatography (20% to 60% MeOH in EtOAc with 0.5% $Et_3N$) to afford 0.043 g product 10 in 75% yield.

Using these procedures and variations thereof, the following compounds were synthesized.

1

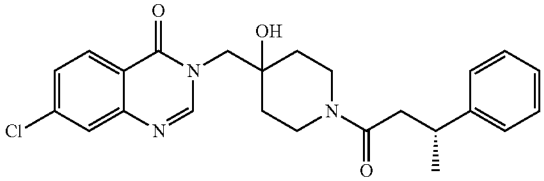

((R)-7-Chloro-3-((4-hydroxy-1-(3-phenylbutanoyl)piperidin-4-yl)methyl)quinazolin-4(3H)-one: white solid, 50% yield)$^1$H NMR (500 MHz, DMSO) δ 8.27 (d, J=12.8 Hz, 1H), 8.16 (d, J=8.6 Hz, 1H), 7.75 (d, J=1.7 Hz, 1H), 7.58 (dd, J=8.6, 2.0 Hz, 1H), 7.26 (dd, J=13.8, 6.7 Hz, 4H), 7.20-7.08 (m, 1H), 4.93 (d, J=5.9 Hz, 1H), 4.04 (d, J=13.6 Hz, 2H), 3.92 (q, J=13.9 Hz, 1H), 3.65 (t, J=12.5 Hz, 1H), 3.28-3.06 (m, 2H), 2.86 (ddd, J=13.9, 8.6, 3.2 Hz, 1H), 2.68-2.50 (m, 2H), 1.62-1.26 (m, 3H), 1.26-1.12 (m, 3H). $^{13}$C NMR (126 MHz, DMSO) δ 168.92, 159.90, 150.16, 148.76, 146.43, 146.31, 138.70, 128.22, 127.99, 127.96, 126.98, 126.68, 126.64, 125.99, 125.74, 125.69, 120.12, 69.05, 69.00, 53.58, 40.82, 40.71, 39.99, 36.68, 36.01, 35.78, 34.78, 34.65, 34.09, 33.95, 21.83, 21.63. LCMS (ESI) m/z 440.29 $[(M+H)^+]$; calcd for $C_{24}H_{27}ClN_3O_3^+$: 440.17].

2

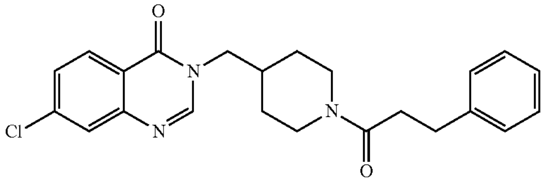

(7-Chloro-3-((1-(3-phenylpropanoyl)piperidin-4-yl)methyl)quinazolin-4(3H)-one: white solid, 33% yield)$^1$H NMR (500 MHz, $CDCl_3$) δ 8.21 (d, J=8.6 Hz, 1H), 7.93 (s, 1H), 7.70 (d, J=1.9 Hz, 1H), 7.46 (dd, J=8.6, 2.0 Hz, 1H), 7.31-7.25 (m, 2H), 7.22-7.18 (m, 3H), 4.69 (d, J=13.4 Hz, 1H), 3.88-3.73 (m, 3H), 3.00-2.92 (m, 2H), 2.91-2.82 (m, 1H), 2.60 (dp, J=14.3, 7.3 Hz, 2H), 2.48 (td, J=13.1, 2.4 Hz, 1H), 2.17-2.04 (m, 1H), 1.70 (d, J=12.9 Hz, 1H), 1.62 (d, J=12.8 Hz, 1H), 1.17 (qd, J=12.5, 4.3 Hz, 1H), 0.97 (qd, J=12.5, 4.2 Hz, 1H). $^{13}$C NMR (126 MHz, DMSO) δ 169.56, 159.76, 149.58, 148.95, 141.43, 138.88, 128.37, 128.18, 127.28, 126.30, 125.79, 120.37, 50.79, 44.55, 40.74, 38.22, 35.01, 33.98, 30.87, 29.54, 28.84. LCMS (ESI) m/z 410.29 $[(M+H)^+]$; calcd for $C_{23}H_{25}ClN_3O_2^+$: 410.16].

3

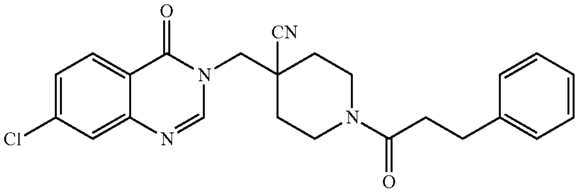

4-((7-Chloro-4-oxoquinazolin-3(4H)-yl)methyl)-1-(3-phenylpropanoyl)piperidine-4-carbonitrile: white solid, commercial compound)$^1$H NMR (500 MHz, DMSO) δ 8.44 (s, 1H), 8.17 (d, J=8.6 Hz, 1H), 7.79 (d, J=2.0 Hz, 1H), 7.62 (dd, J=8.6, 2.1 Hz, 1H), 7.25 (ddd, J=13.3, 7.9, 4.0 Hz, 4H), 7.20-7.12 (m, 1H), 4.46 (d, J=13.8 Hz, 1H), 4.36-4.24 (m, 2H), 3.97 (d, J=14.3 Hz, 1H), 3.05 (t, J=12.5 Hz, 1H), 2.80 (t, J=7.7 Hz, 2H), 2.73-2.57 (m, 3H), 1.88 (t, J=14.6 Hz, 2H), 1.61 (dtd, J=17.1, 13.0, 3.9 Hz, 2H). $^{13}$C NMR (126 MHz, DMSO) δ 170.41, 160.54, 149.90, 149.20, 141.81, 139.78, 128.99, 128.89, 128.70, 128.13, 126.94, 126.34, 121.06, 120.79, 50.64, 42.38, 40.40, 38.51, 34.30, 32.87, 32.28, 31.22. LCMS (ESI) m/z 435.29 $[(M+H)^+]$; calcd for $C_{24}H_{24}ClN_4O_2^+$: 435.16].

4

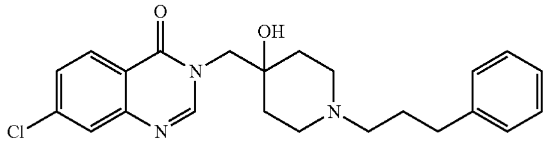

(7-Chloro-3-((4-hydroxy-1-(3-phenylpropyl)piperidin-4-yl)methyl)quinazolin-4(3H)-one: white solid, 13% yield)$^1$H NMR (500 MHz, MeOD) δ 8.29 (s, 1H), 8.21 (d, J=8.6 Hz, 1H), 7.69 (d, J=1.9 Hz, 1H), 7.54 (dd, J=8.6, 2.0 Hz, 1H), 7.26 (q, J=7.1 Hz, 2H), 7.21-7.13 (m, 3H), 4.11 (s, 2H), 2.97 (d, J=12.0 Hz, 2H), 2.76-2.59 (m, 6H), 1.98-1.81 (m, 4H), 1.63 (d, J=13.4 Hz, 2H). $^{13}C$ NMR (126 MHz, MeOD) δ 161.13, 149.97, 148.77, 140.38, 140.25, 128.24, 128.13, 128.00, 127.52, 126.00, 120.22, 67.60, 56.16, 53.81, 48.21, 32.27, 32.00, 25.90. LCMS (ESI) m/z 412.39 $[(M+H)^+$; calcd for $C_{23}H_{27}ClN_3O_2^+$: 412.18].

5

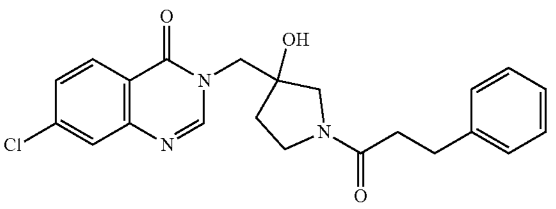

(7-chloro-3-((3-hydroxy-1-(3-phenylpropanoyl)pyrrolidin-3-yl)methyl)quinazolin-4(3H)-one: white solid, 8% yield)$^1$H NMR (500 MHz, DMSO) δ 8.29 (s, 1H), 8.17 (dd, J=8.6, 4.3 Hz, 1H), 7.76 (t, J=2.3 Hz, 1H), 7.59 (ddd, J=8.7, 7.5, 2.1 Hz, 1H), 7.29-7.19 (m, 4H), 7.16 (t, J=6.8 Hz, 1H), 5.27 (s, 1H), 4.17 (s, 1H), 4.14 (d, J=4.0 Hz, 1H), 3.51 (s, 2H), 3.32 (dt, J=23.6, 11.7 Hz, 3H), 2.84-2.74 (m, 2H), 2.59-2.51 (m, 2H), 2.47-2.40 (m, 1H), 1.95 (ddt, J=39.5, 12.7, 9.3 Hz, 1H), 1.76 (ddd, J=12.9, 11.0, 5.7 Hz, 1H). $^{13}C$ NMR (126 MHz, DMSO) δ 169.93, 169.76, 160.22, 160.13, 150.33, 149.06, 149.04, 141.55, 141.51, 138.95, 128.45, 128.40, 128.35, 128.22, 127.24, 126.27, 125.81, 120.46, 78.33, 76.84, 55.97, 55.57, 51.10, 50.87, 44.46, 43.77, 36.06, 35.63, 35.06, 34.54, 30.29, 30.23. LCMS (ESI) m/z 412.29 $[(M+H)^+$; calcd for $C_{22}H_{23}ClN_3O_3^+$: 412.14].

6

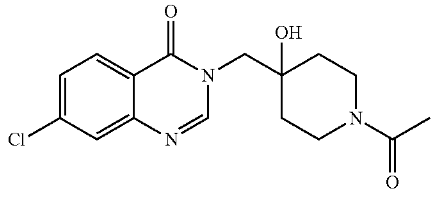

(3-((1-Acetyl-4-hydroxypiperidin-4-yl)methyl)-7-chloroquinazolin-4(3H)-one: white solid, 57% yield)$^1$H NMR (500 MHz, DMSO) δ 8.40 (s, 1H), 8.15 (d, J=8.6 Hz, 1H), 7.75 (d, J=2.0 Hz, 1H), 7.57 (dd, J=8.6, 2.1 Hz, 1H), 4.09-3.96 (m, 4H), 3.58 (d, J=13.4 Hz, 1H), 3.33-3.20 (m, 1H), 2.97-2.85 (m, 1H), 1.98 (s, 3H), 1.56 (td, J=13.3, 4.3 Hz, 1H), 1.49-1.34 (m, 3H). $^{13}C$ NMR (126 MHz, DMSO) δ 167.66, 159.89, 150.25, 148.62, 138.65, 128.19, 126.92, 125.88, 120.05, 68.98, 53.39, 41.40, 36.44, 34.61, 33.93, 20.98. LCMS (ESI) m/z 336.18 $[(M+H)^+$; calcd for $C_{16}H_{19}ClN_3O_3^+$: 336.11].

7

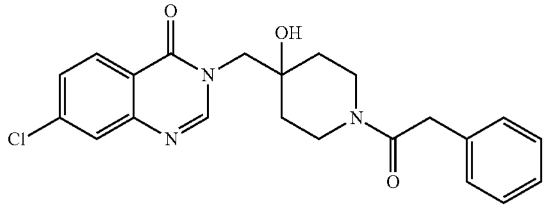

(7-Chloro-3-((4-hydroxy-1-(2-phenylacetyl)piperidin-4-yl)methyl)quinazolin-4(3H)-one: white solid, commercial compound)$^1$H NMR (500 MHz, DMSO) δ 8.27 (s, 1H), 8.15 (d, J=8.6 Hz, 1H), 7.75 (d, J=2.0 Hz, 1H), 7.57 (dd, J=8.6, 2.1 Hz, 1H), 7.30-7.24 (m, 2H), 7.24-7.15 (m, 3H), 4.07-4.03 (m, 1H), 3.97 (dd, J=38.6, 13.8 Hz, 2H), 3.74-3.64 (m, 3H), 3.29-3.20 (m, 1H), 3.03-2.92 (m, 1H), 1.51-1.27 (m, 4H). $^{13}C$ NMR (126 MHz, DMSO) δ 168.31, 159.88, 150.12, 148.71, 138.66, 135.76, 128.57, 128.19, 127.99, 126.93, 126.00, 125.95, 120.07, 68.97, 53.45, 41.15, 39.35, 36.86, 34.61, 33.99. LCMS (ESI) m/z 412.29 $[(M+H)^+$; calcd for $C_{22}H_{23}ClN_3O_3^+$: 412.14].

8

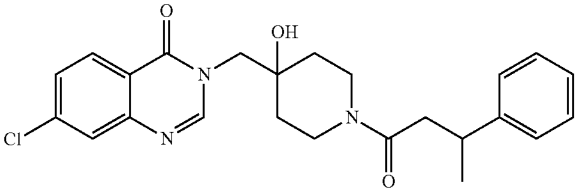

(7-Chloro-3-((4-hydroxy-1-(3-phenylbutanoyl)piperidin-4-yl)methyl)quinazolin-4(3H)-one: white solid, commercial compound)$^1$H NMR (500 MHz, DMSO) δ 8.29 (s, 1H), 8.18 (d, J=8.5 Hz, 1H), 7.71 (d, J=2.0 Hz, 1H), 7.56 (dd, J=8.6, 2.1 Hz, 1H), 7.30-7.22 (m, 4H), 7.18-7.13 (m, 1H), 4.12-3.55 (m, 4H), 3.41-2.85 (m, 3H), 2.62 (dd, J=14.9, 6.6 Hz, 1H), 2.54 (dd, J=14.9, 7.6 Hz, 1H), 1.40 (t, J=15.9 Hz, 4H), 1.25 (d, J=7.0 Hz, 3H). $^{13}C$ NMR (126 MHz, DMSO) δ 168.89, 159.94, 159.88, 150.11, 148.74, 146.42, 146.30, 138.68, 128.20, 127.97, 127.94, 126.94, 126.66, 126.63, 125.98, 125.72, 125.67, 120.10, 69.04, 68.99, 53.57, 40.82, 40.71, 39.99, 36.67, 35.99, 35.77, 34.78, 34.64, 34.09, 33.95, 21.81, 21.61. LCMS (ESI) m/z 440.39 $[(M+H)^+$; calcd for $C_{24}H_{27}ClN_3O_3^+$: 440.17].

9

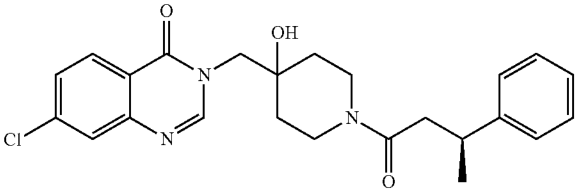

((S)-7-Chloro-3-((4-hydroxy-1-(3-phenylbutanoyl)piperidin-4-yl)methyl)quinazolin-4(3H)-one: white solid, 57% yield)$^1$H NMR (500 MHz, DMSO) δ 8.27 (d, J=12.8 Hz, 1H), 8.16 (d, J=8.6 Hz, 1H), 7.75 (d, J=1.6 Hz, 1H), 7.58 (dd, J=8.6, 2.0 Hz, 1H), 7.26 (dd, J=13.7, 6.6 Hz, 4H), 7.21-7.09 (m, 1H), 4.93 (d, J=5.8 Hz, 1H), 3.99 (dd, J=43.9, 13.7 Hz, 2H), 3.91 (s, 1H), 3.65 (t, J=12.2 Hz, 1H), 3.28-3.09 (m, 2H), 2.85 (d, J=13.2 Hz, 1H), 2.68-2.55 (m, 2H), 1.60-1.25 (m, 3H), 1.20 (dd, J=6.9, 1.5 Hz, 3H). $^{13}C$ NMR (126 MHz, DMSO) δ 168.89, 159.94, 159.88, 150.11, 148.74, 146.42, 146.30, 138.68, 128.20, 127.97, 127.94, 126.94, 126.66, 126.63, 125.98, 125.72, 125.67, 120.10, 69.04, 68.99, 53.57, 40.82, 40.71, 39.99, 36.67, 35.99, 35.77, 34.78, 34.64, 34.09, 33.95, 21.81, 21.61. LCMS (ESI) m/z 440.29 [(M+H)$^+$; calcd for $C_{24}H_{27}ClN_3O_3^+$: 440.17].

10

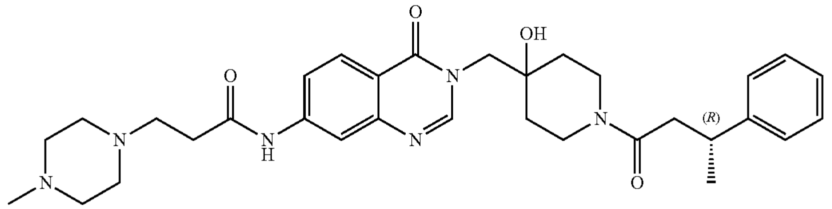

((R)—N-(3-((4-Hydroxy-1-(3-phenylbutanoyl)piperidin-4-yl)methyl)-4-oxo-3,4-dihydroquinazolin-7-yl)-3-(4-methylpiperazin-1-yl)propanamide: off-white solid, 75% yield) $^1H$ NMR (500 MHz, DMSO) δ 10.57 (s, 1H), 8.20 (d, J=13.1 Hz, 1H), 8.07 (d, J=8.7 Hz, 1H), 8.02 (d, J=1.6 Hz, 1H), 7.64 (d, J=8.7 Hz, 1H), 7.25 (dd, J=12.4, 6.2 Hz, 4H), 7.13 (dd, J=18.7, 10.4 Hz, 1H), 4.96 (d, J=5.8 Hz, 1H), 4.02 (d, J=13.6 Hz, 1H), 3.90 (q, J=14.0 Hz, 2H), 3.63 (dd, J=29.0, 16.2 Hz, 1H), 3.27-3.12 (m, 2H), 2.86 (dd, J=17.7, 14.8 Hz, 1H), 2.69-2.61 (m, 2H), 2.61-2.52 (m, 3H), 2.48-2.22 (m, 8H), 2.16 (s, 3H), 1.58-1.26 (m, 4H), 1.20 (d, J=6.4 Hz, 3H). $^{13}C$ NMR (126 MHz, DMSO) δ 170.76, 168.83, 159.92, 159.87, 149.10, 148.73, 146.41, 146.28, 144.06, 127.93, 127.90, 126.97, 126.62, 126.60, 125.69, 125.63, 118.04, 116.26, 114.45, 69.03, 68.98, 54.37, 53.22, 51.96, 45.30, 40.81, 40.71, 39.97, 36.67, 35.95, 35.74, 34.77, 34.64, 34.09, 34.01, 33.95, 21.79, 21.61. LCMS (ESI) m/z 575.32 [(M+H)$^+$; calcd for $C_{32}H_{43}N_6O_4^+$: 575.33].

11

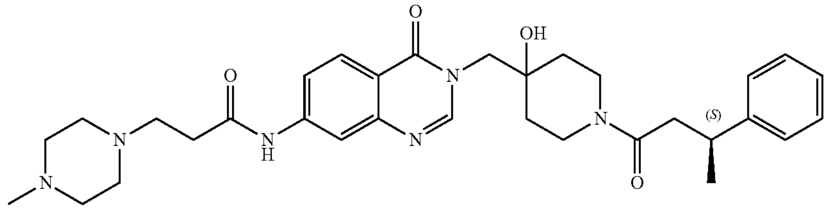

((S)—N-(3-((4-Hydroxy-1-(3-phenylbutanoyl)piperidin-4-yl)methyl)-4-oxo-3,4-dihydroquinazolin-7-yl)-3-(4-methylpiperazin-1-yl)propanamide: off-white solid, 26% yield) $^1H$ NMR (500 MHz, DMSO) δ 10.52 (s, 1H), 8.19 (d, J=13.1 Hz, 1H), 8.08 (d, J=8.7 Hz, 1H), 8.02 (d, J=2.0 Hz, 1H), 7.62 (dd, J=8.8, 1.4 Hz, 1H), 7.25 (dd, J=12.6, 6.3 Hz, 4H), 7.19-7.08 (m, 1H), 4.93 (s, 1H), 4.08-3.97 (m, 1H), 3.90 (q, J=14.0 Hz, 2H), 3.64 (t, J=12.9 Hz, 1H), 3.30-3.09 (m, 2H), 2.95-2.81 (m, 1H), 2.69-2.60 (m, 2H), 2.61-2.52 (m, 3H), 2.47-2.25 (m, 8H), 2.15 (s, 3H), 1.58-1.26 (m, 4H), 1.24-1.14 (m, 3H). $^{13}C$ NMR (126 MHz, DMSO) δ 170.76, 168.82, 159.88, 149.11, 148.74, 146.41, 146.29, 144.04, 127.94, 127.91, 127.00, 126.63, 125.69, 125.64, 118.04, 116.28, 114.46, 68.99, 54.43, 53.24, 52.02, 45.38, 40.82, 40.71, 39.96, 36.68, 35.96, 35.75, 34.77, 34.64, 34.03, 21.80, 21.61. LCMS (ESI) m/z 575.32 [(M+H)$^+$; calcd for $C_{32}H_{43}N_6O_4^+$: 575.33].

12

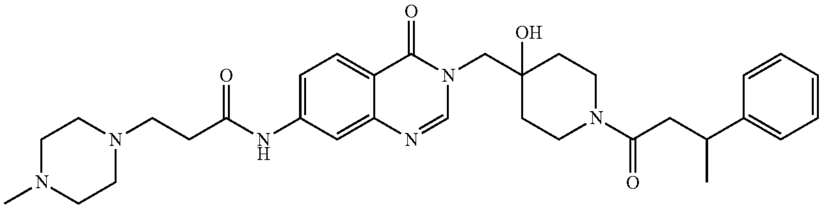

(N-(3-((4-Hydroxy-1-(3-phenylbutanoyl)piperidin-4-yl)methyl)-4-oxo-3,4-dihydroquinazolin-7-yl)-3-(4-methylpiperazin-1-yl)propenamide: white solid, 16% yield)$^1$H NMR (500 MHz, DMSO) δ 10.84 (s, 1H), 8.25 (d, J=13.2 Hz, 1H), 8.15-7.99 (m, 2H), 7.69 (d, J=8.7 Hz, 1H), 7.28-7.25 (m, 4H), 7.19-7.10 (m, 1H), 4.05-3.88 (m, 3H), 3.65 (t, J=12.8 Hz, 1H), 3.28-3.14 (m, 10H), 2.92-2.85 (m, 3H), 2.79 (s, 3H), 2.64-2.53 (m, 4H), 1.53-1.28 (m, 4H), 1.20 (d, J=6.0, 3H). $^{13}$C NMR (126 MHz, DMSO) δ 169.60, 160.66, 160.61, 158.82, 158.57, 149.95, 149.34, 147.15, 147.02, 144.63, 128.69, 128.66, 127.69, 127.38, 127.35, 126.44, 126.39, 118.90, 117.14, 115.37, 69.76, 69.71, 53.94, 41.57, 41.46, 40.88, 40.70, 37.42, 36.71, 36.49, 35.50, 35.37, 34.81, 34.66, 22.53, 22.34. LCMS (ESI) m/z 575.32 [(M+H)$^+$; calcd for $C_{32}H_{43}N_6O_4^+$: 575.33].

13

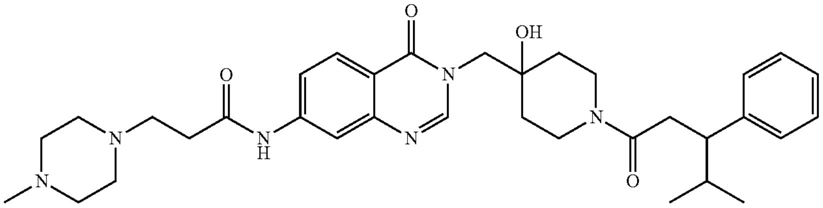

(N-(3-((4-Hydroxy-1-(4-methyl-3-phenylpentanoyl)piperidin-4-yl)methyl)-4-oxo-3,4-dihydroquinazolin-7-yl)-3-(4-methylpiperazin-1-yl)propenamide: off-white solid, 40% yield)$^1$H NMR (500 MHz, DMSO) δ 10.65 (s, 1H), 8.21 (d, J=16.9 Hz, 1H), 8.11 (dd, J=8.7, 1.9 Hz, 1H), 8.05 (s, 1H), 7.65 (d, J=8.7 Hz, 1H), 7.23 (td, J=7.6, 2.9 Hz, 2H), 7.15 (t, J=6.5 Hz, 2H), 7.13-7.06 (m, 1H), 4.04-3.93 (m, 2H), 3.85 (s, 1H), 3.75-3.61 (m, 1H), 3.58-2.98 (m, 10H), 2.91-2.55 (m, 10H), 1.88-1.80 (m, 1H), 1.53-1.25 (m, 3H), 1.12-1.06 (m, 1H), 0.89 (t, J=7.2 Hz, 3H), 0.70-0.61 (m, 3H). $^{13}$C NMR (126 MHz, DMSO) δ 169.94, 169.86, 160.61, 160.53, 149.95, 149.29, 144.51, 144.09, 144.03, 128.82, 128.79, 128.24, 128.16, 127.81, 126.31, 118.89, 117.21, 115.33, 69.76, 69.66, 54.04, 50.83, 49.24, 49.08, 48.75, 42.48, 41.51, 37.43, 37.33, 36.01, 35.94, 35.55, 35.31, 34.72, 34.65, 32.83, 32.63, 32.39, 21.24, 21.19, 20.76, 20.56. LCMS (ESI) m/z 603.43 [(M+H)$^+$; calcd for $C_{34}H_{47}N_6O_4^+$: 603.37].

14

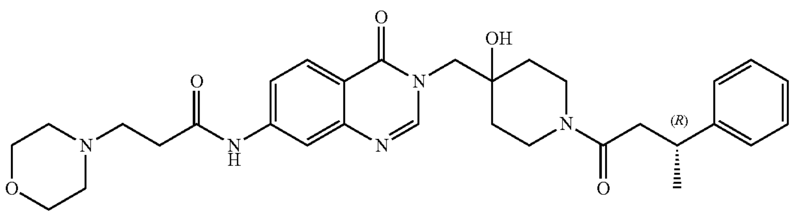

((R)—N-(3-((4-hydroxy-1-(3-phenylbutanoyl)piperidin-4-yl)methyl)-4-oxo-3,4-dihydroquinazolin-7-yl)-3-morpholinopropanamide: off-white solid, 65% yield)$^1$H NMR (500 MHz, DMSO) δ 10.52 (s, 1H), 8.20 (d, J=13.3 Hz, 1H), 8.07 (d, J=8.7 Hz, 1H), 8.04 (d, J=1.8 Hz, 1H), 4.96 (d, J=6.4 Hz, 1H), 4.02 (d, J=13.7 Hz, 1H), 3.90 (q, J=14.0 Hz, 2H), 3.73-3.60 (m, 1H), 3.59-3.55 (m, 4H), 3.18 (ddd, J=21.0, 18.3, 9.2 Hz, 2H), 2.93-2.80 (m, 1H), 2.65 (t, J=6.9 Hz, 2H), 2.61-2.54 (m, 3H), 2.41 (m, 4H), 1.40 (dddd, J=41.2, 26.0, 16.8, 9.5 Hz, 4H), 1.19 (dd, J=6.9, 1.7 Hz, 3H). $^{13}$C NMR (126 MHz, DMSO) δ 170.62, 168.81, 160.00, 149.15, 148.76, 146.44, 146.31, 144.09, 118.13, 116.29, 114.51, 69.06, 65.93, 53.73, 52.79, 40.85, 40.75, 39.98, 36.71, 36.00, 35.78, 34.79, 34.66, 34.11, 33.98, 33.81, 21.83, 21.64. LCMS (ESI) m/z 562.32 [(M+H)$^+$; calcd for $C_{31}H_{40}N_5O_5^+$: 562.30].

15

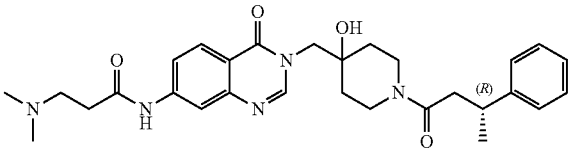

((R)-3-(Dimethylamino)-N-(3-((4-hydroxy-1-(3-phenylbutanoyl)piperidin-4-yl)methyl)-4-oxo-3,4-dihydroquinazolin-7-yl)propanamide: off-white solid, 36% yield)$^1$H NMR (500 MHz, DMSO) δ 10.47 (s, 1H), 8.18 (dd, J=13.0, 7.3 Hz, 1H), 8.06 (d, J=8.7 Hz, 1H), 8.02 (d, J=2.0 Hz, 1H), 7.63-7.59 (m, 1H), 7.24 (dd, J=12.6, 6.3 Hz, 4H), 7.17-7.09 (m, 1H), 4.92 (s, 1H), 4.07-3.95 (m, 1H), 3.89 (q, J=14.0 Hz, 2H), 3.63 (t, J=13.0 Hz, 1H), 3.18 (ddd, J=20.8, 18.0, 9.1 Hz, 2H), 2.86 (ddd, J=13.8, 10.5, 5.5 Hz, 1H), 2.60-2.54 (m, 3H), 2.54-2.47 (m, 2H), 2.17 (s, 6H), 1.56-1.23 (m, 4H), 1.24-1.15 (m, 3H). $^{13}$C NMR (126 MHz, DMSO) δ 170.76, 168.83, 159.89, 149.09, 148.74, 146.42, 146.29, 144.07, 127.94, 127.92, 126.97, 126.61, 125.70, 125.64, 118.06, 116.26, 114.46, 68.99, 54.59, 53.29, 44.63, 40.82, 40.72, 39.98, 39.96, 36.68, 35.97, 35.75, 34.78, 34.65, 34.61, 34.11, 33.96, 21.80, 21.61. LCMS (ESI) m/z 520.31 [(M+H)$^+$; calcd for $C_{29}H_{38}N_5O_4^+$: 520.29].

16

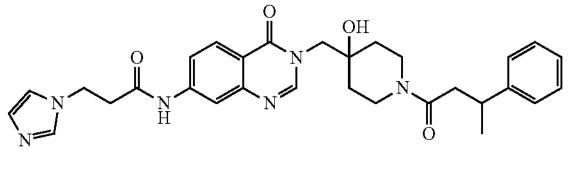

(N-(3-((4-hydroxy-1-(3-phenylbutanoyl)piperidin-4-yl)methyl)-4-oxo-3,4-dihydroquinazolin-7-yl)-3-(1H-imidazol-1-yl)propenamide: white solid, 19% yield)$^1$H NMR (500 MHz, DMSO) δ 10.62 (s, 1H), 9.16 (s, 1H), 8.22 (d, J=12.9 Hz, 1H), 8.09 (d, J=8.7 Hz, 1H), 8.00 (s, 1H), 7.80 (s, 1H), 7.67 (s, 1H), 7.62 (d, J=8.8 Hz, 1H), 7.28-7.25 (m, 4H), 7.15 (d, J=3.6 Hz, 1H), 4.03-3.87 (m, 3H), 3.65 (t, J=12.4 Hz, 1H), 3.26-3.14 (m, 2H), 3.08 (t, J=6.3 Hz, 2H), 2.90-2.85 (m, 1H), 2.64-2.49 (m, 4H), 1.54-1.25 (m, 4H), 1.20 (d, J=5.4 Hz, 3H). $^{13}$C NMR (126 MHz, DMSO) δ 169.60, 169.43, 160.60, 160.55, 158.88, 158.60, 149.99, 149.25, 147.15, 147.03, 144.33, 136.33, 128.68, 128.66, 127.85, 127.37, 127.35, 126.44, 126.39, 122.58, 120.32, 118.86, 117.25, 115.33, 69.77, 69.71, 54.04, 44.94, 41.55, 41.44, 40.71, 37.41, 36.70, 36.57, 36.49, 35.52, 35.39, 34.80, 34.66, 22.53, 22.35. LCMS (ESI) m/z 543.22 [(M+H)$^+$; calcd for $C_{30}H_{35}N_6O_4^+$: 543.27].

17

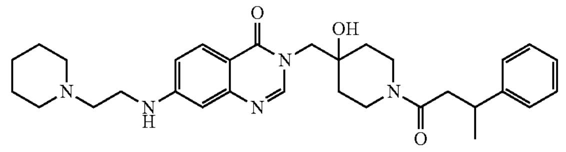

((N-(3-((4-hydroxy-1-(3-phenylbutanoyl)piperidin-4-yl)methyl)-4-oxo-3,4-dihydroquinazolin-7-yl)-3-(piperidin-1-yl)propenamide: white solid, 18% yield)$^1$H NMR (500 MHz, DMSO) δ 10.69 (s, 1H), 9.32 (s, 1H), 8.23 (d, J=12.8 Hz, 1H), 8.11 (dd, J=8.7, 1.9 Hz, 1H), 8.05 (s, 1H), 7.65 (d, J=8.7 Hz, 1H), 7.19-7.31 (m, 4H), 7.15 (s, 1H), 4.03-3.89 (m, 3H), 3.65 (t, J=12.4 Hz, 1H), 3.48-3.40 (m, 4H), 3.26-3.15 (m, 2H), 2.98-2.89 (m, 5H), 2.64-2.51 (m, 2H), 1.84 (d, J=13.3 Hz, 2H), 1.68-1.62 (m, 3H), 1.55-1.31 (m, 5H), 1.21 (d, J=6.6 Hz, 3H). $^{13}$C NMR (126 MHz, DMSO) δ 169.60, 169.22, 160.61, 160.56, 158.87, 158.59, 150.01, 149.29, 147.15, 147.03, 144.41, 128.68, 128.66, 127.87, 127.37, 127.35, 126.44, 126.39, 118.89, 117.27, 115.38, 69.77, 69.72, 54.05, 52.89, 52.05, 41.55, 41.45, 40.69, 37.41, 36.71, 36.49, 35.53, 35.40, 34.81, 34.67, 31.22, 23.00, 22.53, 22.35, 21.65. LCMS (ESI) m/z 560.22 [(M+H)$^+$; calcd for $C_{32}H_{42}N_5O_4^+$: 560.32].

Example 3: Biological Assays

USP7 enzyme expression and purification A construct of human USP7 covering residues 208-560 in the pET28aLIC vector was overexpressed in *E. coli* BL21 (DE3) in terrific broth (TB) medium in the presence of 50 μg/ml of kanamycin. Cells were grown at 37° C. to an OD of 0.8, cooled to 17° C., induced with 500 μM isopropyl-1-thio-D-galactopyranoside (IPTG), incubated overnight at 17° C., collected by centrifugation, and stored at −80° C. Cell pellets were sonicated in buffer A (50 mM HEPES pH 7.5, 300 mM NaCl, 10% glycerol, 10 mM Imidazole, and 3 mM BME) and the resulting lysate was centrifuged at 30,000×g for 40 min. Ni-NTA beads (Qiagen) were mixed with lysate supernatant for 30 min and washed with buffer A. Beads were transferred to an FPLC-compatible column and the bound protein was washed with 15% buffer B (50 mM HEPES pH 7.5, 300 mM NaCl, 10% glycerol, 300 mM Imidazole, and 3 mM BME) and eluted with 100% buffer B. Thrombin was added to the eluted protein and incubated at 4° C. overnight. The sample was then concentrated and passed through a Superdex 200 16/60 column (GE Healthcare) in a buffer containing 20 mM HEPES pH 7.5, 200 mM NaCl, 5% glycerol, and 1 mM TCEP. Fractions were pooled, concentrated and frozen at −80° C.

USP7 full length (aa 0001.1102) in pET28aLIC was transformed in BL21(DE3) cells. An overnight culture was used to inoculate one liter of TB supplemented with 50 μg/ml kanamycin. Cells were grown at 37° C. till they reached optical density (OD) ~0.6 at 600 nm. Protein expression was initiated by the addition of 0.4 mM IPTG. Cells were then grown for 16-20 hours at 17° C. prior collection by centrifugation. Cell pellets were washed in PBS and resuspended in 25 mM HEPES pH 7.5, 500 mM NaCl, 10% glycerol and 1 mM TCEP, 10 mM Imidazole, 0.1% IGEPAL sonicated and incubated with Ni-Nta beads (Quiagen) for 30 min at 4° C. Beads were washed with 10% buffer B (25 mM HEPES pH 7.5, 500 mM NaCl, 10% glycerol and 1 mM TCEP, 250 mM Imidazole) and eluted with 100% buffer B. Protein containing fractions were concentrated and loaded on Superdex 200 10/300 GL column in a buffer containing 20 mM HEPES pH 7.5, 200 mM NaCl, 5% glycerol, and 1 mM TCEP. Fractions were pooled, concentrated and frozen at −80° C.

Site Directed Mutagenesis

Figure 2A:
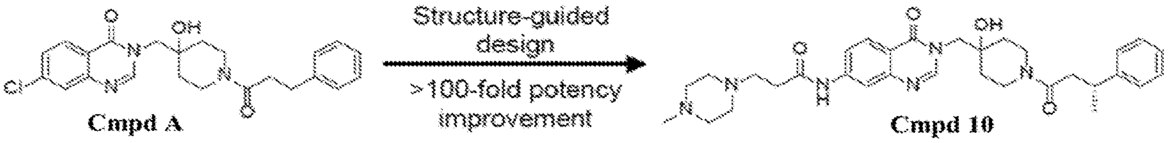
FIG. 2A: Structure-guided optimization of compound A led to compounds 10 and 11. The enantiomer of compound 10, compound 11, is 80-fold less active.
Figure 2A:
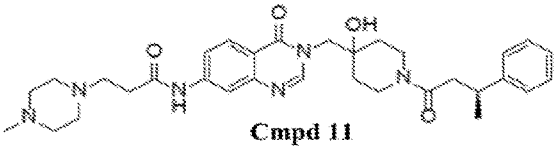
Figure 2B:
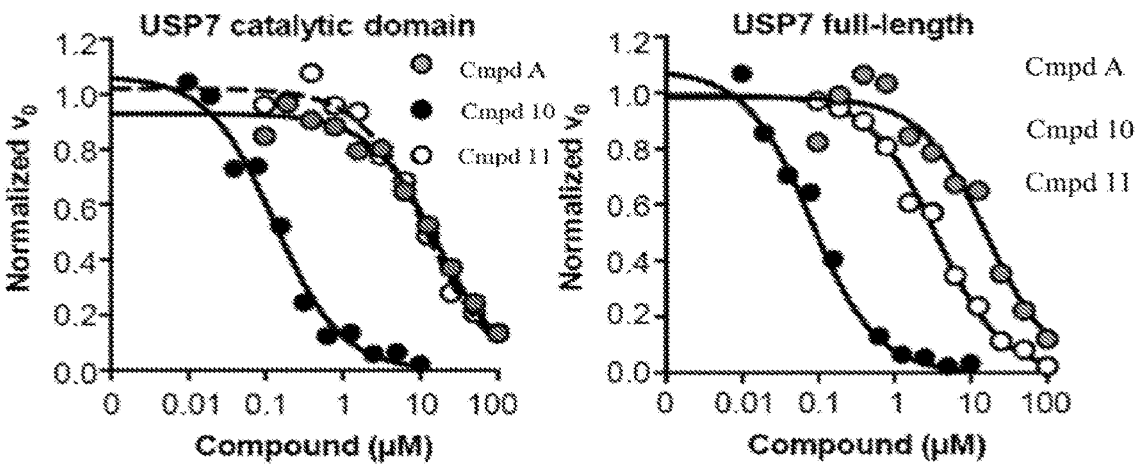
FIG. 2B: Dose-dependent inhibition of the USP7 catalytic domain (amino acids 208-560) and full-length USP7 (amino acids 1-1102) by compound 10 and compound 11 using Ub-AMC as substrate.
Figure 2C:
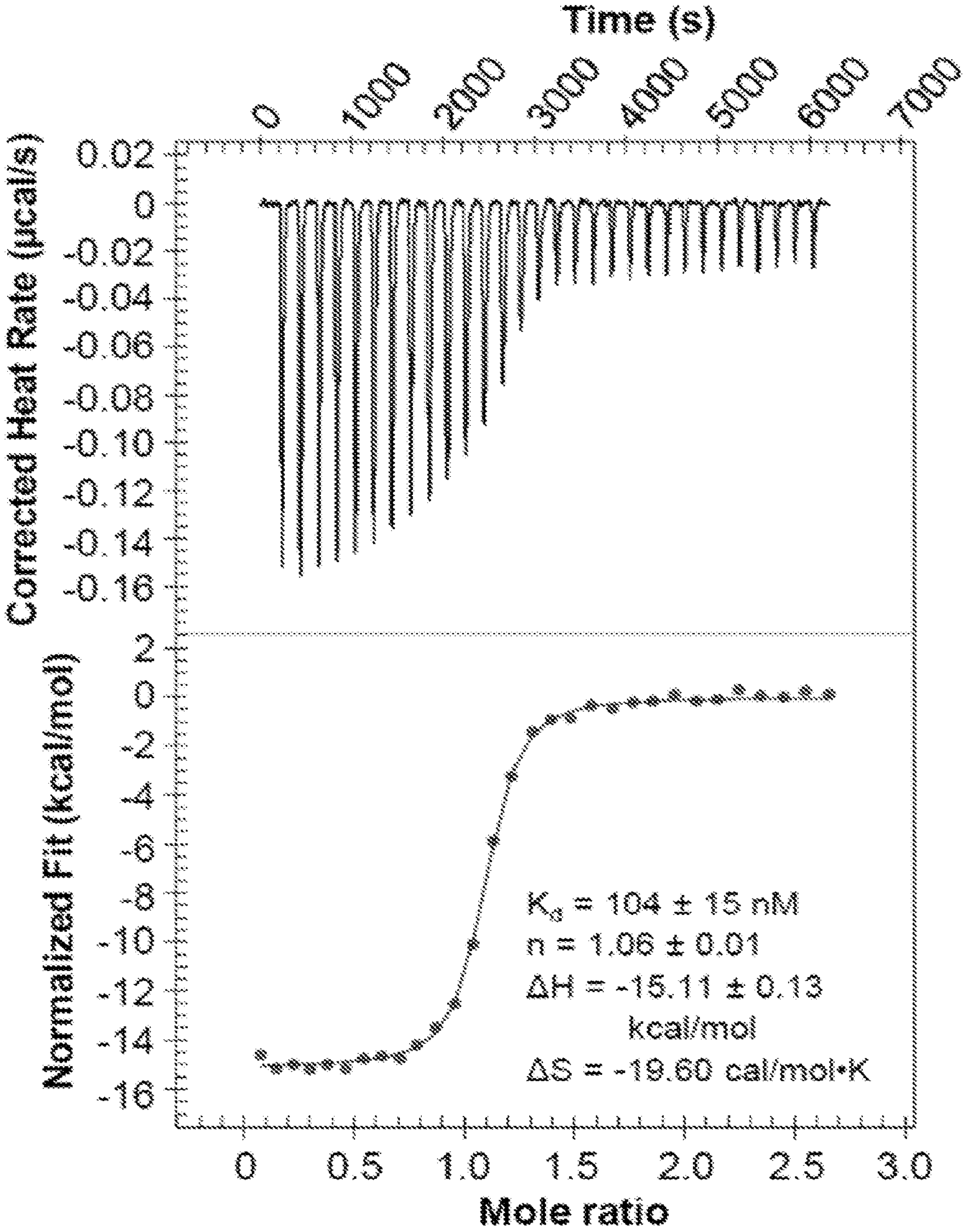
FIG. 2C: Assessment of compound 10 binding to USP7 using isothermal calorimetry.
Figure 2D:
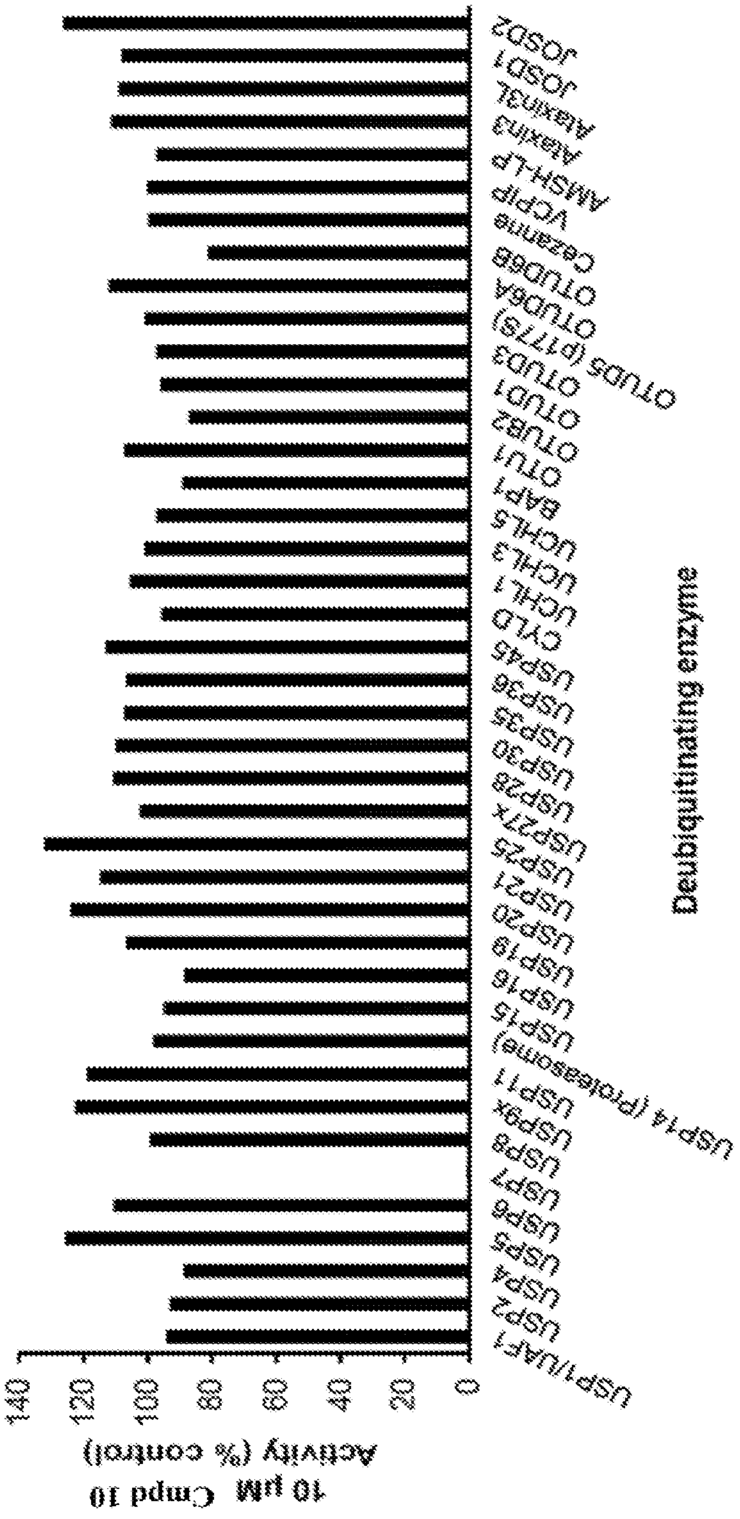
FIG. 2D: Inhibitory activity of compound 10 across a panel of 41 purified DUBs using ubiquitin-rhodamine (Ub-Rho) as substrate.

Amino acid mutations of catalytic domain and full length USP7 were introduced by PCR using QuikChange site-directed mutagenesis kit (Stratagene, La Jolla, CA) following manufacturer's protocol. Table 1 reports primer used for each mutation created.

lytic domain by compounds A, 10 and 11. FIG. 2D illustrates inhibitory activity of compound 10 across a panel of 41 purified DUBs using ubiquitin-rhodamine (Ub-Rho) as substrate.

Competitive Activity Based Protein Profiling

Figure 5A:
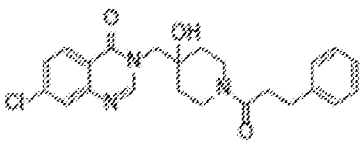
FIG. 5A: USP7 inhibitory activity and mouse liver microsome (MLM) stability of disclosed compounds.
Figure 5A:
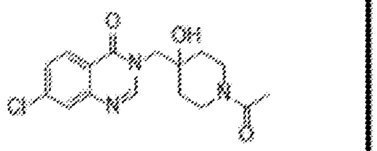
Figure 5A:
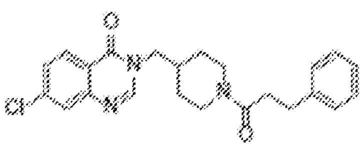
Figure 5A:
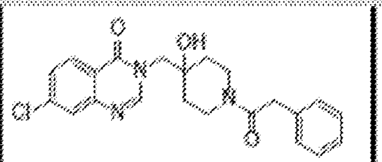
Figure 5A:
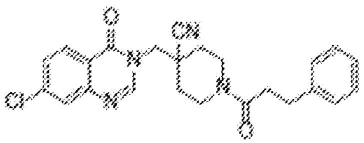
Figure 5A:
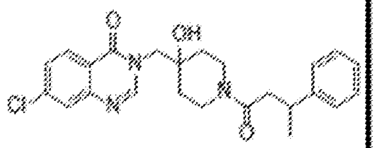
Figure 5A:
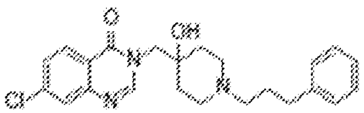
Figure 5A:
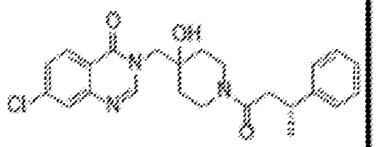
Figure 5A:
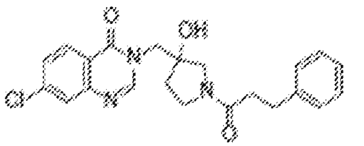
Figure 5A:
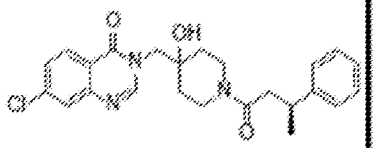
Figure 5B:
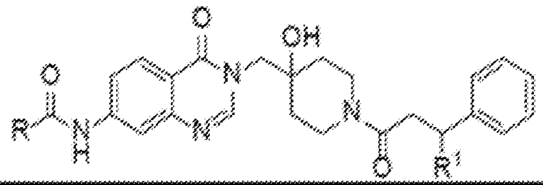
FIG. 5B: Structures, USP7 inhibitory activity and mouse liver microsome (MLM) stability of disclosed compounds.
Figure 5B:
Figure 5B:
Figure 5B:
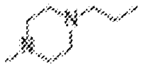
Figure 5B:
Figure 5B:
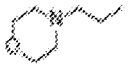
Figure 5B:
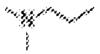
Figure 5B:
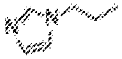
Figure 5B:
Figure 5C:
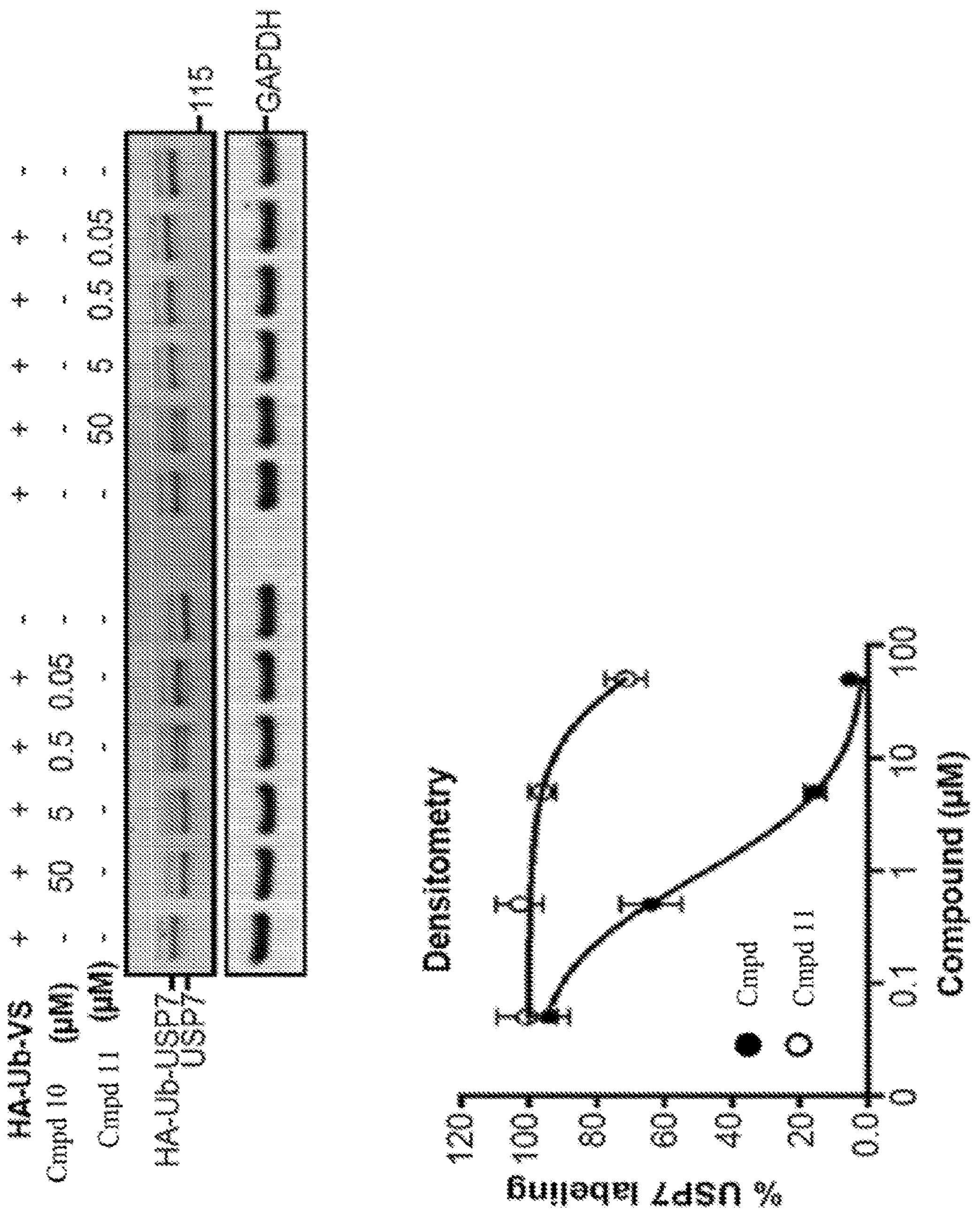
FIG. 5C: Analysis of the ability of compounds 10 and 11 to bind native USP7 across multiple doses in HEK293T lysates using competitive activity based protein profiling.
Figure 6A:
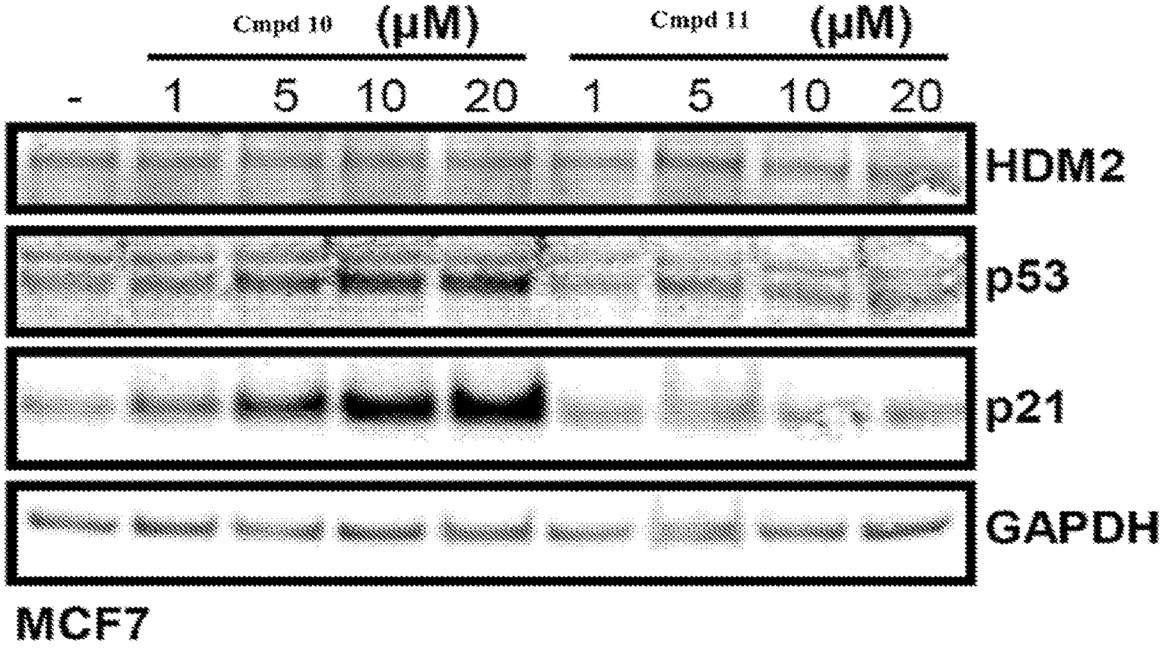
FIG. 6A: Compound 10 promotes loss HDM2 and accumulation of p53 and p21. Analysis of HDM2, p53 and p21 protein levels in MCF7 cells treated with compounds 10 or 11 at the indicated concentration for 16 hours.
Figure 6B:
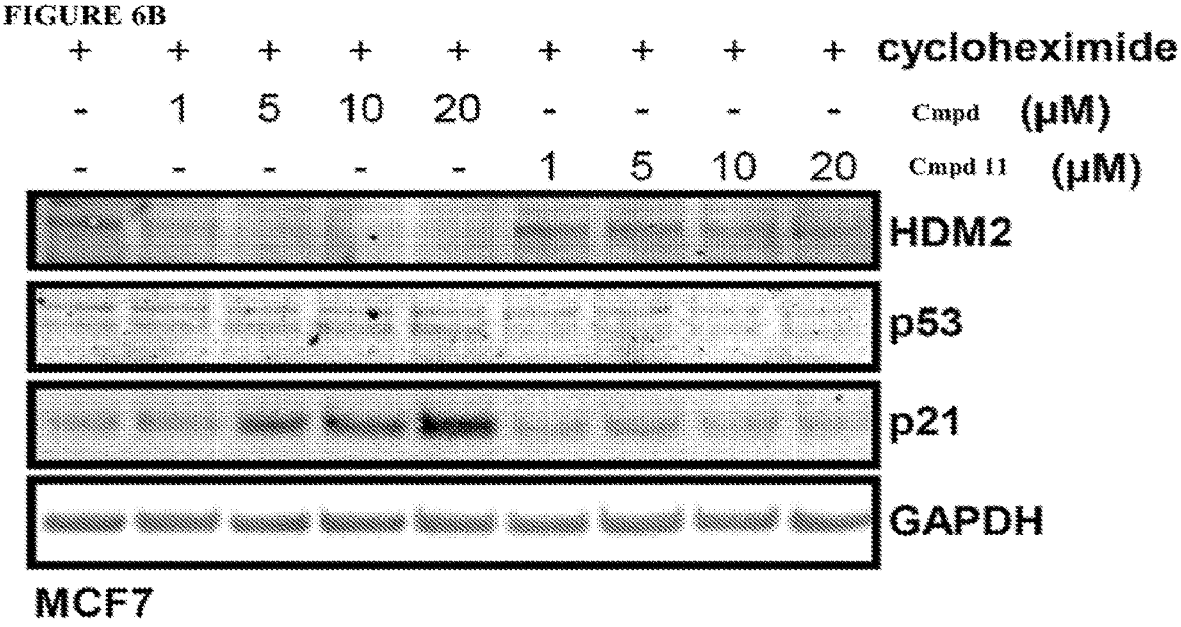
FIG. 6B: Analysis of HDM2, p53 and p21 protein levels in MCF7 cells following 16 hours of treatment with compounds 10 or 11 at the indicated concentration with addition of cycloheximide for the last 2 hours.
Figure 6C:
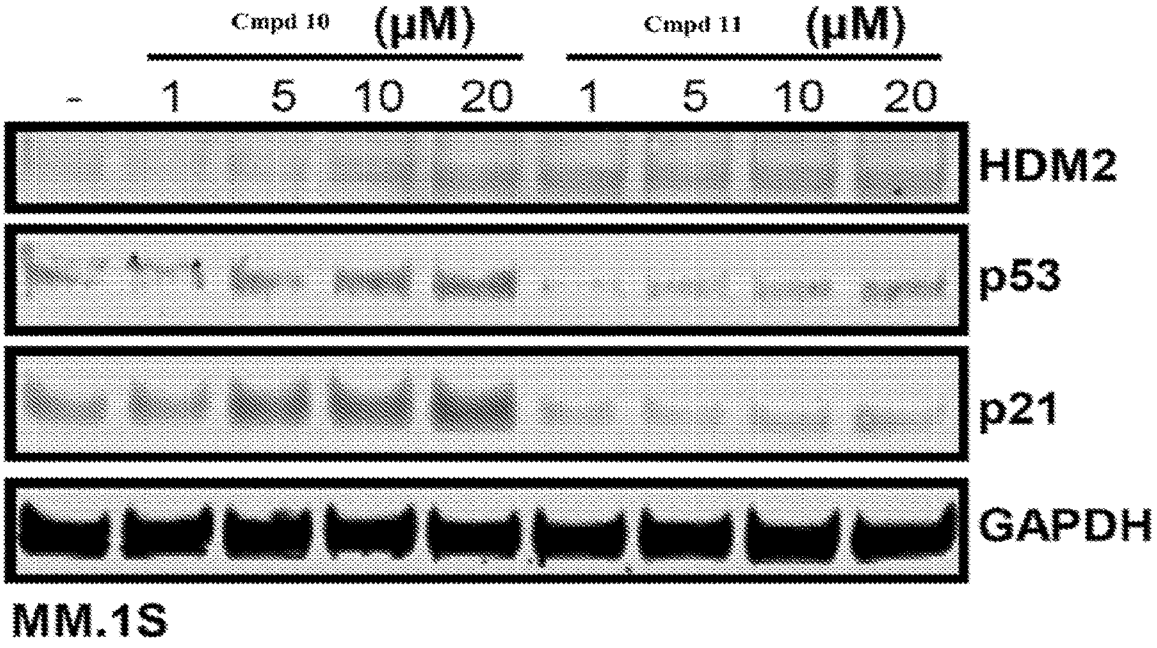
FIG. 6C: Analysis of HDM2, p53 and p21 protein levels in MM.1S cells treated with compounds 10 or 11 at the indicated concentration for 6 hours.
Figure 6D:
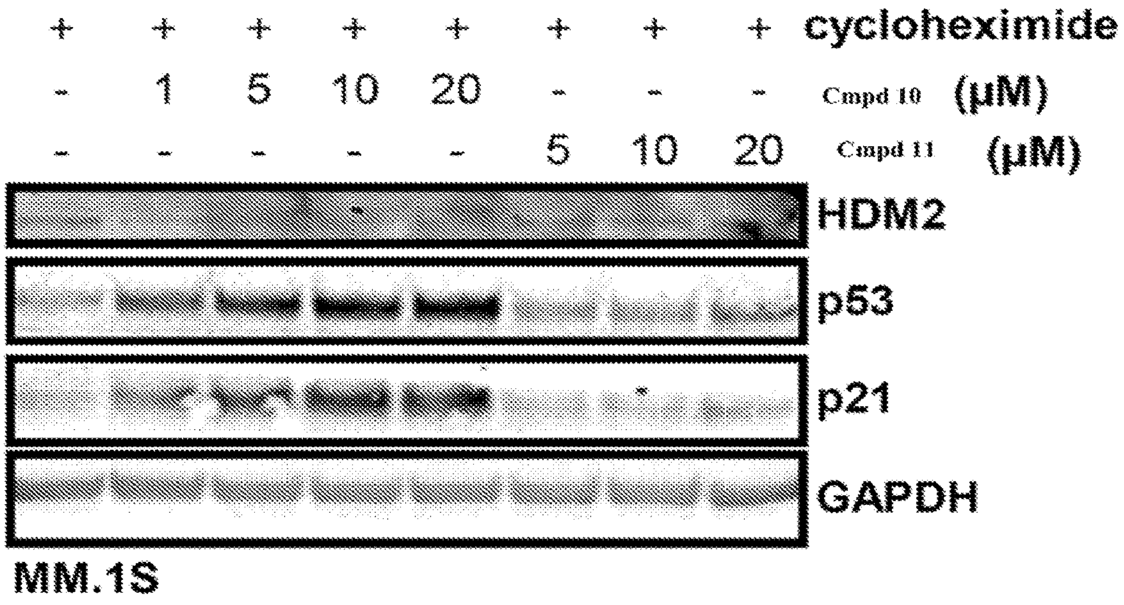
FIG. 6D: Analysis of HDM2, p53 and p21 protein levels in MM.1S cells following 6 hours of treatment with compounds 10 or 11 at the indicated concentration with addition of cycloheximide for the last 2 hours.

HEK 293T cells were pelleted, washed with PBS, lysed on ice (50 mM Tris pH 7.6, 150 mM NaCl, 5 mM $MgCl_2$, 0.5 mM EDTA, 0.5% NP-40, 10% glycerol, 1 mM TCEP, phosphatase inhibitor cocktails (Sigma P5726 and Calbiochem 524624), and protease inhibitors (pepstatin, leupeptin, PMSF, and aprotinin), and clarified by centrifugation. Protein content was quantified by BCA, and 50 µg of lysate was diluted into 30 uL labeling buffer (50 mM Tris pH 7.6, 5 mM $MgCl_2$, 0.5 mM EDTA, 250 mM sucrose, 1 mM TCEP) and incubated at room temperature with shaking with the indicated inhibitors for 30 minutes. Samples were then supplemented with 1 uM HA-Ub-VS and incubated at room temperature with shaking for 15 minutes. Reactions were quenched with 4×LDS sample buffer (Thermo Fisher B0007) supplemented with 10% BME, vortexed vigorously, and heated to 95° C. for 5 minutes. Samples were resolved by SDS-PAGE and analyzed by Western blot with the indicated antibodies (FIG. 5C).

TABLE 1

| Mutation | Primer | Orientation of Primers |
|---|---|---|
| Q351S | GAAGATTATTATGATATCTCGCTAAGTATCAAAGG | forward |
| | CCTTTGATACTTAGCGAGATATCATAATAATCTTC | reverse |
| M407K | CCAGTGTTACATCTACAACTGAAGAGATTTATGTATGACCC | forward |
| | GGGTCATACATAAATCTCTTCAGTTGTAGATGTAACACTGG | reverse |
| M410S | CTACAACTGATGAGATTTAGTTATGACCCTCAGACGGACC | forward |
| | GGTCCGTCTGAGGGTCATAACTAAATCTCATCAGTTGTAG | reverse |
| M407K/ | CCAGTGTTACATCTACAACTGAAGAGATTTAGTTATGACCCTCAGACGGACC | forward |
| M410S | GGTCCGTCTGAGGGTCATAACTAAATCTCTTCAGTTGTAGATGTAACACTGG | reverse |
| K420A | CCCTCAGACGGACCAAAATATCGCGATCAATGATAGGTTTGAATTCC | forward |
| | GGAATTCAAACCTATCATTGATCGCGATATTTTGGTCCGTCTGAGGG | reverse |
| H456A | CTTCATGCAGTCCTGGTTGCTAGTGGAGATAATCATGGTGG | forward |
| | CCACCATGATTATCTCCACTAGCAACCAGGACTGCATGAAG | reverse |
| H461A | CTGGTTCATAGTGGAGATAATGCTGGTGGACATTATGTGG | forward |
| | CCACATAATGTCCACCAGCATTATCTCCACTATGAACCAG | reverse |
| Y514A | CGACACTGCACTAATGCTGCCATGTTAGTCTACATCAGGG | forward |
| | CCCTGATGTAGACTAACATGGCAGCATTAGTGCAGTGTCG | reverse |

Isothermal Titration Calorimetry

The binding affinity of protein/ligand was measured by adding 0.02 mM protein in cell and titrating with 0.2 mM ligand in the syringe using an Auto-ITC200 microcalorimeter (Malvern) at 20° C. (FIG. 2C). Proteins and ligands were prepared within ITC buffer containing 20 mM HEPES pH 7.5, 150 mM NaCl, and 2% DMSO. The data were fit using Origin 7.0 software. ITC results are summarized in Table 2.

TABLE 2

| Ligand | Kd (µM) | | | DH (kcal/mol) | | | n (stoichiometry) | | | DS (cal/mol · K) |
|---|---|---|---|---|---|---|---|---|---|---|
| 10 | 0.104 | ± | 0.015 | −15.1 | ± | 0.1 | 1.06 | ± | 0.01 | 119.6 |
| A | 7.614 | ± | 3.216 | −5.4 | ± | 1.3 | 0.98 | ± | 0.15 | 5.3 |
| 7 | No binding detected | | | | | | | | | |
| 8 | 1.838 | ± | 0.895 | −3.9 | ± | 0.2 | 2.46 | ± | 0.09 | 13.1 |
| 9 | 0.797 | ± | −0.097 | −13.5 | ± | 0.3 | 0.96 | ± | 0.01 | −17.3 |

Cell Treatments

MCF7 and MM.1S were grown in RPMI supplemented with 10% Fetal Bovine serum (FBS) and antibiotics. Cells were treated with DMSO or different concentrations of compounds 10 and 11 for 6 (MM1S) or 16 (MCF7) hours in presence or absence of cycloheximide. For the experiments in which cycloheximide was used, cells were treated with Selectivity Profiling Selectivity profiling (DUBProfiler) was performed by Ubiquigent using the manufacturer's protocols. FIG. 2B illustrates the dose-dependent inhibition of the USP7 catacompounds for 4 (MM1S) or 14 (MCF7) hours prior to the addition of 50 μg/ml of cycloheximide. At 6 or 16 h time point cells were washed in PBS and lysed in modified RIPA buffer (1% Triton X-100, 1% sodium deoxycholate, 0.1% SDS, 20 mM Tris, 150 mM NaCl, 1 mM EDTA) containing phosphatase inhibitor cocktails 1 and 2 (Sigma), and protease inhibitors. Protein concentrations were quantified using the BCA protein assay kit (Pierce) and samples were probed by immunoblotting using mdm2 (santa cruz sc-965), p53 (cell signaling 9282), p21 (cell signaling 2947), GAPDH (cell signaling 2118), USP7 (cell signaling 4833) antibodies (FIGS. 6A-D).

Peripheral Blood Mononuclear Cell Testing

Peripheral blood mononuclear cells (PBMCs) were generously provided by Dr. Steven Treon and Dr. Guang Yang. PBMCs from normal individuals were isolated by density gradient centrifugation through Ficoll-Plaque Plus (Amersham Pharmacia Biotech AB, Uppsala, Sweden) at 400×g for 25 minutes, followed by two washes in PBS. Cells were then maintained in RPMI+10% FBS, supplemented with 10% FBS. Primary cells were obtained through written consent under approval of the Dana-Farber Cancer Institute Institutional Review Board. The trypan blue exclusion assay has been previously described (Weisberg et al., 2002) and was used for quantification of PBMCs prior to seeding for CellTiter-Glo Luminescent Cell Viability assays (Promega, Madison, WI). These assays were used for proliferation studies and carried out according to manufacturer instructions. Cell viability is reported as percentage of control (untreated) cells, and error bars represent the standard deviation for each data point.

Ub-AMC Assay

USP7 and mutants were tested for their activity in Ubiquitin-AMC assay in presence or absence of inhibitors. For this assay USP7 catalytic domain WT or mutant was used at the following concentrations: 250 nM USP7 WT, M407K, M407K/M410S or Q351S, 125 nM H461A, 600 nM Y514A and 10 nM M410S. For the same assay USP7 full length WT and Q351 mutant were used at 50 nM. USP7 variants were pre-incubated with different concentrations of inhibitors or DMSO as a control in 50 mM HEPES pH7.6, 0.5 mM EDTA, 11 uM ovalbumin, 5 mM DTT. The reaction was incubated 30 min at room temperature prior to the addition of 2 uM Ubiquitin-AMC (Boston Biochem) substrate. The initial rate of the reaction was measured by collecting fluorescence data at one minute interval over 30-minute period using a Clariostar fluorescence plate reader at excitation and emission wavelength of 345 and 445 nm respectively. The calculated initial rate values were plotted against inhibitor concentrations to determine $IC_{50}$s. All the experimental data were plotted using Prism GraphPad. FIG. 2A illustrates the structure guided optimization for the inhibition of USP7. Compound A (WO 2013/030218) shown below was optimized to arrive at compounds 10 and 11.

A

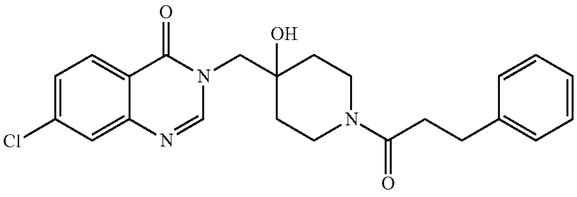

Figure 3A:
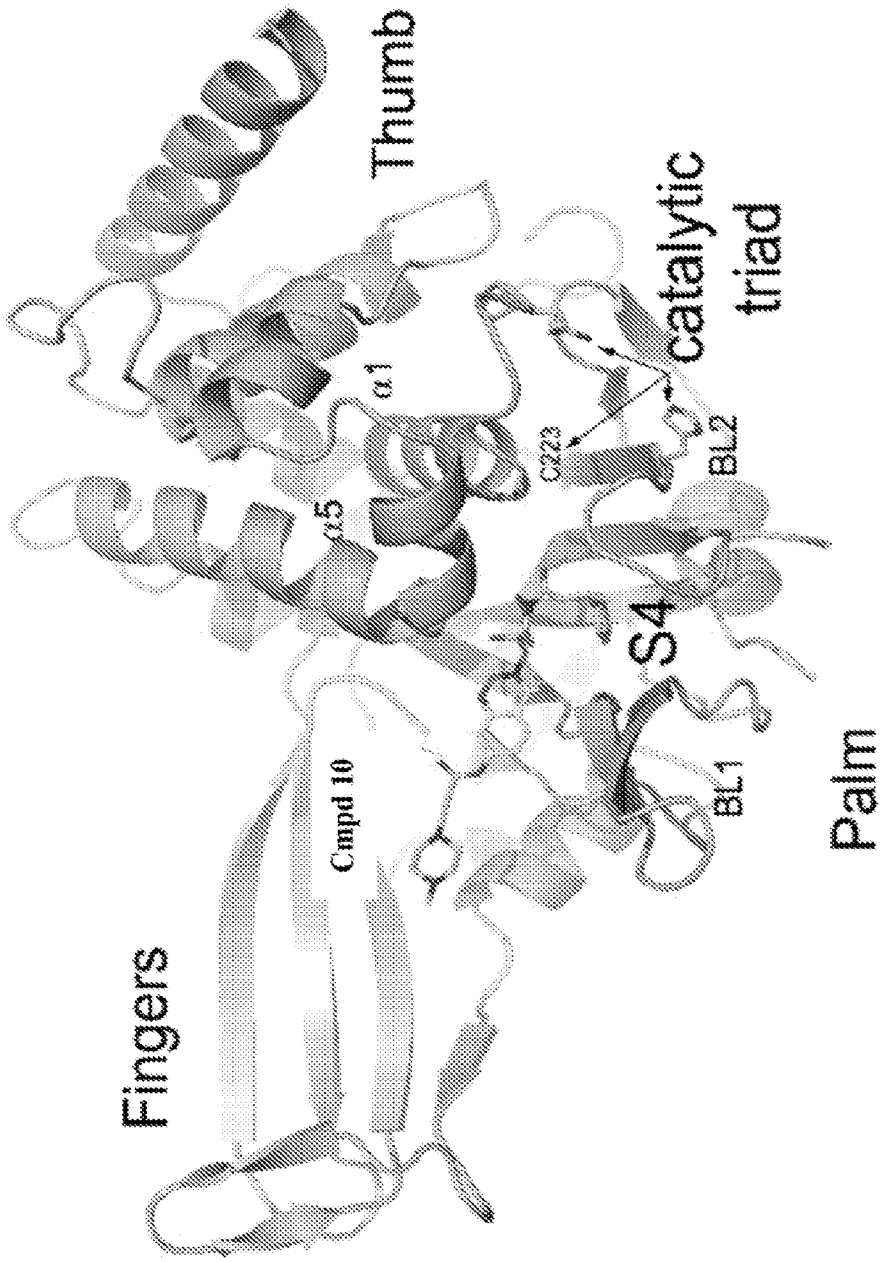
FIG. 3A: Characterization of compound 10 binding to USP7 using ribbon diagram of USP7 with compound 10.
Figure 3B:
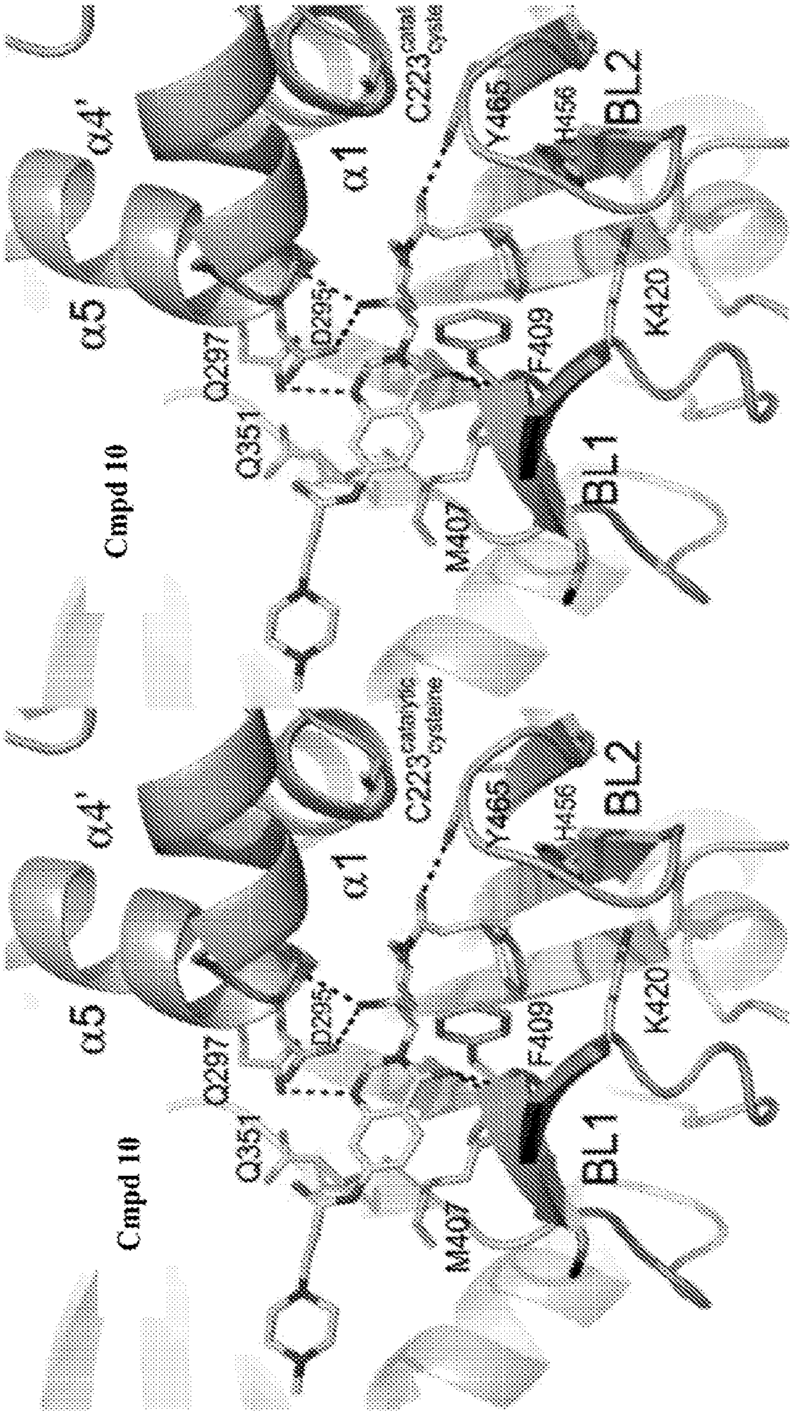
FIG. 3B: Stereoview of USP7 (light blue) bound to compound 10 (yellow). Hydrogen bonds are indicated by dashed lines.
Figure 3C:
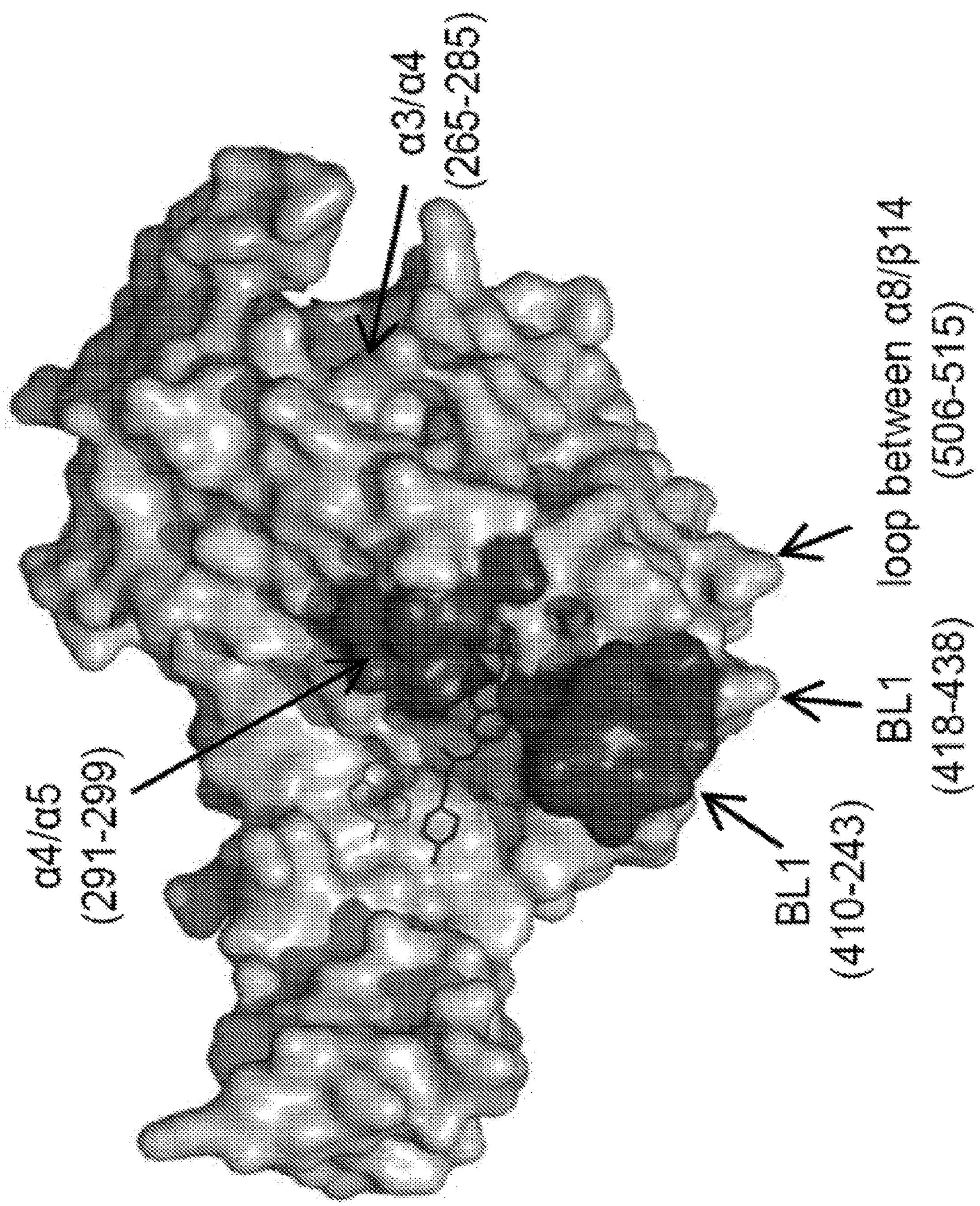
FIG. 3C: Molecular surface representation of the USP7·compound 10 co-structure. Highlighted regions indicate regions of altered HDX in the presence of compound 10. Darker areas correspond to significant changes whereas lighter areas correspond to regions with subtle changes.
Figure 4A:
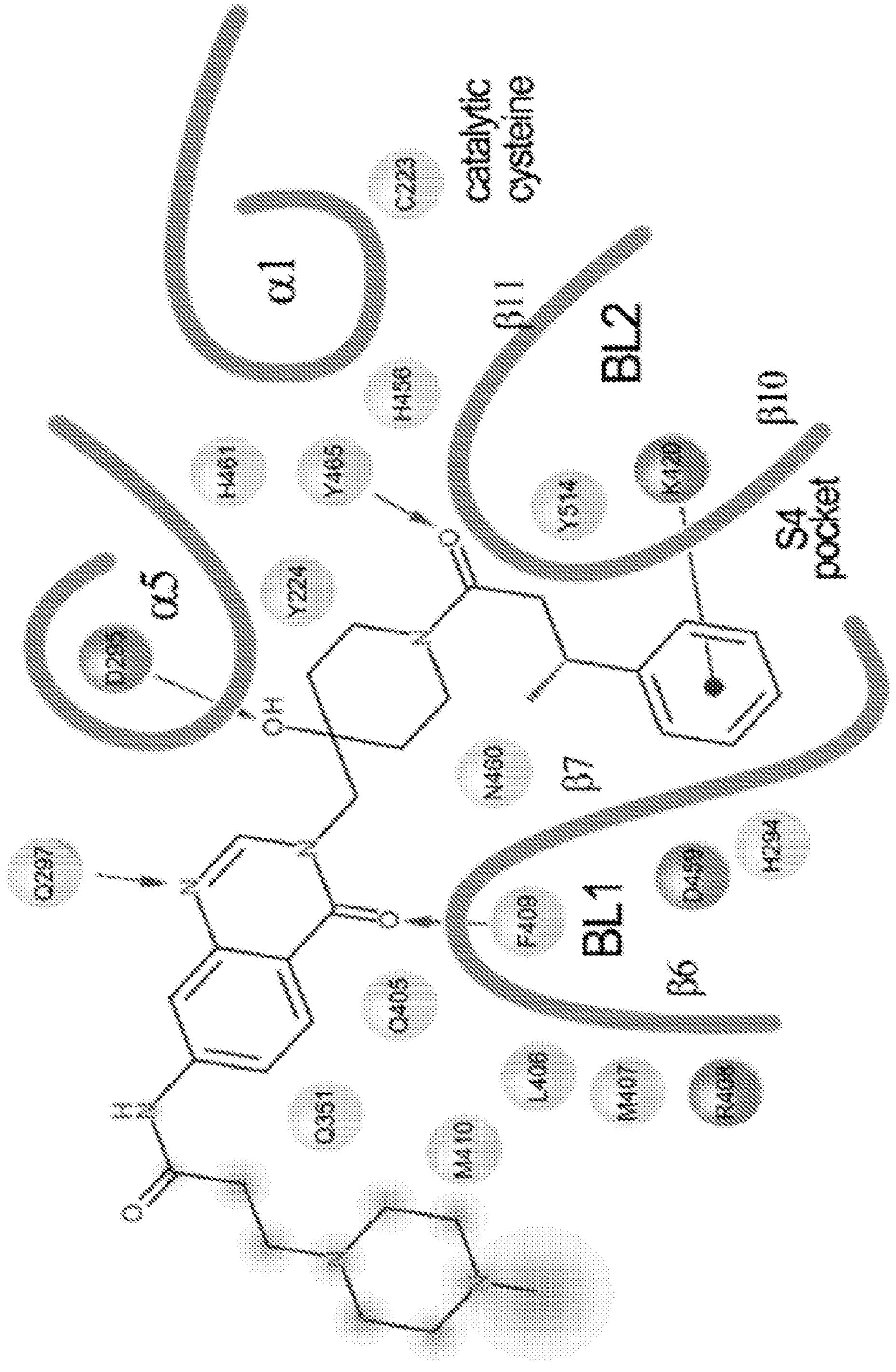
FIG. 4A: Analysis of USP7 mutant proteins. Detailed ligand interaction diagram of compound 10 with USP7. Residues for which >80% of other USPs contain an amino acid belonging to the same class are boxed red.
Figures 4B, 4C:
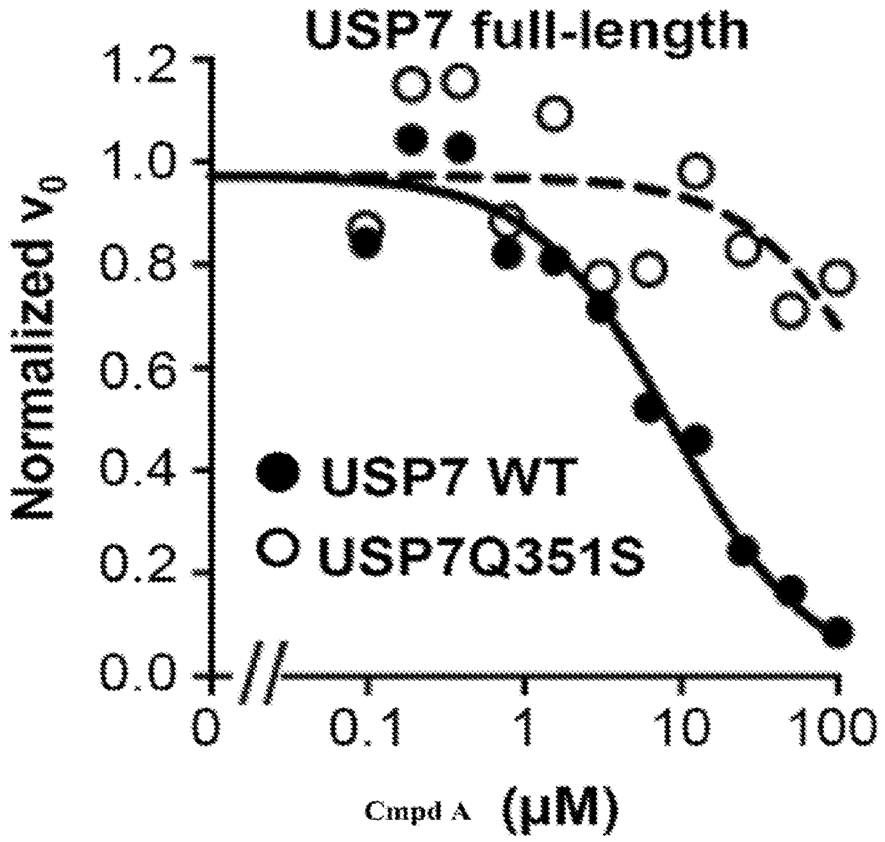
FIG. 4B: Summary of activity against Ub-AMC and inhibition by compound A for USP7 mutant catalytic domain proteins.
FIG. 4C: Dose-response inhibition of full length USP7Q351 (amino acids 1-1102) by compound A.
Figure 4D:
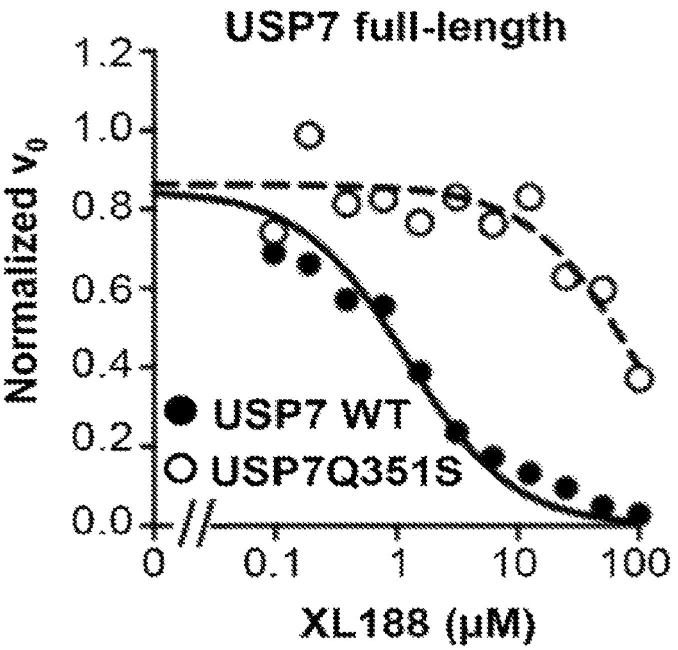
FIG. 4D: Dose-response inhibition of full length USP7Q351 (amino acids 1-1102) by compound 10.

FIGS. 3A-C illustrate the binding of compound 10 to USP7. FIGS. 4A-D illustrate the binding and dose response inhibition of compounds A and 10. FIGS. 5A-C illustrate the microsome stability and the USP7 binding ability of compound A and the presently disclosed compounds.

Table 3: USP7 activity of exemplary compounds in USP7 assay. ++++ indicates an $IC_{50}$ of less than about 0. μM, +++ indicates an $IC_{50}$ from about 0.2 μM to about 1 μM, ++ indicates an $IC_{50}$ from about 1 μM to about 1 μM, and + indicates an $IC_{50}$ greater than 1 μM. ND refers to not disclosed.

TABLE 3

| Compound | $IC_{50}$ (μM) |
|---|---|
| 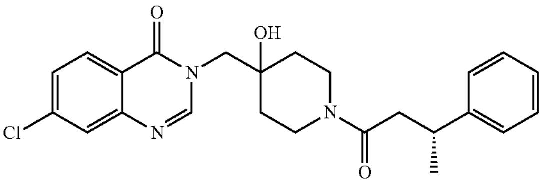 [SMILES: C[C@H](CC(=O)N1CCC(O)(Cn2cnc3cc(Cl)ccc3c2=O)CC1)c1ccccc1]<br>1 | ++++ |
| 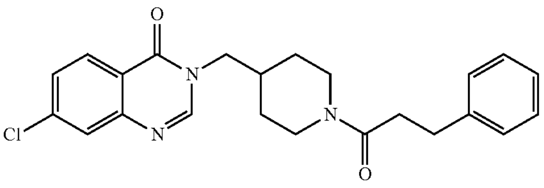 [SMILES: O=C(CCc1ccccc1)N1CCC(Cn2cnc3cc(Cl)ccc3c2=O)CC1]<br>2 | ++++ |

TABLE 3-continued
| Compound | $IC_{50}$ (μM) |
| --- | --- |
| 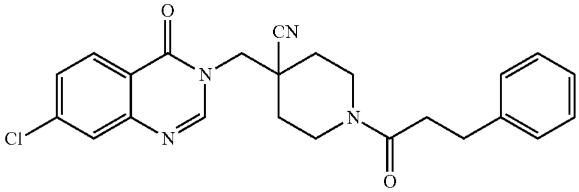 [SMILES: N#CC1(Cn2cnc3cc(Cl)ccc3c2=O)CCN(C(=O)CCc2ccccc2)CC1] 3 | ND |
| 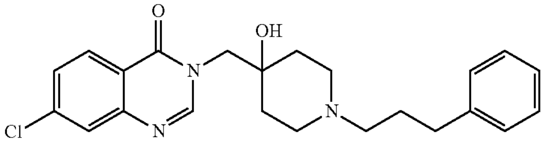 [SMILES: O=c1c2ccc(Cl)cc2ncn1CC1(O)CCN(CCCc2ccccc2)CC1] 4 | + |
| 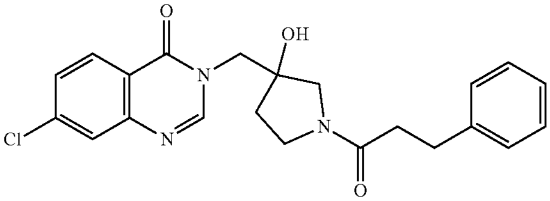 [SMILES: O=C(CCc1ccccc1)N1CCC(O)(Cn2cnc3cc(Cl)ccc3c2=O)C1] 5 | + |
| 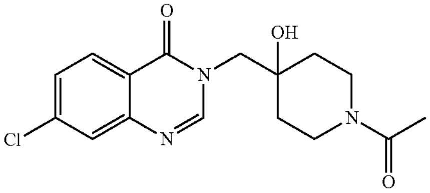 [SMILES: CC(=O)N1CCC(O)(Cn2cnc3cc(Cl)ccc3c2=O)CC1] 6 | + |
| 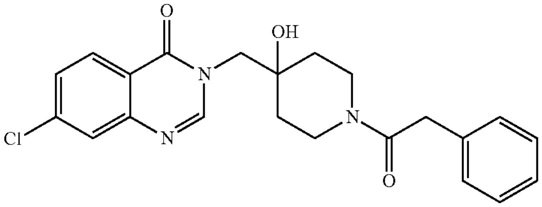 [SMILES: O=C(Cc1ccccc1)N1CCC(O)(Cn2cnc3cc(Cl)ccc3c2=O)CC1] 7 | + |
| 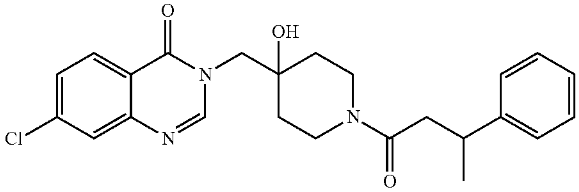 [SMILES: CC(CC(=O)N1CCC(O)(Cn2cnc3cc(Cl)ccc3c2=O)CC1)c1ccccc1] 8 | ++++ |
| 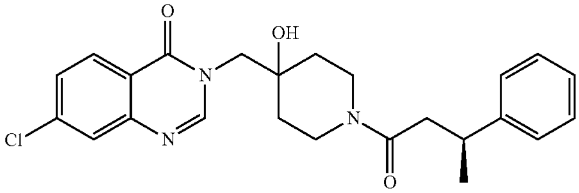 [SMILES: C[C@@H](CC(=O)N1CCC(O)(Cn2cnc3cc(Cl)ccc3c2=O)CC1)c1ccccc1] 9 | ++++ |

TABLE 3-continued
| Compound | $IC_{50}$ (μM) |
|---|---|
| 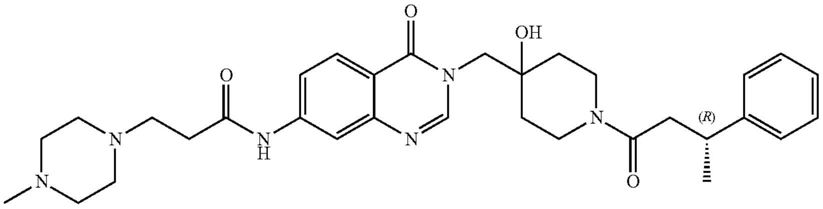 10 | ++++ |
| 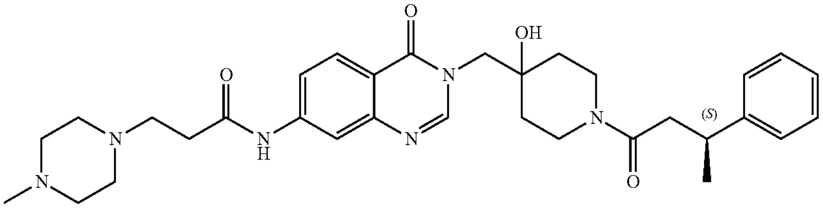 11 | ++++ |
| 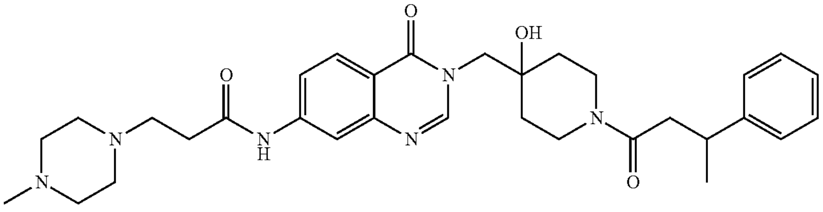 [SMILES: CC(CC(=O)N1CCC(O)(Cn2cnc3cc(NC(=O)CCN4CCN(C)CC4)ccc3c2=O)CC1)c1ccccc1] 12 | +++ |
| 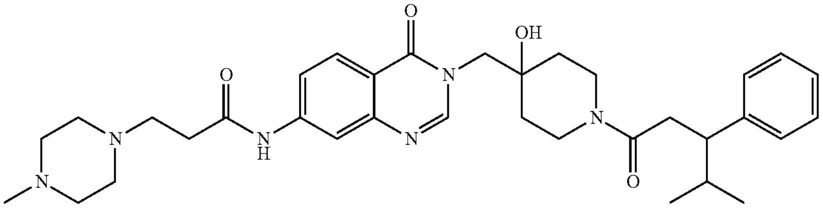 [SMILES: CC(C)C(CC(=O)N1CCC(O)(Cn2cnc3cc(NC(=O)CCN4CCN(C)CC4)ccc3c2=O)CC1)c1ccccc1] 13 | +++ |
| 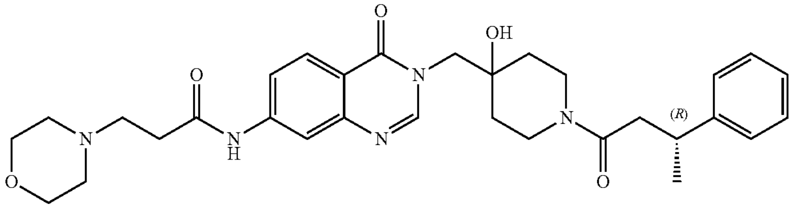 14 | ++++ |
| 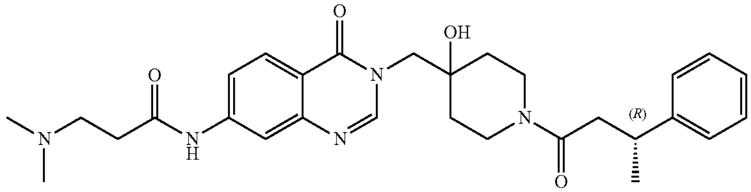 15 | ++++ |

TABLE 3-continued
| Compound | IC50 (μM) |
|---|---|
| 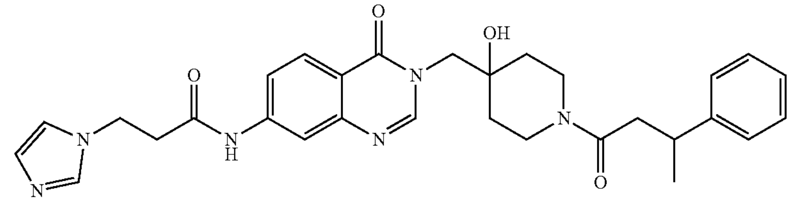 [SMILES: CC(CC(=O)N1CCC(O)(Cn2cnc3cc(NC(=O)CCn4ccnc4)ccc3c2=O)CC1)c1ccccc1] 16 | ++++ |
| 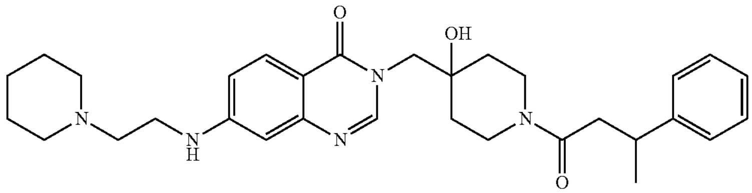 [SMILES: CC(CC(=O)N1CCC(O)(Cn2cnc3cc(NCCN4CCCCC4)ccc3c2=O)CC1)c1ccccc1] 17 | ++++ |
| 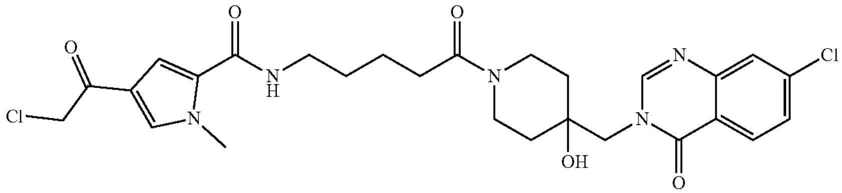 [SMILES: Cn1cc(C(=O)CCl)cc1C(=O)NCCCCC(=O)N1CCC(O)(Cn2cnc3cc(Cl)ccc3c2=O)CC1] 18 | ++ |
| 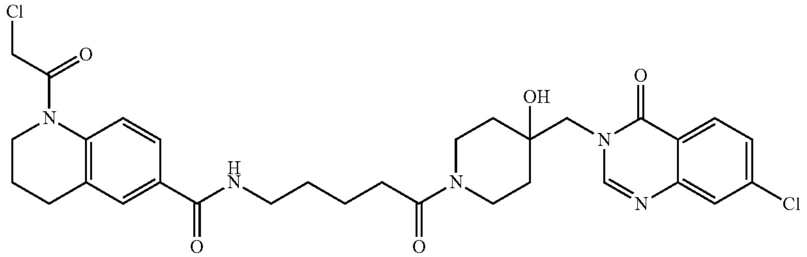 [SMILES: O=C(NCCCCC(=O)N1CCC(O)(Cn2cnc3cc(Cl)ccc3c2=O)CC1)c1ccc2c(c1)CCCN2C(=O)CCl] 19 | ++ |
| 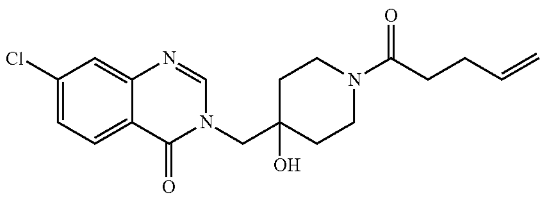 [SMILES: C=CCCC(=O)N1CCC(O)(Cn2cnc3cc(Cl)ccc3c2=O)CC1] 20 | + |
| 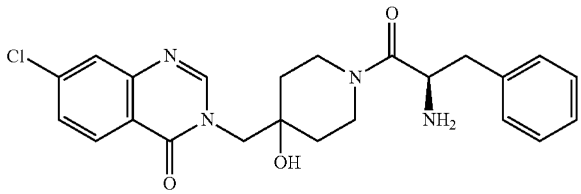 [SMILES: N[C@H](Cc1ccccc1)C(=O)N1CCC(O)(Cn2cnc3cc(Cl)ccc3c2=O)CC1] 21 | + |

TABLE 3-continued
| Compound | $IC_{50}$ (μM) |
|---|---|
| 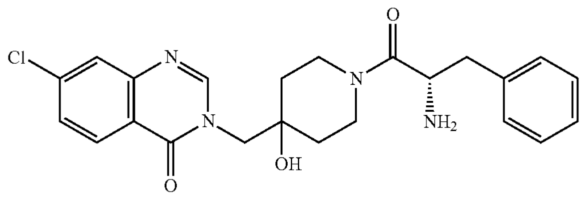 [SMILES: N[C@@H](Cc1ccccc1)C(=O)N1CCC(O)(Cn2cnc3cc(Cl)ccc3c2=O)CC1]<br>22 | + |
| 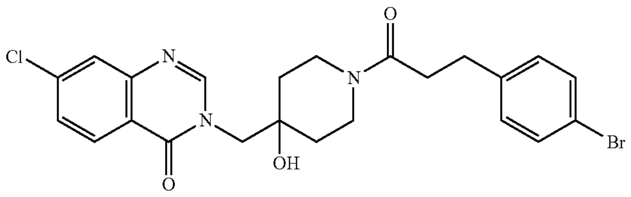 [SMILES: O=C(CCc1ccc(Br)cc1)N1CCC(O)(Cn2cnc3cc(Cl)ccc3c2=O)CC1]<br>23 | + |
| 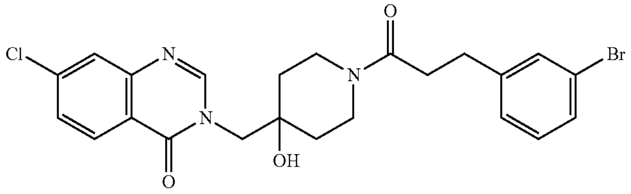 [SMILES: O=C(CCc1cccc(Br)c1)N1CCC(O)(Cn2cnc3cc(Cl)ccc3c2=O)CC1]<br>24 | + |
| 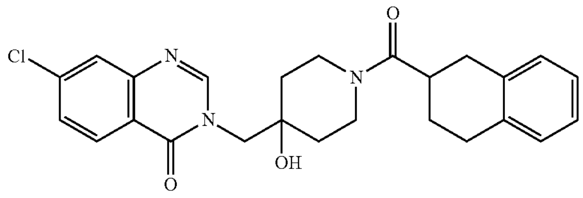 [SMILES: O=C(C1CCc2ccccc2C1)N1CCC(O)(Cn2cnc3cc(Cl)ccc3c2=O)CC1]<br>25 | + |
| 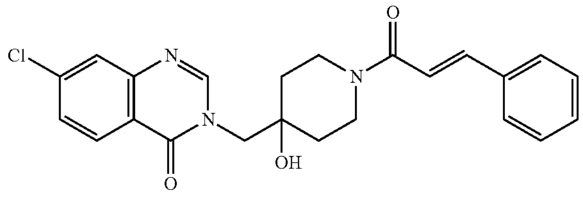 [SMILES: O=C(/C=C/c1ccccc1)N1CCC(O)(Cn2cnc3cc(Cl)ccc3c2=O)CC1]<br>26 | + |
| 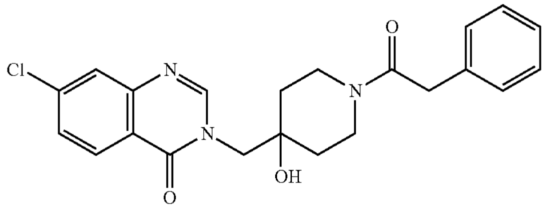 [SMILES: O=C(Cc1ccccc1)N1CCC(O)(Cn2cnc3cc(Cl)ccc3c2=O)CC1]<br>27 | + |
| 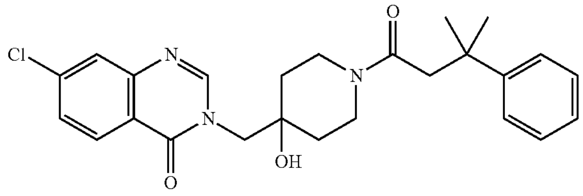 [SMILES: CC(C)(CC(=O)N1CCC(O)(Cn2cnc3cc(Cl)ccc3c2=O)CC1)c1ccccc1]<br>28 | + |

TABLE 3-continued
| Compound | IC50 (μM) |
|---|---|
| 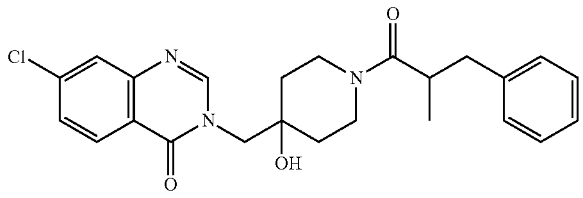 [SMILES: CC(Cc1ccccc1)C(=O)N1CCC(O)(Cn2cnc3cc(Cl)ccc3c2=O)CC1] 29 | +++ |
| 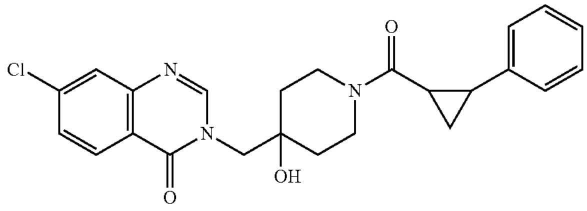 [SMILES: O=C(C1CC1c1ccccc1)N1CCC(O)(Cn2cnc3cc(Cl)ccc3c2=O)CC1] 30 | ++ |
| 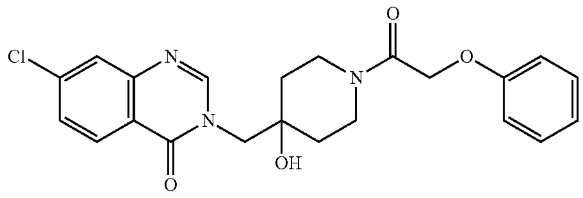 [SMILES: O=C(COc1ccccc1)N1CCC(O)(Cn2cnc3cc(Cl)ccc3c2=O)CC1] 31 | + |
| 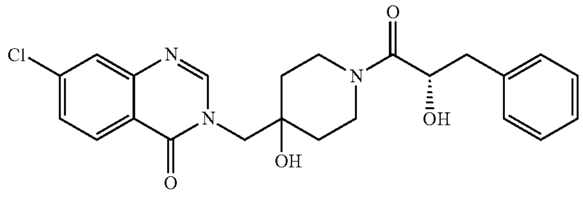 [SMILES: O=C([C@@H](O)Cc1ccccc1)N1CCC(O)(Cn2cnc3cc(Cl)ccc3c2=O)CC1] 32 | + |
| 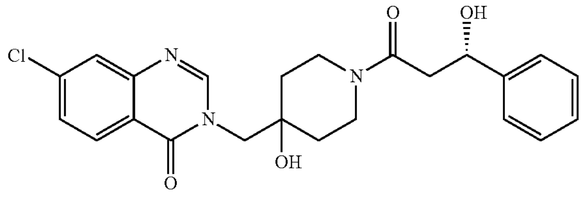 [SMILES: O=C(C[C@H](O)c1ccccc1)N1CCC(O)(Cn2cnc3cc(Cl)ccc3c2=O)CC1] 33 | + |
| 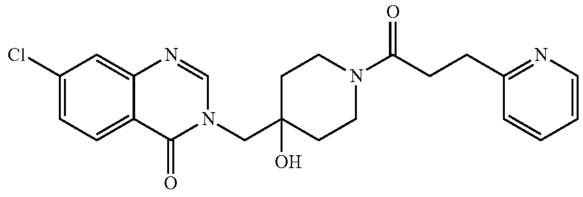 [SMILES: O=C(CCc1ccccn1)N1CCC(O)(Cn2cnc3cc(Cl)ccc3c2=O)CC1] 34 | + |
| 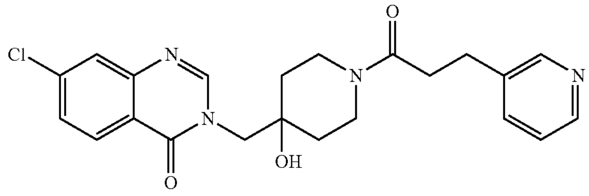 [SMILES: O=C(CCc1cccnc1)N1CCC(O)(Cn2cnc3cc(Cl)ccc3c2=O)CC1] 35 | + |

TABLE 3-continued
| Compound | $IC_{50}$ (μM) |
| --- | --- |
| 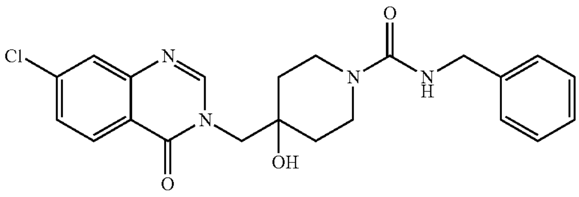 [SMILES: O=C(NCc1ccccc1)N1CCC(O)(Cn2cnc3cc(Cl)ccc3c2=O)CC1] 36 | + |
| 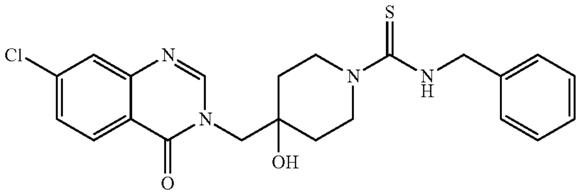 [SMILES: O=c1c2ccc(Cl)cc2ncn1CC1(O)CCN(C(=S)NCc2ccccc2)CC1] 37 | + |
| 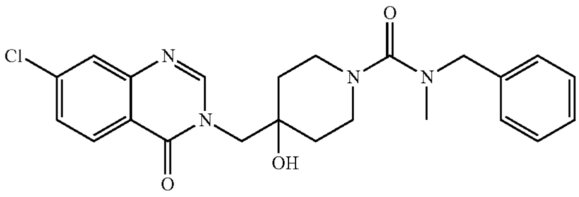 [SMILES: CN(Cc1ccccc1)C(=O)N1CCC(O)(Cn2cnc3cc(Cl)ccc3c2=O)CC1] 38 | +++ |
| 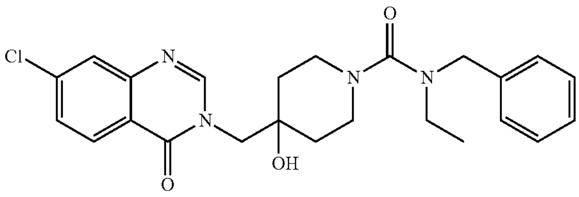 [SMILES: CCN(Cc1ccccc1)C(=O)N1CCC(O)(Cn2cnc3cc(Cl)ccc3c2=O)CC1] 39 | +++ |
| 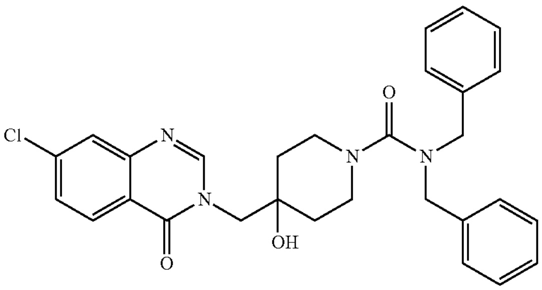 [SMILES: O=C(N1CCC(O)(Cn2cnc3cc(Cl)ccc3c2=O)CC1)N(Cc1ccccc1)Cc1ccccc1] 40 | + |
| 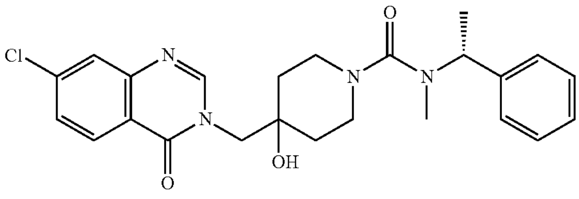 [SMILES: C[C@H](c1ccccc1)N(C)C(=O)N1CCC(O)(Cn2cnc3cc(Cl)ccc3c2=O)CC1] 41 | + |

TABLE 3-continued
| Compound | $IC_{50}$ (μM) |
|---|---|
| 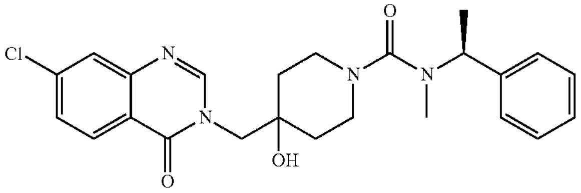 [SMILES: C[C@@H](c1ccccc1)N(C)C(=O)N1CCC(O)(Cn2cnc3cc(Cl)ccc3c2=O)CC1] 42 | + |
| 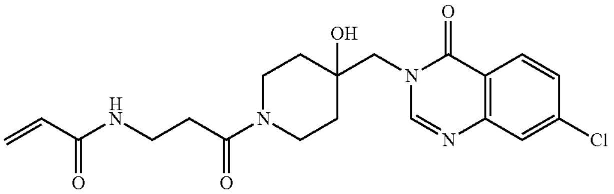 [SMILES: C=CC(=O)NCCC(=O)N1CCC(O)(Cn2cnc3cc(Cl)ccc3c2=O)CC1] 43 | ND |
| 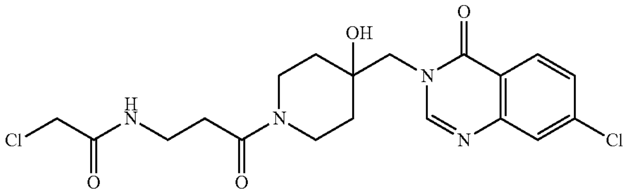 [SMILES: O=C(CCl)NCCC(=O)N1CCC(O)(Cn2cnc3cc(Cl)ccc3c2=O)CC1] 44 | + |
| 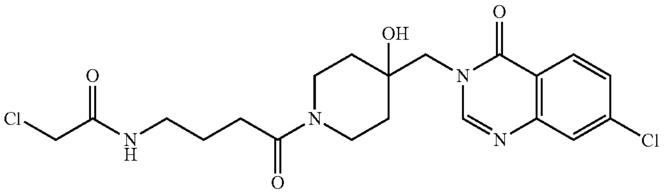 [SMILES: O=C(CCl)NCCCC(=O)N1CCC(O)(Cn2cnc3cc(Cl)ccc3c2=O)CC1] 45 | ND |
| 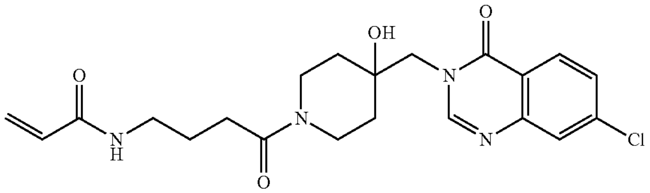 [SMILES: C=CC(=O)NCCCC(=O)N1CCC(O)(Cn2cnc3cc(Cl)ccc3c2=O)CC1] 46 | + |
| 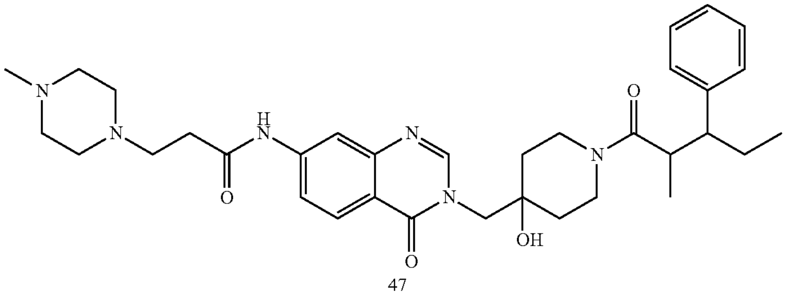 47 | ++++ |

TABLE 3-continued
| Compound | $IC_{50}$ (μM) |
|---|---|
| 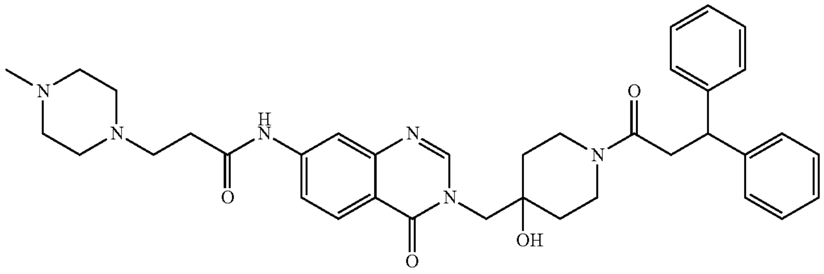 [SMILES: CN1CCN(CCC(=O)Nc2ccc3c(=O)n(CC4(O)CCN(C(=O)CC(c5ccccc5)c5ccccc5)CC4)cnc3c2)CC1] 48 | ++++ |
| 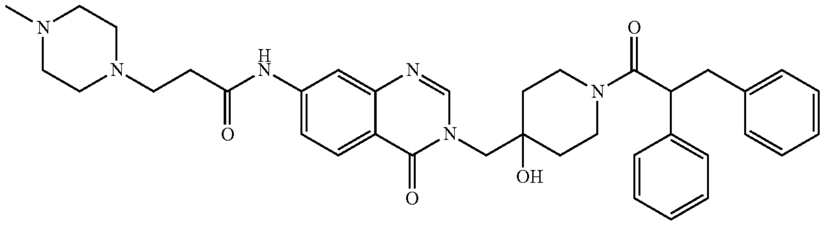 [SMILES: CN1CCN(CCC(=O)Nc2ccc3c(=O)n(CC4(O)CCN(C(=O)C(Cc5ccccc5)c5ccccc5)CC4)cnc3c2)CC1] 49 | + |
| 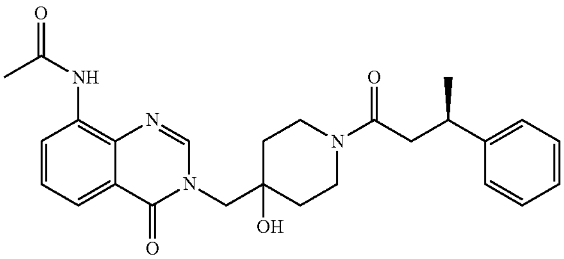 [SMILES: CC(=O)Nc1cccc2c(=O)n(CC3(O)CCN(C(=O)C[C@@H](C)c4ccccc4)CC3)cnc12] 50 | ++ |
| 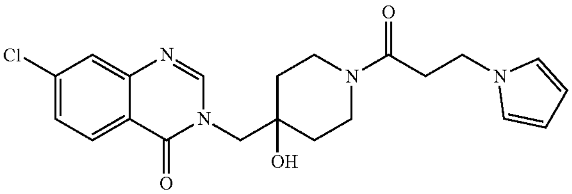 [SMILES: O=C(CCn1cccc1)N1CCC(O)(Cn2cnc3cc(Cl)ccc3c2=O)CC1] 51 | + |
| 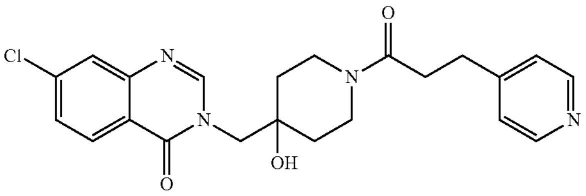 [SMILES: O=C(CCc1ccncc1)N1CCC(O)(Cn2cnc3cc(Cl)ccc3c2=O)CC1] 52 | + |
| 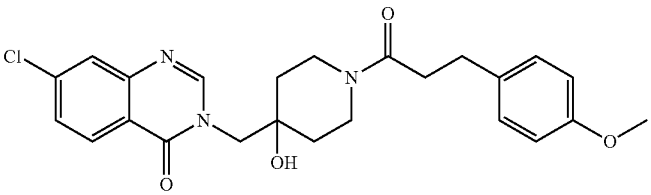 [SMILES: COc1ccc(CCC(=O)N2CCC(O)(Cn3cnc4cc(Cl)ccc4c3=O)CC2)cc1] 53 | + |

TABLE 3-continued
| Compound | $IC_{50}$ (μM) |
|---|---|
| 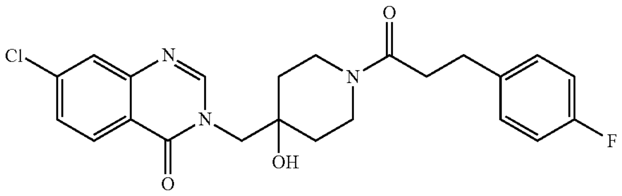 [SMILES: O=C(CCc1ccc(F)cc1)N1CCC(O)(Cn2cnc3cc(Cl)ccc3c2=O)CC1] 54 | +++ |
| 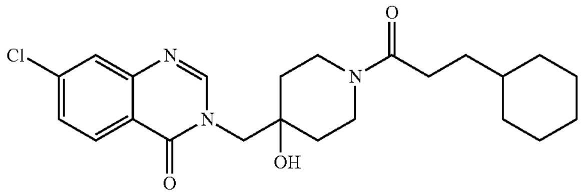 [SMILES: O=C(CCC1CCCCC1)N1CCC(O)(Cn2cnc3cc(Cl)ccc3c2=O)CC1] 55 | + |
| 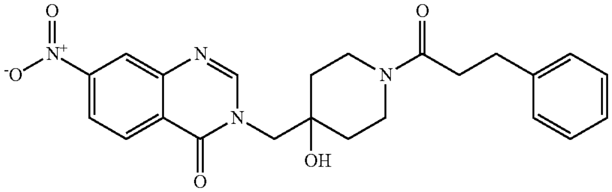 56 | + |
| 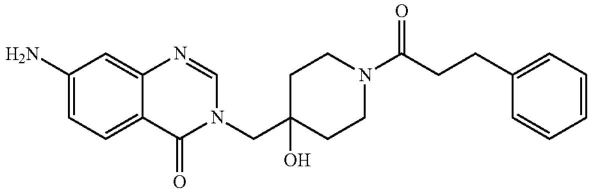 [SMILES: Nc1ccc2c(=O)n(CC3(O)CCN(C(=O)CCc4ccccc4)CC3)cnc2c1] 57 | + |
| 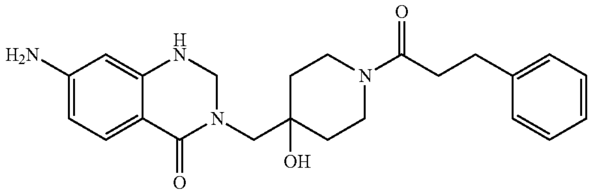 [SMILES: Nc1ccc2c(c1)NCN(CC1(O)CCN(C(=O)CCc3ccccc3)CC1)C2=O] 58 | + |

TABLE 3-continued
| Compound | $IC_{50}$ (μM) |
|---|---|
| 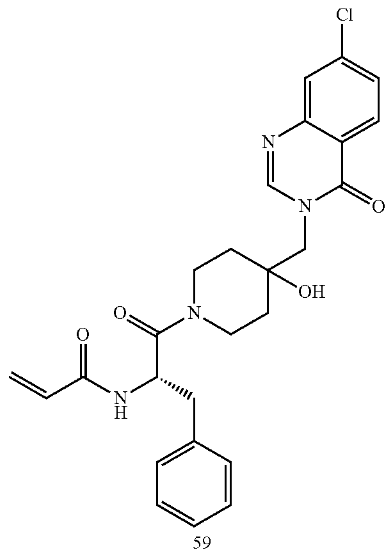 59 | + |
| 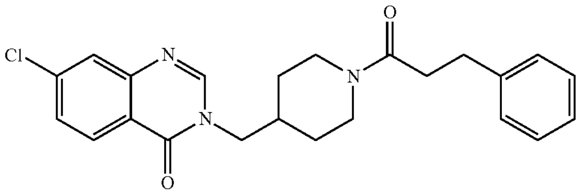 [SMILES: O=C(CCc1ccccc1)N1CCC(Cn2cnc3cc(Cl)ccc3c2=O)CC1] 60 | + |
| 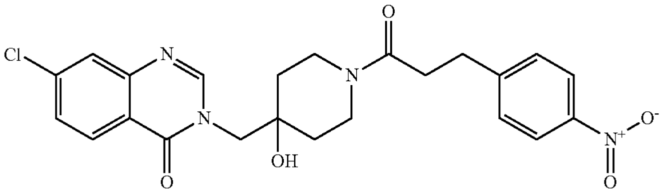 [SMILES: O=C(CCc1ccc([N+](=O)[O-])cc1)N1CCC(O)(Cn2cnc3cc(Cl)ccc3c2=O)CC1] 61 | + |
| 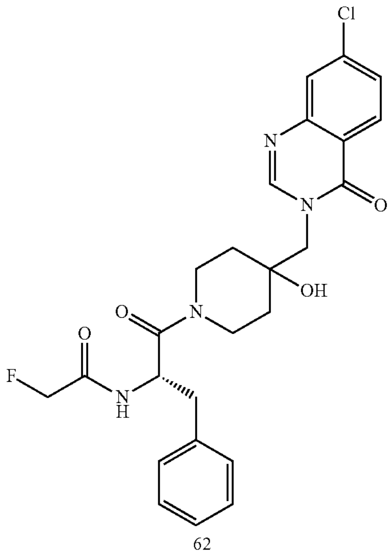 62 | + |

TABLE 3-continued
| Compound | $IC_{50}$ (μM) |
| --- | --- |
| 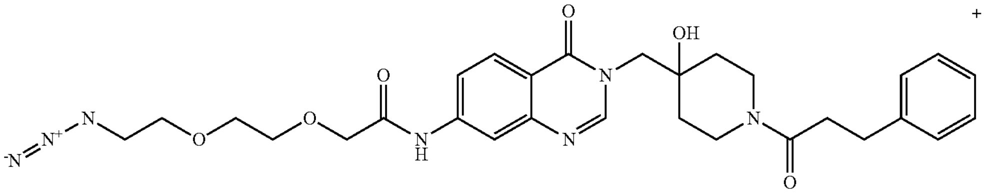 63 | + |
| 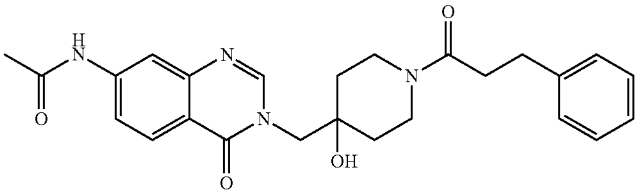 [SMILES: CC(=O)Nc1ccc2c(=O)n(CC3(O)CCN(C(=O)CCc4ccccc4)CC3)cnc2c1] 64 | ++ |
| 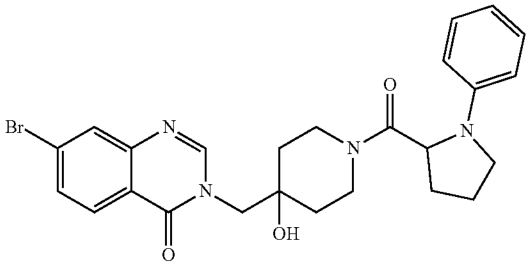 [SMILES: O=C(C1CCCN1c1ccccc1)N1CCC(O)(Cn2cnc3cc(Br)ccc3c2=O)CC1] 65 | + |
| 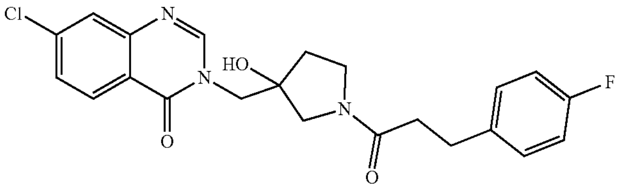 [SMILES: O=C(CCc1ccc(F)cc1)N1CCC(O)(Cn2cnc3cc(Cl)ccc3c2=O)C1] 66 | + |
| 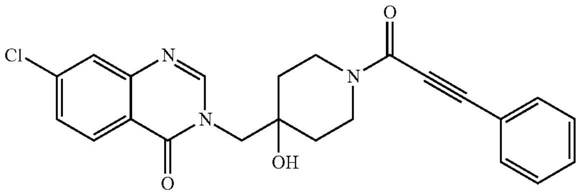 [SMILES: O=C(C#Cc1ccccc1)N1CCC(O)(Cn2cnc3cc(Cl)ccc3c2=O)CC1] 67 | + |
| 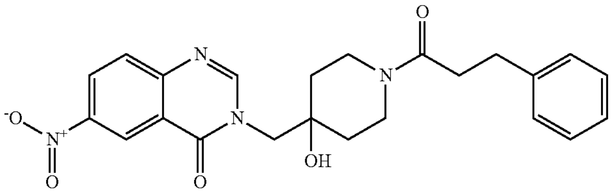 68 | + |

TABLE 3-continued
| Compound | $IC_{50}$ (μM) |
|---|---|
| 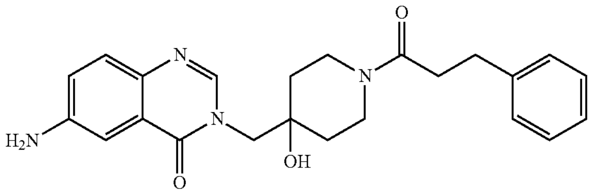 [SMILES: Nc1ccc2ncn(CC3(O)CCN(C(=O)CCc4ccccc4)CC3)c(=O)c2c1] 69 | + |
| 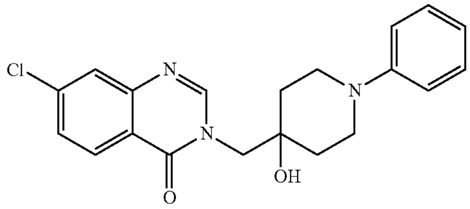 [SMILES: O=c1c2ccc(Cl)cc2ncn1CC1(O)CCN(c2ccccc2)CC1] 70 | + |
| 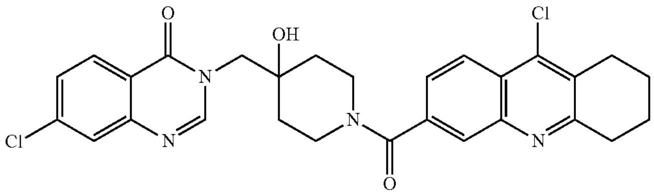 [SMILES: O=C(c1ccc2c(Cl)c3c(nc2c1)CCCC3)N1CCC(O)(Cn2cnc3cc(Cl)ccc3c2=O)CC1] 71 | + |
| 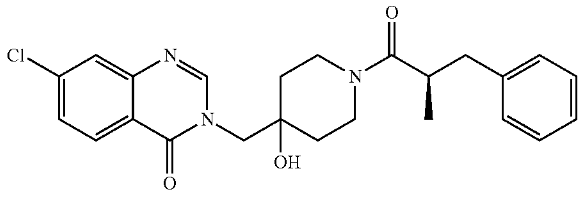 [SMILES: C[C@H](Cc1ccccc1)C(=O)N1CCC(O)(Cn2cnc3cc(Cl)ccc3c2=O)CC1] 72 | +++ |
| 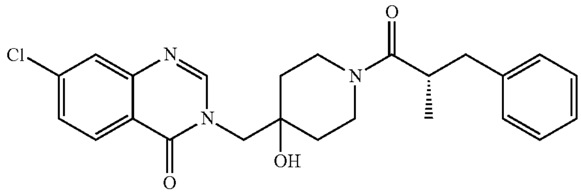 [SMILES: C[C@@H](Cc1ccccc1)C(=O)N1CCC(O)(Cn2cnc3cc(Cl)ccc3c2=O)CC1] 73 | + |
| 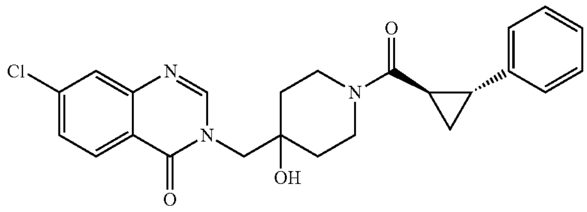 [SMILES: O=C([C@@H]1C[C@H]1c1ccccc1)N1CCC(O)(Cn2cnc3cc(Cl)ccc3c2=O)CC1] 74 | + |
| 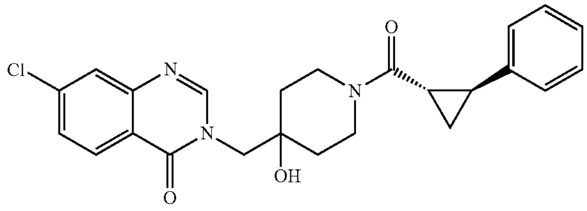 [SMILES: O=C([C@H]1C[C@@H]1c1ccccc1)N1CCC(O)(Cn2cnc3cc(Cl)ccc3c2=O)CC1] 75 | + |

TABLE 3-continued
| Compound | $IC_{50}$ (μM) |
|---|---|
| 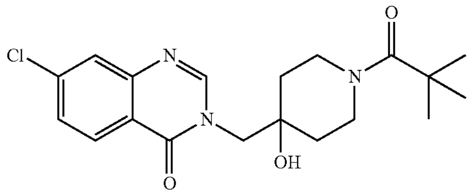 [SMILES: CC(C)(C)C(=O)N1CCC(O)(Cn2cnc3cc(Cl)ccc3c2=O)CC1] 76 | + |
| 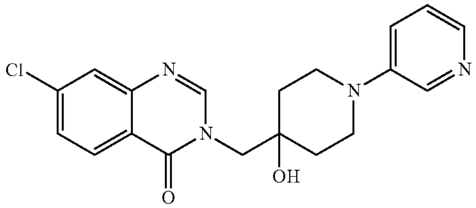 [SMILES: O=c1c2ccc(Cl)cc2ncn1CC1(O)CCN(c2cccnc2)CC1] 77 | + |
| 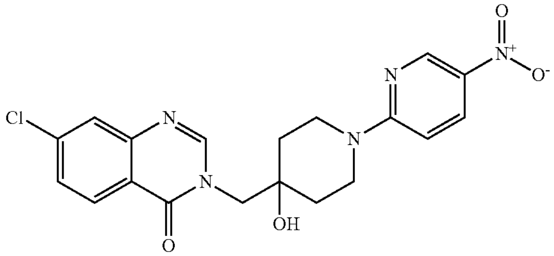 [SMILES: O=c1c2ccc(Cl)cc2ncn1CC1(O)CCN(c2ccc([N+](=O)[O-])cn2)CC1] 78 | + |
| 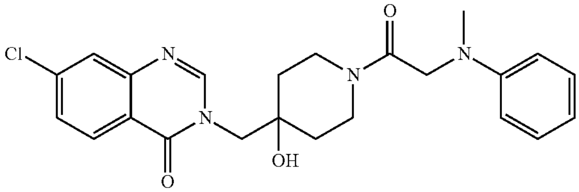 [SMILES: CN(CC(=O)N1CCC(O)(Cn2cnc3cc(Cl)ccc3c2=O)CC1)c1ccccc1] 79 | + |
| 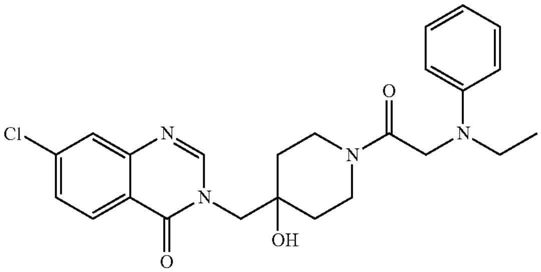 [SMILES: CCN(CC(=O)N1CCC(O)(Cn2cnc3cc(Cl)ccc3c2=O)CC1)c1ccccc1] 80 | + |
| 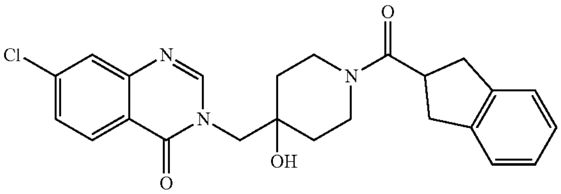 [SMILES: O=C(C1Cc2ccccc2C1)N1CCC(O)(Cn2cnc3cc(Cl)ccc3c2=O)CC1] 81 | + |

TABLE 3-continued
| Compound | $IC_{50}$ (μM) |
|---|---|
| 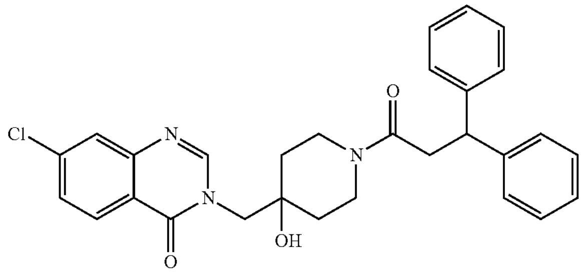 [SMILES: O=C(CC(c1ccccc1)c1ccccc1)N1CCC(O)(Cn2cnc3cc(Cl)ccc3c2=O)CC1] 82 | ++ |
| 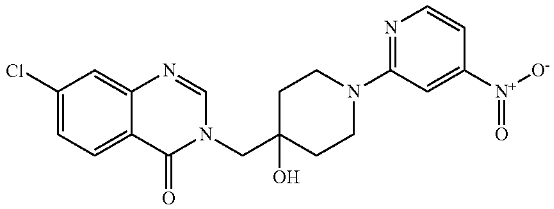 [SMILES: O=c1c2ccc(Cl)cc2ncn1CC1(O)CCN(c2cc([N+](=O)[O-])ccn2)CC1] 83 | + |
| 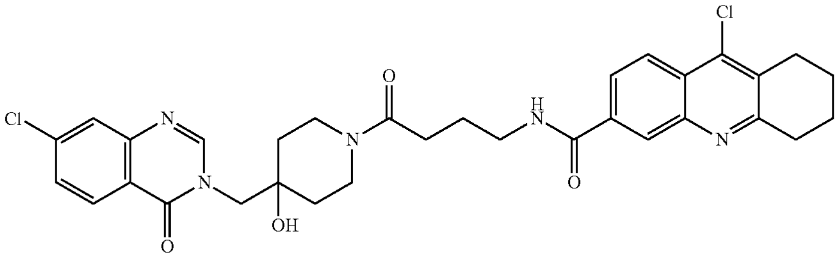 [SMILES: O=C(NCCCC(=O)N1CCC(O)(Cn2cnc3cc(Cl)ccc3c2=O)CC1)c1ccc2c(Cl)c3c(nc2c1)CCCC3] 84 | ++ |
| 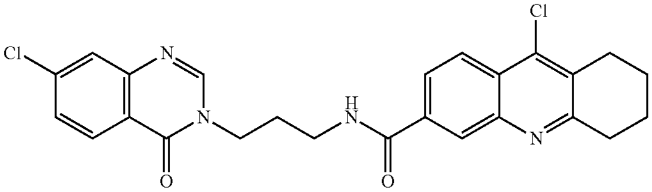 [SMILES: O=C(NCCCn1cnc2cc(Cl)ccc2c1=O)c1ccc2c(Cl)c3c(nc2c1)CCCC3] 85 | + |
| 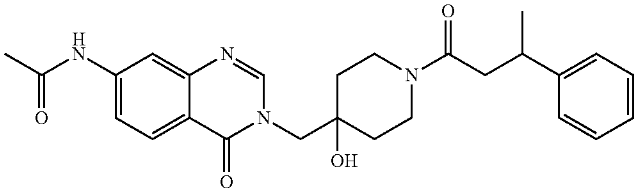 [SMILES: CC(=O)Nc1ccc2c(=O)n(CC3(O)CCN(C(=O)CC(C)c4ccccc4)CC3)cnc2c1] 86 | +++ |
| 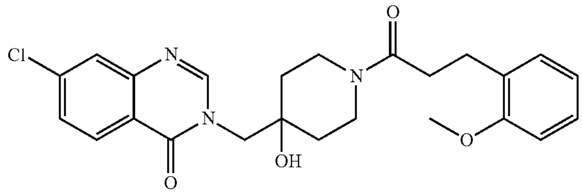 [SMILES: COc1ccccc1CCC(=O)N1CCC(O)(Cn2cnc3cc(Cl)ccc3c2=O)CC1] 87 | + |

TABLE 3-continued
| Compound | IC50 (μM) |
| --- | --- |
| 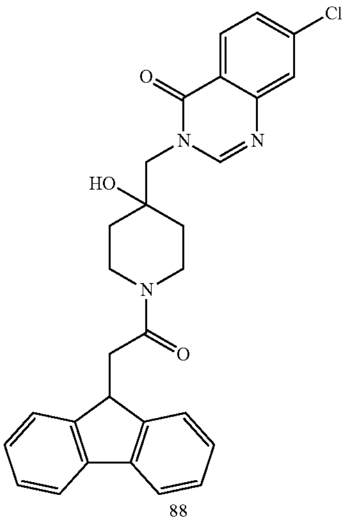 88 | + |
| 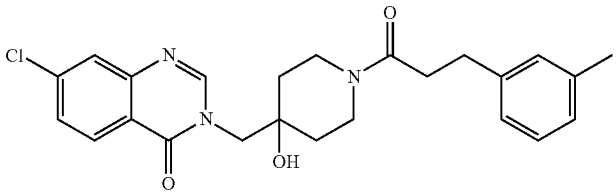 [SMILES: Cc1cccc(CCC(=O)N2CCC(O)(Cn3cnc4cc(Cl)ccc4c3=O)CC2)c1] 89 | + |
| 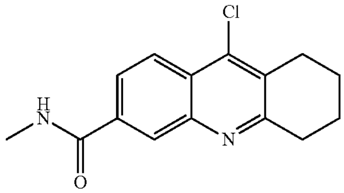 [SMILES: CNC(=O)c1ccc2c(Cl)c3c(nc2c1)CCCC3] 90 | + |
| 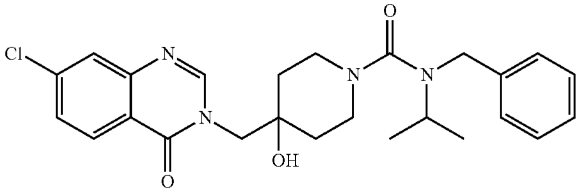 [SMILES: CC(C)N(Cc1ccccc1)C(=O)N1CCC(O)(Cn2cnc3cc(Cl)ccc3c2=O)CC1] 91 | +++ |
| 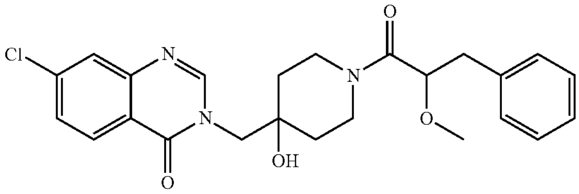 [SMILES: COC(Cc1ccccc1)C(=O)N1CCC(O)(Cn2cnc3cc(Cl)ccc3c2=O)CC1] 92 | ++ |

TABLE 3-continued
| Compound | $IC_{50}$ (μM) |
|---|---|
| 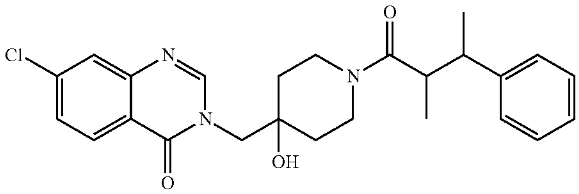 [SMILES: CC(C(=O)N1CCC(O)(Cn2cnc3cc(Cl)ccc3c2=O)CC1)C(C)c1ccccc1] 93 | ++ |
| 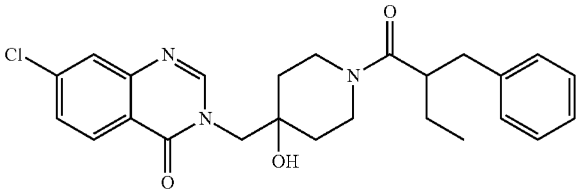 [SMILES: CCC(Cc1ccccc1)C(=O)N1CCC(O)(Cn2cnc3cc(Cl)ccc3c2=O)CC1] 94 | ++ |
| 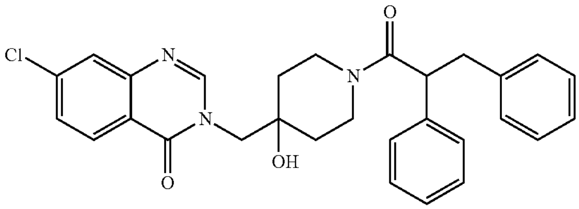 [SMILES: O=C(C(Cc1ccccc1)c1ccccc1)N1CCC(O)(Cn2cnc3cc(Cl)ccc3c2=O)CC1] 95 | + |
| 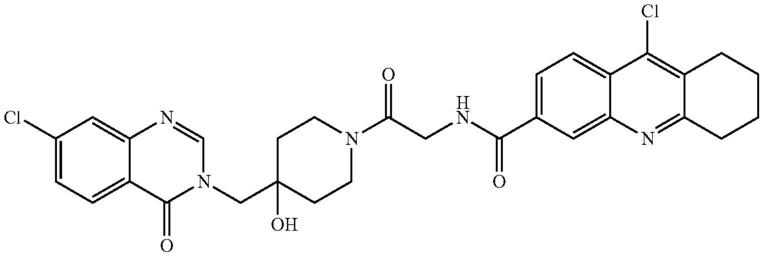 [SMILES: O=C(NCC(=O)N1CCC(O)(Cn2cnc3cc(Cl)ccc3c2=O)CC1)c1ccc2c(Cl)c3c(nc2c1)CCCC3] 96 | + |
| 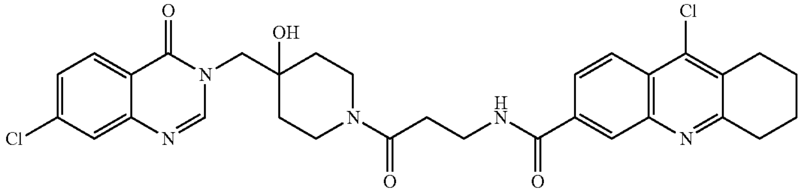 [SMILES: O=C(NCCC(=O)N1CCC(O)(Cn2cnc3cc(Cl)ccc3c2=O)CC1)c1ccc2c(Cl)c3c(nc2c1)CCCC3] 97 | + |
| 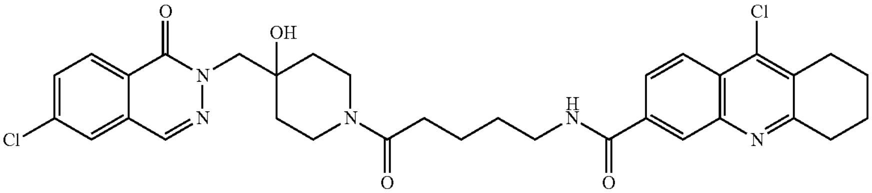 [SMILES: O=C(NCCCCC(=O)N1CCC(O)(Cn2ncc3cc(Cl)ccc3c2=O)CC1)c1ccc2c(Cl)c3c(nc2c1)CCCC3] 98 | +++ |

TABLE 3-continued
| Compound | $IC_{50}$ (μM) |
|---|---|
| 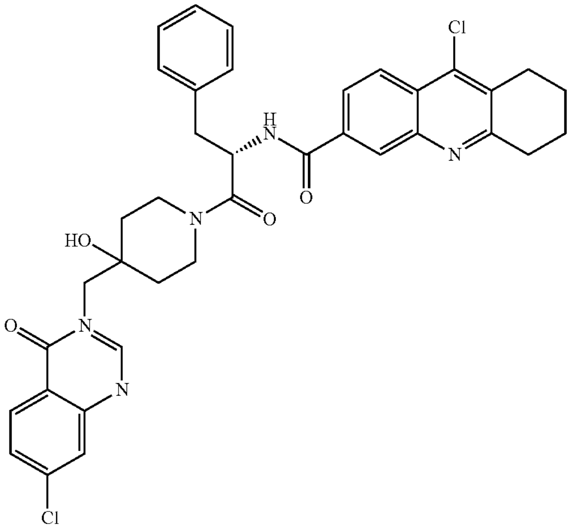 99 | ++ |
| 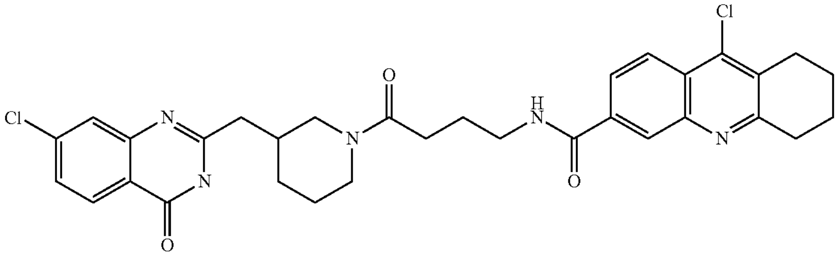 [SMILES: O=C(NCCCC(=O)N1CCCC(Cc2nc3cc(Cl)ccc3c(=O)[nH]2)C1)c1ccc2c(Cl)c3c(nc2c1)CCCC3] 100 | + |
| 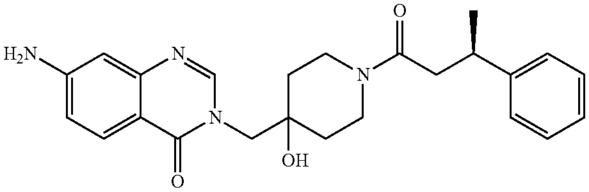 [SMILES: C[C@H](CC(=O)N1CCC(O)(Cn2cnc3cc(N)ccc3c2=O)CC1)c1ccccc1] 101 | +++ |
| 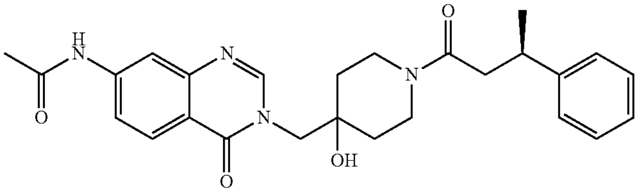 [SMILES: CC(=O)Nc1ccc2c(=O)n(CC3(O)CCN(C(=O)C[C@@H](C)c4ccccc4)CC3)cnc2c1] 102 | +++ |
| 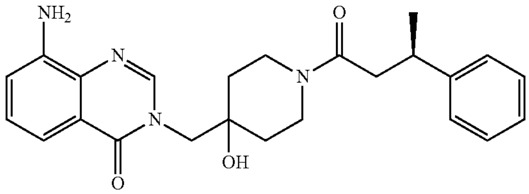 [SMILES: C[C@H](CC(=O)N1CCC(O)(Cn2cnc3c(N)cccc3c2=O)CC1)c1ccccc1] 103 | ++ |

TABLE 3-continued
| Compound | $IC_{50}$ (μM) |
| --- | --- |
| 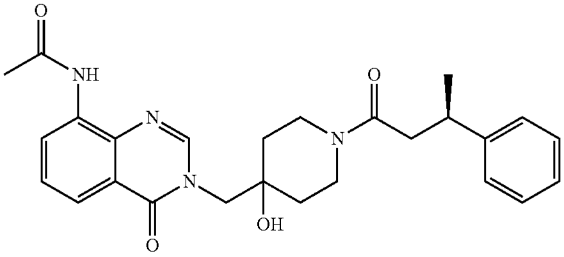 [SMILES: CC(=O)Nc1cccc2c(=O)n(CC3(O)CCN(C(=O)C[C@@H](C)c4ccccc4)CC3)cnc12] 104 | ++ |
| 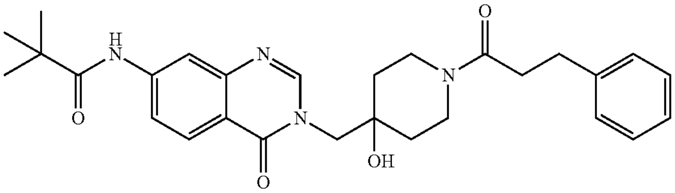 [SMILES: CC(C)(C)C(=O)Nc1ccc2c(=O)n(CC3(O)CCN(C(=O)CCc4ccccc4)CC3)cnc2c1] 105 | + |
Further exemplary compounds include, but are not limited to, those given in Table 4 below.
TABLE 4
| Compound |
| --- |
| 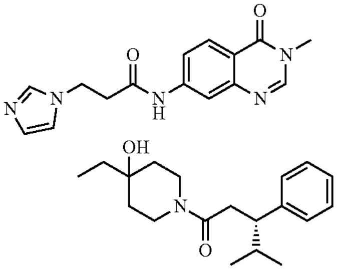 106 |
| 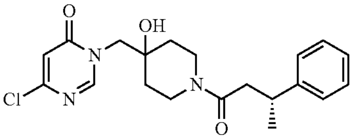 [SMILES: C[C@H](CC(=O)N1CCC(O)(Cn2cnc(Cl)cc2=O)CC1)c1ccccc1] 107 |
| 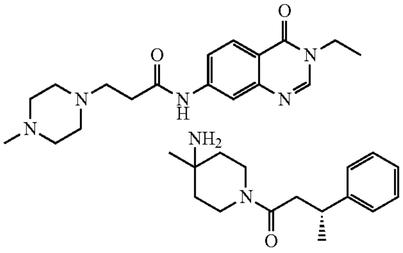 108 |
TABLE 4-continued
| Compound |
| --- |
| 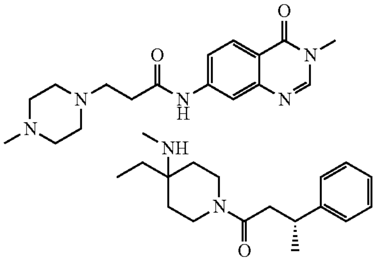 109 |
| 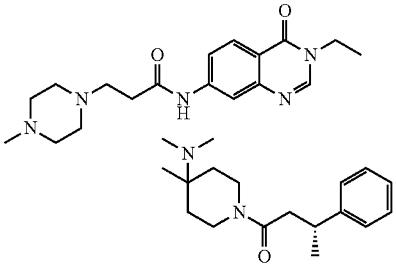 110 |
| 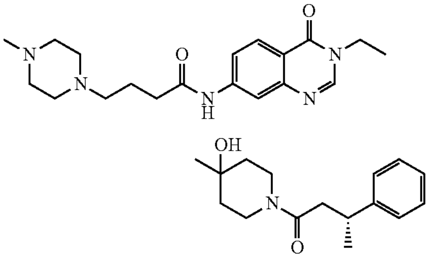 111 |

TABLE 4-continued
| Compound |
|---|
| 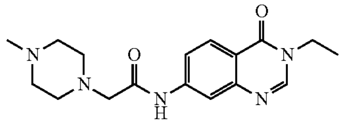 |
| 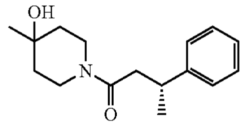 |
| 112 |
| 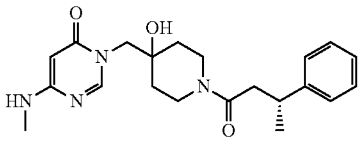 [SMILES: CNc1cc(=O)n(CC2(O)CCN(C(=O)C[C@@H](C)c3ccccc3)CC2)cn1] |
| 113 |
| 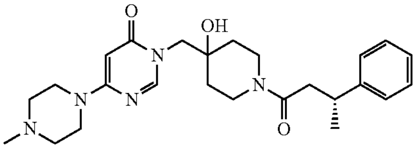 [SMILES: C[C@H](CC(=O)N1CCC(O)(Cn2cnc(N3CCN(C)CC3)cc2=O)CC1)c1ccccc1] |
| 114 |
| 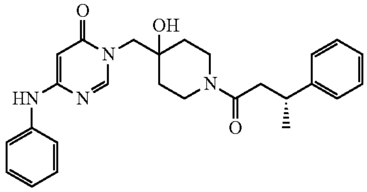 [SMILES: C[C@H](CC(=O)N1CCC(O)(Cn2cnc(Nc3ccccc3)cc2=O)CC1)c1ccccc1] |
| 115 |
| 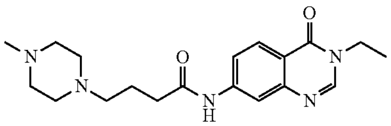 |
| 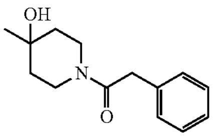 |
| 116 |
| 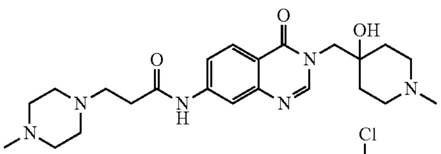 |
| 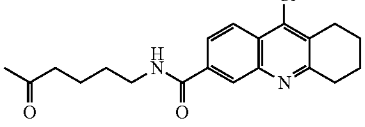 |
| 117 |
TABLE 4-continued
| Compound |
|---|
| 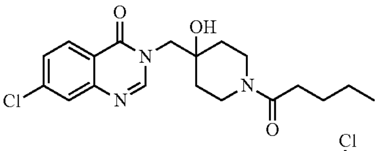 |
| 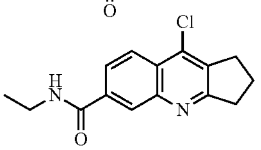 |
| 118 |
| 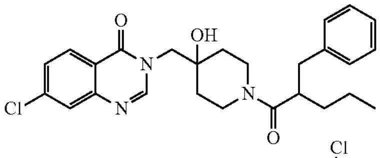 |
| 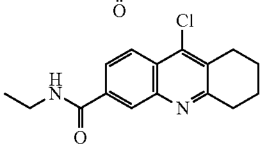 |
| 119 |
| 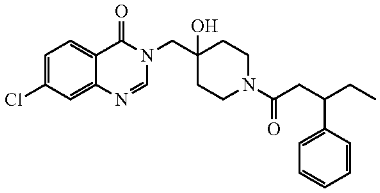 |
| 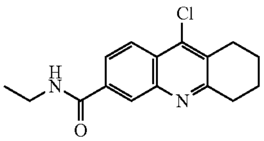 |
| 120 |
| 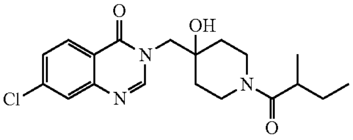 |
| 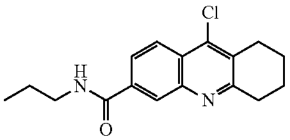 |
| 121 |
| 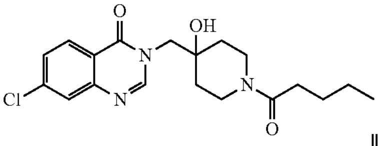 |
| 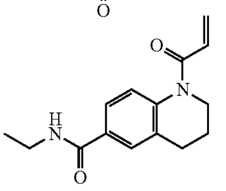 |
| 122 |

TABLE 4-continued

Compound

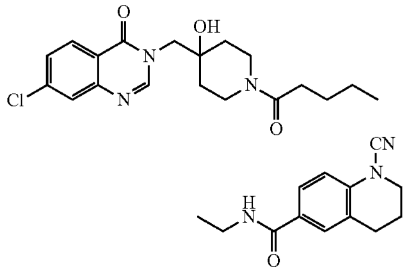

123

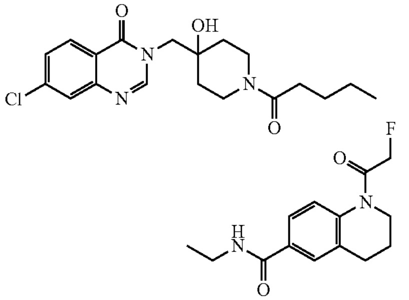

124

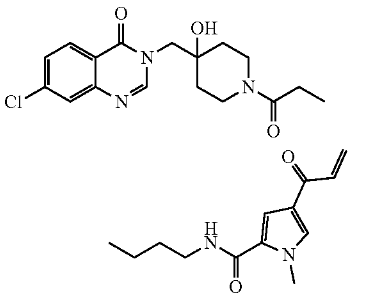

125

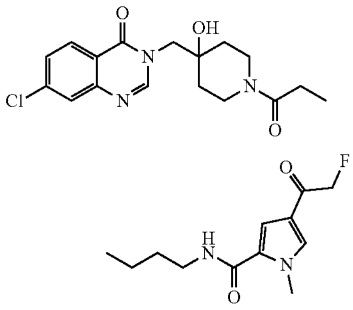

126

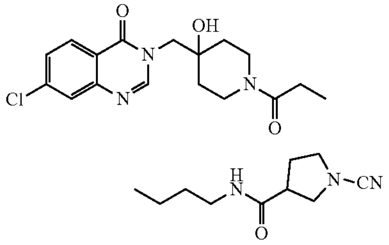

127

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A compound of Formula I:

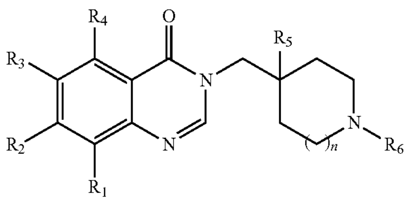

(I)

or a pharmaceutically acceptable salt thereof, wherein:

$R_1$, $R_3$, and $R_4$ are each H;

$R_2$ is halogen;

$R_5$ is —OH;

$R_6$ is —C(=O)$R_{10}$ or —C(O)N$R_7R_8$;

each $R_7$ and $R_8$ is independently H, alkenyl, or alkyl, wherein the alkyl is substituted with one or more $R_{12}$;

$R_{10}$ is alkyl, alkenyl, alkynyl, cycloalkyl, heterocycloalkyl, aryl, amino, heteroalkyl, alkylamino, aminoalkyl or heteroaryl, wherein the alkyl is substituted with one or more $R_{13}$ and the alkenyl and alkynyl are each independently optionally substituted with one or more $R_{13}$; and wherein the cycloalkyl, heterocycloalkyl, and heteroaryl are each independently substituted with one or more $R_{12}$, and the aryl is optionally substituted with one or more $R_{12}$;

each $R_{12}$ is independently at each occurrence aryl or heteroaryl, wherein the aryl and heteroaryl are each independently optionally substituted with one or more substituents selected from alkyl, haloalkyl, alkoxy, haloalkoxy, halogen, and —OH;

each $R_{13}$ is independently at each occurrence —OH, heteroalkyl, aryloxy, —$NH_2$, heterocycloalkyl, —O-aryl, —O-heteroaryl, —N$R_7$aryl, —N$R_7$heteroaryl, or —N$R_7$C(=O)$R_{14}$, wherein the heterocycloalkyl is substituted with one or more substituents selected from alkyl, haloalkyl, alkoxy, haloalkoxy, halogen, —$NO_2$, and —OH, and the heteroalkyl are each independently optionally substituted with one or more substituents selected from alkyl, haloalkyl, alkoxy, haloalkoxy, halogen, —$NO_2$, and —OH;

$R_{14}$ is alkyl, haloalkyl, arylalkyl, alkenyl, alkynyl, cycloalkyl, aryl, heterocyclyl, or heteroaryl, wherein the aryl and heteroaryl are each independently optionally substituted with one or more $R_{15}$; and wherein the alkyl, alkenyl, and alkynyl are each independently optionally substituted with one or more substituents selected from halogen and —OH;

each $R_{15}$ is independently at each occurrence halogen, alkyl, CN, —C(=O)alkyl, or —C(=O)alkenyl, wherein the alkyl and alkenyl is each independently substituted with one or more substituents selected from halogen and —OH; and n is 0 or 1.

2. The compound of claim 1, wherein n is 0.

3. The compound of claim 1, wherein n is 1.

4. The compound of claim 1, wherein $R_2$ is chloro.

5. The compound of claim 1, wherein $R_6$ is —C(═O)$R_{10}$.

6. The compound of claim 1, wherein $R_6$ is —C(O)$NR_7R_8$.

7. The compound of claim 1, wherein $R_7$ is H.

8. The compound of claim 5, wherein $R_{10}$ is alkyl, alkenyl, amino, alkylamino, alkynyl, cycloalkyl, heteroaryl, or aminoalkyl.

9. The compound of claim 5, wherein $R_{10}$ is heteroalkyl.

10. The compound of claim 1, wherein the aryl or heteroaryl of $R_{12}$ is further substituted with alkyl, halo, or alkyloxy.

11. The compound of claim 1, wherein the aryl or heteroaryl of $R_{12}$ is further substituted with halo or alkyloxy.

12. The compound of claim 1, wherein $R_{10}$ is alkyl, alkenyl, alkynyl, cycloalkyl, or heterocycloalkyl, wherein the alkyl is substituted with one or more $R_{13}$; the alkenyl and alkynyl are each independently optionally substituted with one or more $R_{13}$; and the cycloalkyl and heterocycloalkyl are each independently substituted with one or more $R_{12}$.

13. The compound of claim 12, wherein each $R_{13}$ is independently, at each occurrence, —OH, aryloxy, —$NH_2$, or —$NR_7C$(═O)$R_{14}$.

14. The compound of claim 13, wherein each $R_{14}$ is independently at each occurrence alkyl, haloalkyl, arylalkyl, alkenyl, heterocyclyl, or heteroaryl.

15. The compound of claim 1, wherein the compound is:

| Compound |
|---|
| 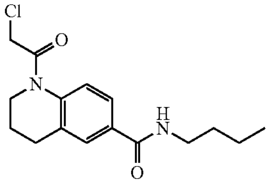 |
| 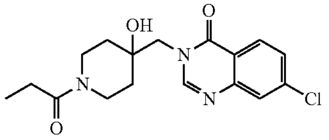 19 |
| 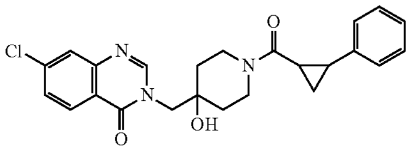 [SMILES: O=C(C1CC1c1ccccc1)N1CCC(O)(Cn2cnc3cc(Cl)ccc3c2=O)CC1] 30 |
| 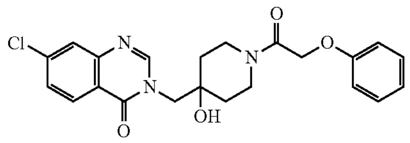 [SMILES: O=C(COc1ccccc1)N1CCC(O)(Cn2cnc3cc(Cl)ccc3c2=O)CC1] 31 |

-continued

| Compound |
|---|
| 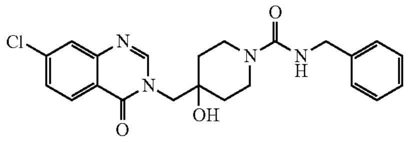 [SMILES: O=C(NCc1ccccc1)N1CCC(O)(Cn2cnc3cc(Cl)ccc3c2=O)CC1] 36 |
| 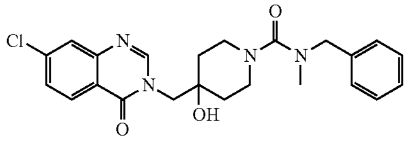 [SMILES: CN(Cc1ccccc1)C(=O)N1CCC(O)(Cn2cnc3cc(Cl)ccc3c2=O)CC1] 38 |
| 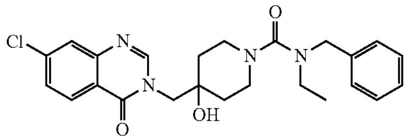 [SMILES: CCN(Cc1ccccc1)C(=O)N1CCC(O)(Cn2cnc3cc(Cl)ccc3c2=O)CC1] 39 |
| 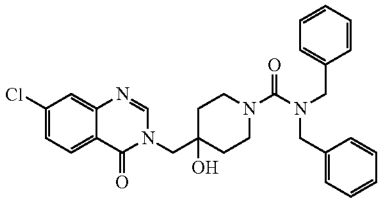 [SMILES: O=C(N1CCC(O)(Cn2cnc3cc(Cl)ccc3c2=O)CC1)N(Cc1ccccc1)Cc1ccccc1] 40 |
| 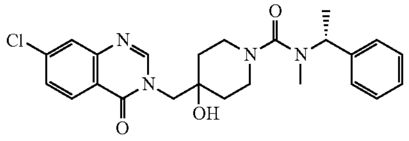 [SMILES: C[C@H](c1ccccc1)N(C)C(=O)N1CCC(O)(Cn2cnc3cc(Cl)ccc3c2=O)CC1] 41 |
| 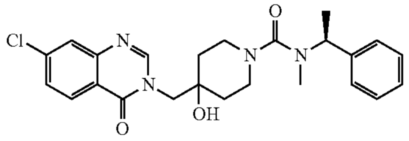 [SMILES: C[C@@H](c1ccccc1)N(C)C(=O)N1CCC(O)(Cn2cnc3cc(Cl)ccc3c2=O)CC1] 42 |
| 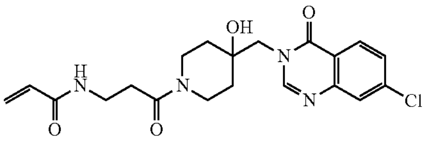 [SMILES: C=CC(=O)NCCC(=O)N1CCC(O)(Cn2cnc3cc(Cl)ccc3c2=O)CC1] 43 |
| 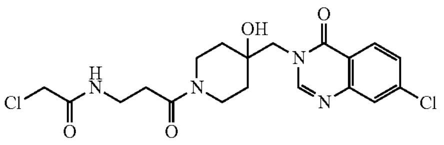 [SMILES: O=C(CCl)NCCC(=O)N1CCC(O)(Cn2cnc3cc(Cl)ccc3c2=O)CC1] 44 |

-continued
Compound
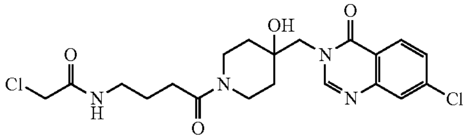 [SMILES: O=C(CCl)NCCCC(=O)N1CCC(O)(Cn2cnc3cc(Cl)ccc3c2=O)CC1]
45
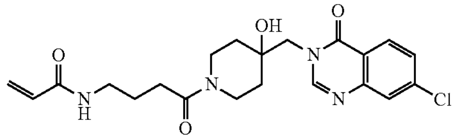 [SMILES: C=CC(=O)NCCCC(=O)N1CCC(O)(Cn2cnc3cc(Cl)ccc3c2=O)CC1]
46
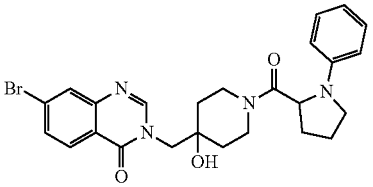 [SMILES: O=C(C1CCCN1c1ccccc1)N1CCC(O)(Cn2cnc3cc(Br)ccc3c2=O)CC1]
65
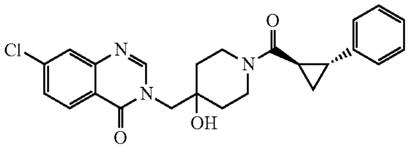 [SMILES: O=C([C@@H]1C[C@H]1c1ccccc1)N1CCC(O)(Cn2cnc3cc(Cl)ccc3c2=O)CC1]
74
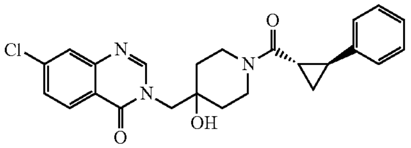 [SMILES: O=C([C@H]1C[C@@H]1c1ccccc1)N1CCC(O)(Cn2cnc3cc(Cl)ccc3c2=O)CC1]
75
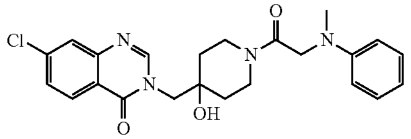 [SMILES: CN(CC(=O)N1CCC(O)(Cn2cnc3cc(Cl)ccc3c2=O)CC1)c1ccccc1]
79
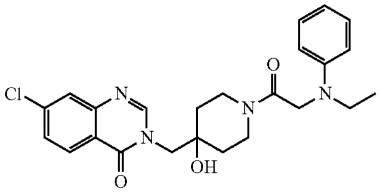 [SMILES: CCN(CC(=O)N1CCC(O)(Cn2cnc3cc(Cl)ccc3c2=O)CC1)c1ccccc1]
80
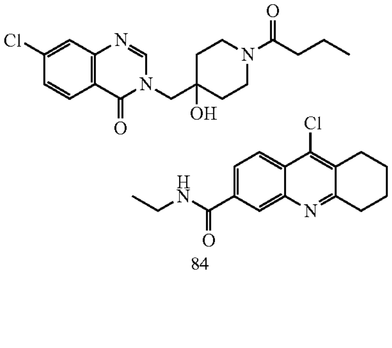
84
-continued
Compound
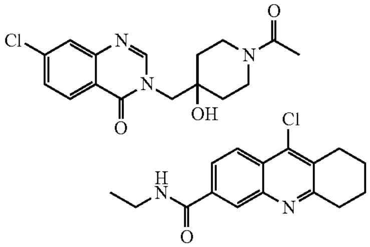
96
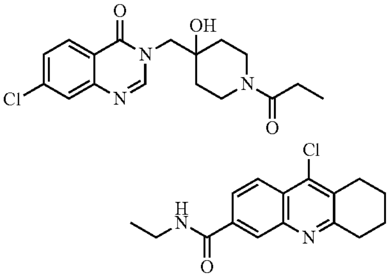
97
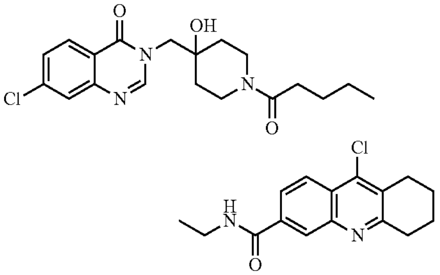
98
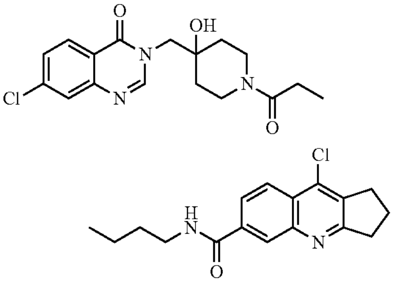
118
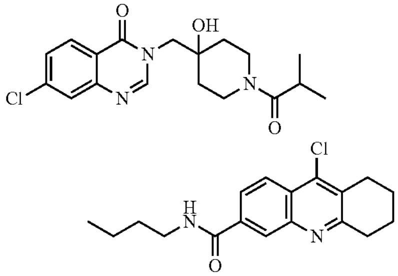
121

-continued

| Compound |
|---|
| 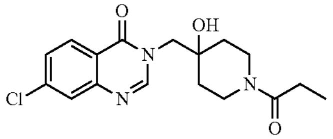 |
| 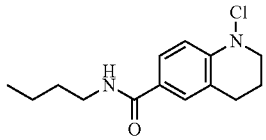 |
| 123 |
| 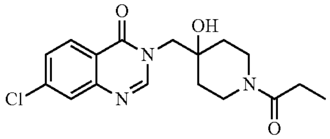 |
| 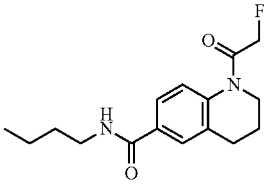 |
| 124 |
| 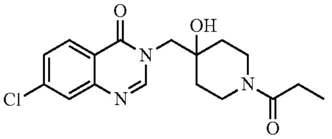 |
| 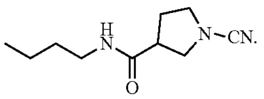 |
| 127 |

16. A pharmaceutical composition comprising a compound of claim 1, or a pharmaceutically acceptable salt thereof, and a pharmaceutically acceptable carrier.

17. A method of treating a disease or disorder modulated by USP7 comprising, administering to a subject in need thereof a compound of claim 1.

18. A method of treating cancer, comprising administering to a subject in need thereof a compound of claim 1.

19. A compound selected from compounds of the following structures:

| Compound |
|---|
| 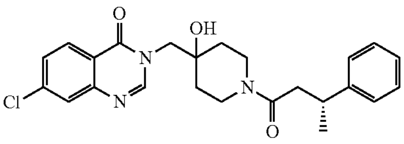 [SMILES: C[C@H](CC(=O)N1CCC(O)(Cn2cnc3cc(Cl)ccc3c2=O)CC1)c1ccccc1] |
| 1 |
| 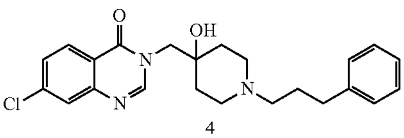 |
| 4 |

-continued

| Compound |
|---|
| 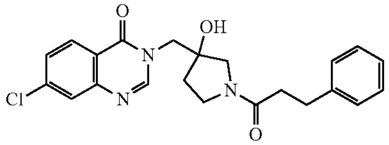 [SMILES: O=C(CCc1ccccc1)N1CCC(O)(Cn2cnc3cc(Cl)ccc3c2=O)C1] |
| 5 |
| 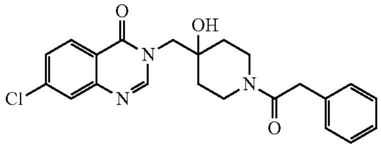 [SMILES: O=C(Cc1ccccc1)N1CCC(O)(Cn2cnc3cc(Cl)ccc3c2=O)CC1] |
| 7 |
| 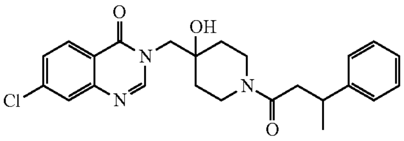 |
| 8 |
| 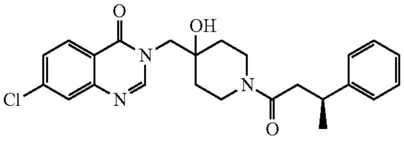 [SMILES: C[C@@H](CC(=O)N1CCC(O)(Cn2cnc3cc(Cl)ccc3c2=O)CC1)c1ccccc1] |
| 9 |
| 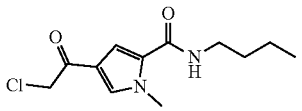 |
| 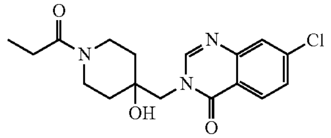 |
| 18 |
| 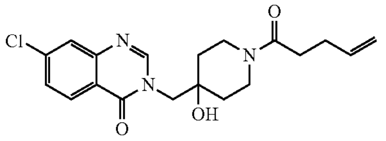 [SMILES: C=CCCC(=O)N1CCC(O)(Cn2cnc3cc(Cl)ccc3c2=O)CC1] |
| 20 |
| 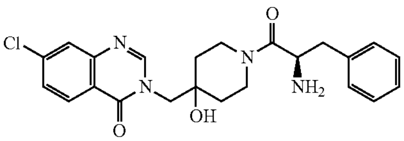 [SMILES: N[C@H](Cc1ccccc1)C(=O)N1CCC(O)(Cn2cnc3cc(Cl)ccc3c2=O)CC1] |
| 21 |
| 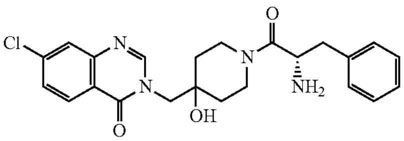 [SMILES: N[C@@H](Cc1ccccc1)C(=O)N1CCC(O)(Cn2cnc3cc(Cl)ccc3c2=O)CC1] |
| 22 |

-continued
Compound
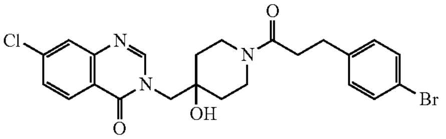 [SMILES: O=C(CCc1ccc(Br)cc1)N1CCC(O)(Cn2cnc3cc(Cl)ccc3c2=O)CC1]
23
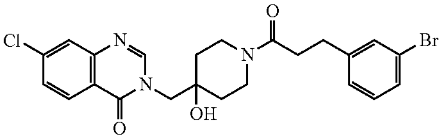 [SMILES: O=C(CCc1cccc(Br)c1)N1CCC(O)(Cn2cnc3cc(Cl)ccc3c2=O)CC1]
24
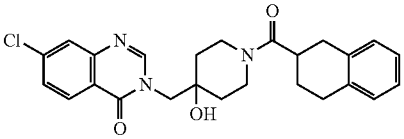 [SMILES: O=C(C1CCc2ccccc2C1)N1CCC(O)(Cn2cnc3cc(Cl)ccc3c2=O)CC1]
25
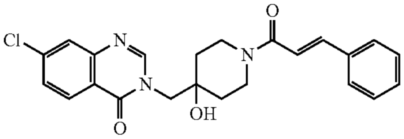 [SMILES: O=C(/C=C/c1ccccc1)N1CCC(O)(Cn2cnc3cc(Cl)ccc3c2=O)CC1]
26
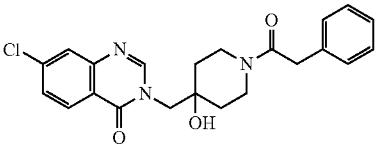 [SMILES: O=C(Cc1ccccc1)N1CCC(O)(Cn2cnc3cc(Cl)ccc3c2=O)CC1]
27
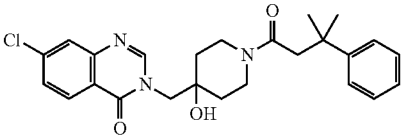 [SMILES: CC(C)(CC(=O)N1CCC(O)(Cn2cnc3cc(Cl)ccc3c2=O)CC1)c1ccccc1]
28
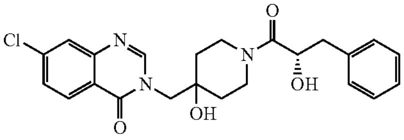 [SMILES: O=C([C@@H](O)Cc1ccccc1)N1CCC(O)(Cn2cnc3cc(Cl)ccc3c2=O)CC1]
32
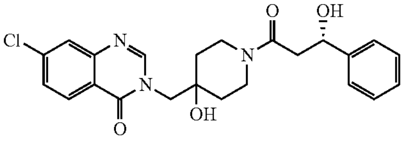 [SMILES: O=C(C[C@H](O)c1ccccc1)N1CCC(O)(Cn2cnc3cc(Cl)ccc3c2=O)CC1]
33
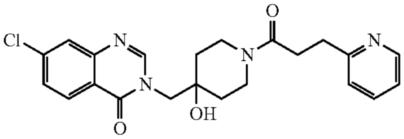 [SMILES: O=C(CCc1ccccn1)N1CCC(O)(Cn2cnc3cc(Cl)ccc3c2=O)CC1]
34
-continued
Compound
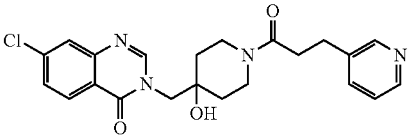 [SMILES: O=C(CCc1cccnc1)N1CCC(O)(Cn2cnc3cc(Cl)ccc3c2=O)CC1]
35
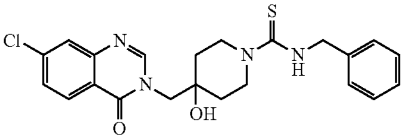 [SMILES: O=c1c2ccc(Cl)cc2ncn1CC1(O)CCN(C(=S)NCc2ccccc2)CC1]
37
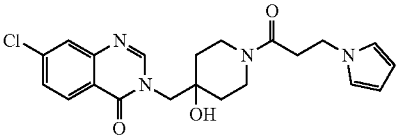 [SMILES: O=C(CCn1cccc1)N1CCC(O)(Cn2cnc3cc(Cl)ccc3c2=O)CC1]
51
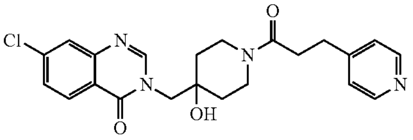 [SMILES: O=C(CCc1ccncc1)N1CCC(O)(Cn2cnc3cc(Cl)ccc3c2=O)CC1]
52
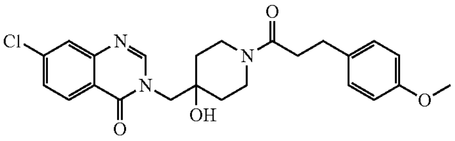 [SMILES: COc1ccc(CCC(=O)N2CCC(O)(Cn3cnc4cc(Cl)ccc4c3=O)CC2)cc1]
53
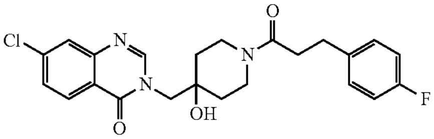 [SMILES: O=C(CCc1ccc(F)cc1)N1CCC(O)(Cn2cnc3cc(Cl)ccc3c2=O)CC1]
54
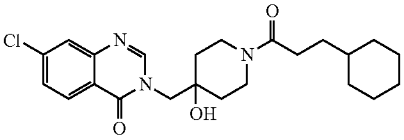 [SMILES: O=C(CCC1CCCCC1)N1CCC(O)(Cn2cnc3cc(Cl)ccc3c2=O)CC1]
55
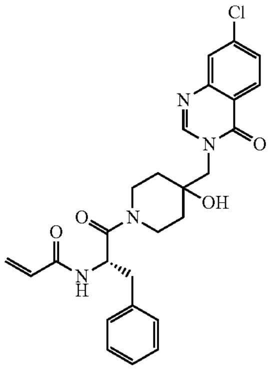 [SMILES: C=CC(=O)N[C@@H](Cc1ccccc1)C(=O)N1CCC(O)(Cn2cnc3cc(Cl)ccc3c2=O)CC1]
59

| Compound |
|---|
| 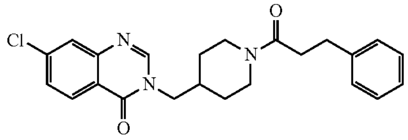 [SMILES: O=C(CCc1ccccc1)N1CCC(Cn2cnc3cc(Cl)ccc3c2=O)CC1] |
| 60 |
| 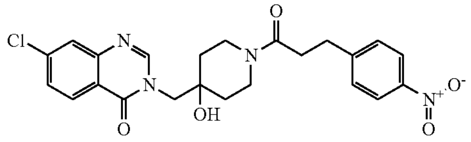 |
| 61 |
| 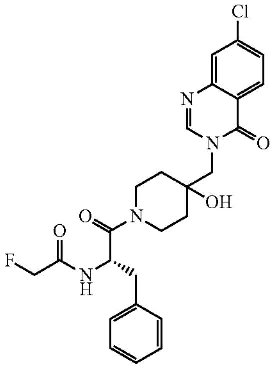 [SMILES: O=C(CF)N[C@@H](Cc1ccccc1)C(=O)N1CCC(O)(Cn2cnc3cc(Cl)ccc3c2=O)CC1] |
| 62 |
| 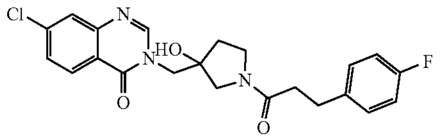 [SMILES: O=C(CCc1ccc(F)cc1)N1CCC(O)(Cn2cnc3cc(Cl)ccc3c2=O)C1] |
| 66 |
| 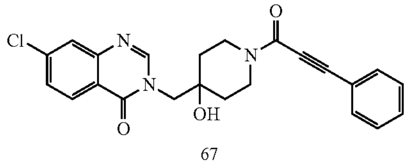 |
| 67 |
| 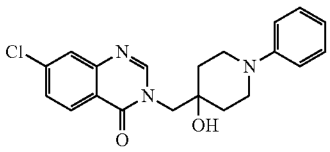 [SMILES: O=c1c2ccc(Cl)cc2ncn1CC1(O)CCN(c2ccccc2)CC1] |
| 70 |
| 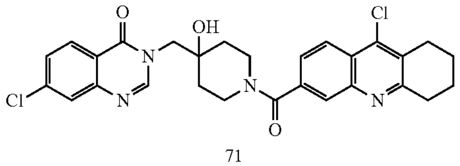 |
| 71 |
| Compound |
|---|
| 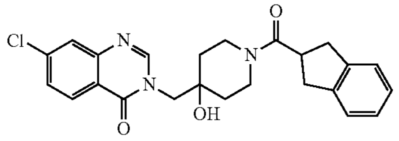 [SMILES: O=C(C1Cc2ccccc2C1)N1CCC(O)(Cn2cnc3cc(Cl)ccc3c2=O)CC1] |
| 81 |
| 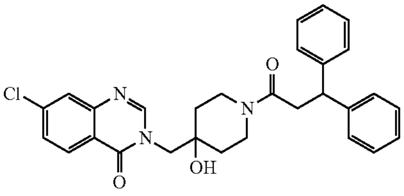 [SMILES: O=C(CC(c1ccccc1)c1ccccc1)N1CCC(O)(Cn2cnc3cc(Cl)ccc3c2=O)CC1] |
| 82 |
| 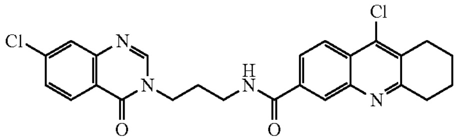 [SMILES: O=C(NCCCn1cnc2cc(Cl)ccc2c1=O)c1ccc2c(Cl)c3c(nc2c1)CCCC3] |
| 85 |
| 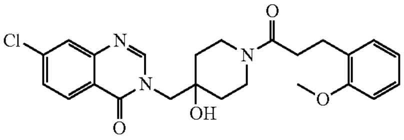 [SMILES: COc1ccccc1CCC(=O)N1CCC(O)(Cn2cnc3cc(Cl)ccc3c2=O)CC1] |
| 87 |
| 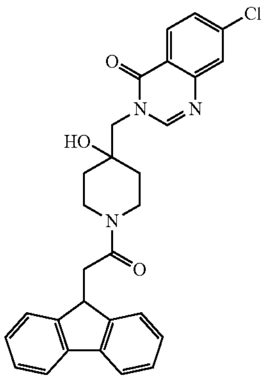 [SMILES: O=C(CC1c2ccccc2-c2ccccc21)N1CCC(O)(Cn2cnc3cc(Cl)ccc3c2=O)CC1] |
| 88 |
| 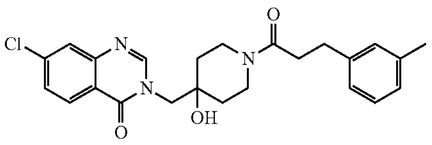 [SMILES: Cc1cccc(CCC(=O)N2CCC(O)(Cn3cnc4cc(Cl)ccc4c3=O)CC2)c1] |
| 89 |
| 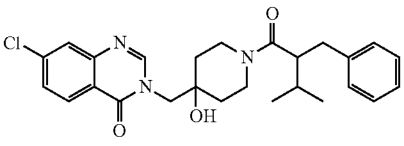 [SMILES: CC(C)C(Cc1ccccc1)C(=O)N1CCC(O)(Cn2cnc3cc(Cl)ccc3c2=O)CC1] |
| 91 |

| Compound |
|---|
| 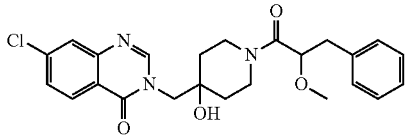 [SMILES: COC(Cc1ccccc1)C(=O)N1CCC(O)(Cn2cnc3cc(Cl)ccc3c2=O)CC1] |
| 92 |
| 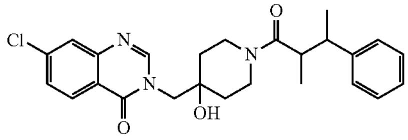 [SMILES: CC(C(=O)N1CCC(O)(Cn2cnc3cc(Cl)ccc3c2=O)CC1)C(C)c1ccccc1] |
| 93 |
| 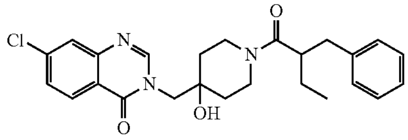 [SMILES: CCC(Cc1ccccc1)C(=O)N1CCC(O)(Cn2cnc3cc(Cl)ccc3c2=O)CC1] |
| 94 |
| 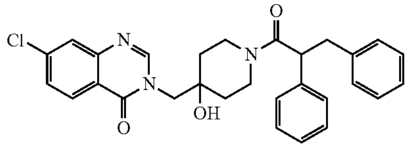 [SMILES: O=C(C(Cc1ccccc1)c1ccccc1)N1CCC(O)(Cn2cnc3cc(Cl)ccc3c2=O)CC1] |
| 95 |
| 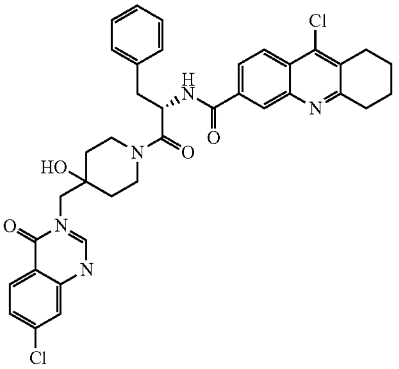 |
| 99 |
| 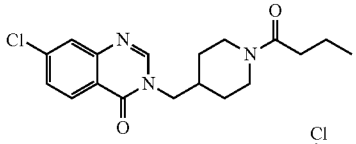 |
| 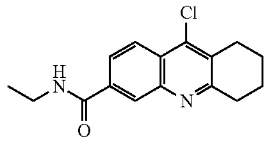 |
| 100 |
| 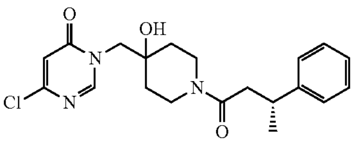 [SMILES: C[C@H](CC(=O)N1CCC(O)(Cn2cnc(Cl)cc2=O)CC1)c1ccccc1] |
| 107 |
| Compound |
|---|
| 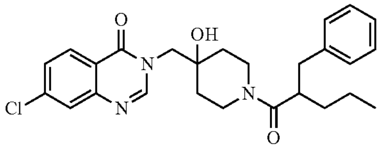 |
| 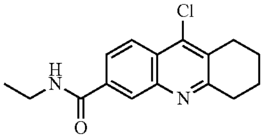 |
| 119 |
| 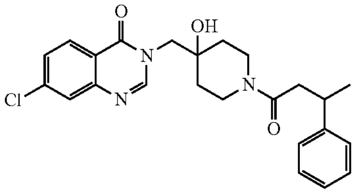 |
| 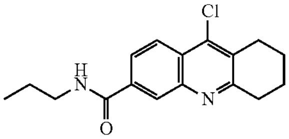 |
| 120 |
| 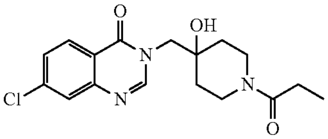 |
| 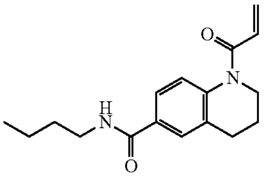 |
| 122 |
| 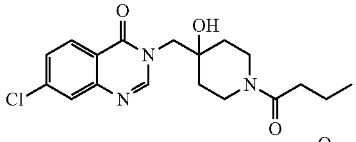 |
| 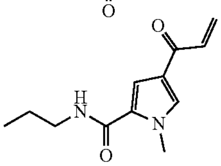 |
| 125 |

-continued
| Compound |
| --- |
| 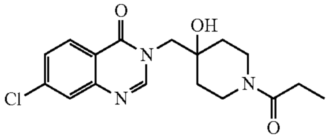 |
| 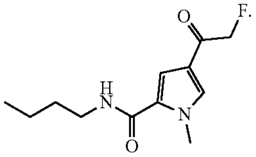 126 |
*    *    *    *    *